United States Patent
Altpeter et al.

(10) Patent No.: US 9,187,757 B2
(45) Date of Patent: Nov. 17, 2015

(54) ISOLATION AND TARGETED SUPPRESSION OF LIGNIN BIOSYNTHETIC GENES

(75) Inventors: Fredy Altpeter, Gainesville, FL (US); Walid Mohamed Fouad, Gainesville, FL (US); Maria Gallo, Gainesville, FL (US); Je Hyeong Jung, Gainesville, FL (US); Yuan Xiong, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 296 days.

(21) Appl. No.: 13/376,286

(22) PCT Filed: Jun. 5, 2010

(86) PCT No.: PCT/US2010/037555
§ 371 (c)(1),
(2), (4) Date: Mar. 20, 2012

(87) PCT Pub. No.: WO2010/141928
PCT Pub. Date: Dec. 9, 2010

(65) Prior Publication Data
US 2012/0180157 A1    Jul. 12, 2012

Related U.S. Application Data

(60) Provisional application No. 61/217,950, filed on Jun. 5, 2009.

(51) Int. Cl.
C12N 15/82    (2006.01)
C12N 15/63    (2006.01)
A01H 5/00    (2006.01)

(52) U.S. Cl.
CPC ........ *C12N 15/8218* (2013.01); *C12N 15/8255* (2013.01)

(58) Field of Classification Search
None
See application file for complete search history.

(56) References Cited

U.S. PATENT DOCUMENTS

| | | |
|---|---|---|
| 4,761,373 A | 8/1988 | Anderson et al. |
| 4,769,061 A | 9/1988 | Comai |
| 4,810,648 A | 3/1989 | Stalker |
| 4,940,835 A | 7/1990 | Shah et al. |
| 4,945,050 A | 7/1990 | Sanford et al. |
| 4,975,374 A | 12/1990 | Goodman et al. |
| 4,987,071 A | 1/1991 | Cech et al. |
| 5,013,659 A | 5/1991 | Bedbrook et al. |
| 5,023,179 A | 6/1991 | Lam et al. |
| 5,034,322 A | 7/1991 | Rogers et al. |
| 5,036,006 A | 7/1991 | Sanford et al. |
| 5,093,246 A | 3/1992 | Cech et al. |
| 5,100,792 A | 3/1992 | Sanford et al. |
| 5,106,739 A | 4/1992 | Comai et al. |
| 5,116,742 A | 5/1992 | Cech et al. |
| 5,162,602 A | 11/1992 | Somers et al. |
| 5,256,558 A | 10/1993 | Coruzzi et al. |
| 5,270,163 A | 12/1993 | Gold et al. |
| 5,276,268 A | 1/1994 | Strauch et al. |
| 5,304,730 A | 4/1994 | Lawson et al. |
| 5,495,071 A | 2/1996 | Fischhoff et al. |
| 5,554,798 A | 9/1996 | Lundquist et al. |
| 5,561,236 A | 10/1996 | Leemans et al. |
| 5,569,823 A | 10/1996 | Schreier et al. |
| 5,582,981 A | 12/1996 | Toole et al. |
| 5,589,610 A | 12/1996 | De Beuckeleer et al. |
| 5,591,616 A | 1/1997 | Hiei et al. |
| 5,595,877 A | 1/1997 | Gold et al. |
| 5,599,672 A | 2/1997 | Liang et al. |
| 5,625,136 A | 4/1997 | Koziel et al. |
| 5,639,948 A | 6/1997 | Michiels et al. |
| 5,661,017 A | 8/1997 | Dunahay et al. |
| 5,723,763 A | 3/1998 | Mariani et al. |
| 5,767,366 A | 6/1998 | Sathasivan et al. |
| 5,817,785 A | 10/1998 | Gold et al. |
| 5,879,903 A | 3/1999 | Strauch et al. |
| 5,928,937 A | 7/1999 | Kakefuda et al. |
| 6,084,155 A | 7/2000 | Volrath et al. |
| 6,329,504 B1 | 12/2001 | Liang et al. |
| 6,337,431 B1 | 1/2002 | Tricoli et al. |
| 6,344,318 B1 | 2/2002 | Gold et al. |

(Continued)

FOREIGN PATENT DOCUMENTS

| | | |
|---|---|---|
| EP | 0138341 | 4/1985 |
| EP | 0242246 | 10/1987 |

(Continued)

OTHER PUBLICATIONS

Zhao et al, 2011, Trends Plant Sci., 16:227-233.*
Ragg et al, 1981, J. Biol. Chem., 256:10061-10065.*
Hatfield et al, 1994, J. Sci. Food Agric., 65:51-58.*
Kajita, S. et al. "Alterations in the biosynthesis of lignin in transgenic plants with chimeric genes for 4-coumarate:coenzyme A ligase" *Plant Cell Physiol.*, 1996, 37(7):957-965.
Lee, D. et al. "Antisense suppression of 4-coumarate:coenzyme A ligase activity in Arabidopsis leads to altered lignin subunit composition" *The Plant Cell*, 1997, 9:1985-1998.

(Continued)

*Primary Examiner* — David H Kruse
*Assistant Examiner* — Jason Deveau Rosen
(74) *Attorney, Agent, or Firm* — Saliwanchik, Lloyd & Eisenschenk

(57) ABSTRACT

The subject invention concerns materials and methods for modulating lignin biosynthesis in sugarcane plants. In one embodiment, lignin biosynthesis is down-regulated. Genes and the proteins encoded thereby that can be targeted for achieving down-regulation of lignin in sugarcane include, for example, 4-coumarate-CoA ligase (4CL). In one embodiment, the 4CL gene is 4CL-M, 4CL-N, or 4CL-L. The subject invention also concerns a sugarcane plant, specific plant tissue, and plant cells having modulated (e.g., down-regulated) lignin biosynthesis. The subject invention also concerns methods for producing a sugarcane plant having modulated (e.g., decreased or down-regulated) biosynthesis of lignin.

54 Claims, No Drawings

(56) References Cited

U.S. PATENT DOCUMENTS

| | | | |
|---|---|---|---|
| 6,410,718 B1 | 6/2002 | Bloksberg et al. | |
| 6,420,629 B1 | 7/2002 | Xue et al. | |
| 6,455,760 B1 | 9/2002 | Zhao et al. | |
| 6,462,185 B1 | 10/2002 | Takakura et al. | |
| 6,506,559 B1 | 1/2003 | Fire et al. | |
| 6,696,623 B1 | 2/2004 | Doerner et al. | |
| 6,933,116 B2 | 8/2005 | Gold et al. | |
| 7,056,704 B2 | 6/2006 | Tuschl et al. | |
| 7,078,196 B2 | 7/2006 | Tuschl et al. | |
| 7,232,086 B2 | 6/2007 | Morise | |
| 7,282,564 B2 | 10/2007 | Mello et al. | |
| 7,365,058 B2 | 4/2008 | Stoffel et al. | |
| 7,365,185 B2 * | 4/2008 | Boukharov et al. | 536/24.1 |
| 7,368,236 B2 | 5/2008 | Gold et al. | |
| 7,538,095 B2 | 5/2009 | Fire et al. | |
| 7,700,759 B2 | 4/2010 | Prasad et al. | |
| 7,723,575 B2 | 5/2010 | Alibhai et al. | |
| 7,868,149 B2 * | 1/2011 | Boukharov et al. | 536/23.1 |
| 2001/0016956 A1 | 8/2001 | Ward et al. | |
| 2003/0084486 A1 | 5/2003 | Bruce et al. | |
| 2003/0175732 A1 | 9/2003 | Puigdomenech et al. | |
| 2003/0177536 A1 | 9/2003 | Grundler et al. | |
| 2004/0019934 A1 | 1/2004 | Ekramoddoullah et al. | |
| 2004/0067506 A1 | 4/2004 | Scheres et al. | |
| 2004/0078841 A1 | 4/2004 | Atkinson et al. | |
| 2004/0123349 A1 | 6/2004 | Xie et al. | |
| 2005/0278800 A1 | 12/2005 | Elton et al. | |
| 2006/0260011 A1 | 11/2006 | Carter et al. | |
| 2007/0006346 A1 | 1/2007 | Alexandrov et al. | |
| 2008/0213871 A1 * | 9/2008 | Sticklen | 435/277 |
| 2009/0031441 A1 | 1/2009 | Matsuoka et al. | |
| 2009/0199307 A1 | 8/2009 | Kriz et al. | |

FOREIGN PATENT DOCUMENTS

| | | |
|---|---|---|
| EP | 0292435 | 11/1988 |
| EP | 0295959 | 12/1988 |
| EP | 0392225 | 10/1990 |
| WO | WO 93/07278 | 4/1993 |
| WO | WO 93/21335 | 10/1993 |
| WO | WO-02/20717 | 3/2002 |
| WO | WO 2008/064289 A2 | 5/2008 |
| WO | WO 2009/009830 A1 | 1/2009 |

OTHER PUBLICATIONS

Wagner, A. et al. "Suppression of 4-coumarate-CoA ligase in the coniferous gymnosperm *Pinus radiata*" Plant Physiology, 2009, 149:370-383.

Xiong, Y. et al. "RNAi suppression of 4-coumarate-CoA ligase (4CL) in sugarcane" In Vitro Cellular & Developmental Biology Animal, 45(Suppl. S):S81, Abstract No. P-2060, from *In Vitro Biology Meeting 2009*, Charleston, SC, Jun. 6-10, 2009.

Agrawal, N. et al. "RNA Interference: Biology, Mechanism, and Applications," Microbiology and Molecular Biology Reviews, Dec. 2003, pp. 657-685, vol. 67, No. 4.

Altschul, S.F. et al., "Basic Local Alignment Search Tool," J. Mol. Biol., 1990, pp. 403-410, vol. 215.

Altschul, S.F. et al., "Gapped BLAST and PSI-BLAST: a new generation of protein database search programs," Nucleic Acids Research, 1997, pp. 3389-3402, vol. 25, No. 17.

Bartel, D.P. et al., "Isolation of New Ribozymes from a Large Pool of Random Sequences," Science, Sep. 10, 1993, pp. 1411-1418, vol. 261.

Bassett, C.L. et al., "A minimal peach type II chlorophyll a/b-binding protein promoter retains tissue-specificity and light regulation in tomato," BMC Biotechnology, 2007, 7:47.

Bevan, M., "Binary *Agrobacterium* vectors for plant transformation," Nucleic Acids Research, 1984, pp. 8711-8721, vol. 12, No. 22.

Brusslan, J.A. et al., "Light-independent developmental regulation of *cab* gene expression in *Arabidopsis thaliana* seedlings," Proc. Natl. Acad. Sci. USA, Aug. 1992, pp. 7791-7795, vol. 89.

Bustos, M.M. et al., "Regulation of β-Glucuronidase Expression in Transgenic Tobacco Plants by an A/T-Rich *cis*-Acting Sequence Found Upstream of a French Bean β-Phaseolin Gene," The Plant Cell, Sep. 1989, pp. 839-853, vol. 1.

Chandler, V.L. et al., "Two Regulatory Genes of the Maize Anthocyanin Pathway Are Homologous: Isolation of *B* Utilitzing *R* Genomic Sequences," The Plant Cell, Dec. 1989, pp. 1175-1183, vol. 1.

Chengalrayan, K. et al., "Effect of Various Growth Regulators on Shoot Regeneration of Sugarcane," In Vitro Cell. Dev. Biol.—Plant, 2001, pp. 434-439, vol. 37.

Clancy, M. et al., "Splicing of the Maize *Sh1* First Intron is Essential for Enhancement of Gene Expression, and a T-Rich Motif Increases Expression without Affecting Splicing," Plant Physiology, Oct. 2002, pp. 918-929, vol. 130.

Deblaere, R. et al., "Vectors for Cloning in Plant Cells," Methods in Enzymology, 1987, pp. 277-292, vol. 153.

Ebert, P.R. et al., "Identification of an essential upstream element in the nopaline synthase promoter by stable and transient assays," Proc. Natl. Acad. Sci. USA, Aug. 1987, pp. 5745-5749, vol. 84.

Ehlting, J. et at, "Three 4-coumarate:coenzyme A ligases in *Arabidopsis thaliana* represent two evolutionary divergent classes in angiosperms," The Plant Journal, 1999, pp. 9-20, vol. 19, No. 1.

Ellington, A.D. et al., "In vitro selection of RNA molecules that bind specific ligands," Nature, Aug. 30, 1990, pp. 818-822, vol. 346, No. 6287.

Fromm, M.E. et al., "Inheritance and expression of chimeric genes in the progeny of transgenic maize plants" Biotechnology, 1990, pp. 833-839, vol. 8, No. 9, Abstract only.

Good, X. et al., "Reduced ethylene synthesis by transgenic tomatoes expressing *S*-adenosylmethionine hydrolase," Plant Molecular Biology, 1994, pp. 781-790, vol. 26.

Gordon-Kamm, W.J. et al., Transformation of Maize Cells and Regeneration of Fertile Transgenic Plants, The Plant Cell, Jul. 1990, pp. 603-618, vol. 2.

Green, P.J. et al., "Binding site requirements for pea nuclear protein factor GT-1 correlate with sequences required for light-dependent transcriptional activation of the *rbcS-3A* gene," The EMBO Journal, 1988, pp. 4035-4044, vol. 7, No. 13.

Haseloff, J. et al., "Simple RNA enzymes with new and highly specific endoribonuclease activities," Nature, Aug. 1988, pp. 585-591, vol. 334.

Hofgen, R. et al., "Storage of competent cells for *Agrobacterium* transformation," Nucleic Acids Research, 1988, p. 9877, vol. 16, No. 20.

Hoppe-Seyler, F. et al., "Peptide aptamers: powerful new tools for molecular medicine," J. Mol. Med., 2000, pp. 426-430, vol. 78.

Hudspeth, R.L. et al., "Structure and expression of the maize gene encoding the phosphenolpyruvate carboxylase isozyme involved in $C_4$ photosynthesis," Plant Molecular Biology, 1989, pp. 579-589, vol. 12.

James, V.A. et al., "Stress inducible expression of the *DREB1A* transcription factor from xeric, *Hordeum spontaneum* L. in turf and forage grass (*Paspalum notatum* Flugge) enhances abiotic stress tolerance," Transgenic Res., 2008, pp. 93-104, vol. 17.

Jordano, J. et al. A Sunflower Helianthinin Gene Upstream Sequence Ensemble Contains an Enhancer and Sites of Nuclear Protein Interaction, The Plant Cell, Sep. 1989, pp. 855-866, vol. 1.

Karlin, S. et al., "Methods for assessing the statistical significance of molecular sequence features by using general scoring schemes," Proc. Natl. Acad. Sci. USA, Mar. 1990, pp. 2264-2268, vol. 87.

Karlin, S. et al., "Applications and statistics for multiple high-scoring segments in molecular sequences," Proc. Natl. Acad. Sci. USA, Jun. 1993, pp. 5873-5877, vol. 90.

Koziel, M.G. et al., "Field performance of elite transgenic maize plants expressing an insecticidal protein derived from *Bacillus thuringiensis*" Nature Biotechnology, 1993, pp. 194-200, vol. 11, Abstract only.

Klein, T.M. et al., "High-velocity microprojectiles for delivering nucleic acids into living cells," Nature, May 1987, pp. 70-73, vol. 327.

Kusaba, M. "RNE interference in crop plants," Current Opinion in Biotechnology, 2004, pp. 139-143, Vo. 15.

Kwon, H-B. et al., "Identification of a Light-Responsive Region of the Nuclear Gene Encoding the B Subunit of Chloroplast

(56) References Cited

OTHER PUBLICATIONS

Glyceraldehyde 3-Phosphate Dehydrogenase from *Arabidopsis thaliana*," *Plant Physiol.*, 1994, pp. 357-367, vol. 105.
Lawton, M.A. et al., "Expression of a soybean β-conclycinin gene under the control of the Cauliflower Mosaic Virus 35S and 19S promoters in transformed petunia tissues," *Plant Molecular Biology*, 1987, pp. 315-324, vol. 9.
Matsuoka, M. et al., "Tissue-specific light-regulated expression directed by the promoter of a $C_4$ gene, maize pyruvate, orthophosphate dikinase, in a $C_3$ plant, rice," *Proc. Natl. Acad. Sci. USA*, Oct. 1993, pp. 9586-9590, vol. 90.
Matsuoka, M. et al., "The promoters of two carboxylases in a $C_4$ plant (maize) direct cell-specific, light-regulated expression in a $C_3$ plant (rice)," *The Plant Journal*, 1994, pp. 311-319, vol. 6, No. 3.
Meier, I. et al., "Elicitor-Inducible and Constitutive in Vivo DNA Footprints Indicate Novel *cis*-Acting Elements in the Promoter of a Parsley Gene Encoding Pathogenesis-Related Protein 1," *The Plant Cell*, Mar. 1991, pp. 309-315, vol. 3.
Milhavet, O. et al., "RNA Interference in Biology and Medicine," *Pharmacological Reviews*, 2003, pp. 629-648, vol. 55, No. 4.
Odell, J.T. et al., "Identification of DNA sequences required for activity of the cauliflower mosaic virus 35S promoter," *Nature*, Feb. 1985, pp. 810-812, vol. 313.
Paszkowski, J. et al., "Direct gene transfer to plants," *The EMBO Journal*, 1984, pp. 2717-2722, vol. 3. No. 12.
Potrykus, I. et al., "Molecular and general genetics of a hybrid foreign gene introduced into tobacco by direct gene transfer," *Mol. Gen. Genet.*, 1985, pp. 169-177, vol. 199.
Reich, T.J. et al., "Efficient transformation of alfalfa protoplasts by the intranuclear microinjection of Ti plasmids" *Nature Biotechnology*, 1986, pp. 1001-1004, vol. 4, Abstract only.
Richins, R.D. et al., "Sequence of figwort mosaic virus DNA (caulimovirus group)," *Nucleic Acids Research*, 1987, pp. 8451-8466, vol. 15, No. 20.
Sullivan, T.D. et al., "Isolation and characterization of a maize chlorophyll a/b binding protein gene that produces high levels of mRNA in the dark," *Mol. Gen. Genet.*, 1989, pp. 431-440, vol. 215.
Tamura, K. et al., "MEGA4: Molecular Evolutionary Genetics Analysis (MEGA) Software Version 4.0," *Molecular Biology and Evolution*, 2007, pp. 1596-1599, vol. 24, No. 8.
Theander, O. et al., "Studies on Dietary Fiber. 3. Improved Procedures for Analysis of Dietary Fiber," *J. Agric. Food Chem.*, 1986, pp. 330-336, vol. 34.
Uknes, S. et al., "Regulation of Pathogenesis-Related Protein-1a Gene Expression in Tobacco," *The Plant Cell*, Feb. 1993, pp. 159-169, vol. 5.
Walker, J.C. et al., "DNA sequences required for anaerobic expression of the maize alcohol dehydrogenase 1 gene," *Proc. Natl. Acad. Sci. USA*, Oct. 1987, pp. 6624-6628, vol. 84.
Wang, Y. et al., "Characterization of *cis*-Acting Elements Regulating Transcription from the Promoter of a Constitutively Active Rice Actin Gene," *Molecular and Cellular Biology*, Aug. 1992, pp. 3399-3406, vol. 12, No. 8.
Xu, D. et al., "Systemic induction of a potato *pin2* promoter by wounding, methyl jasmonate, and abscisic acid in transgenic rice plants," *Plant Molecular Biology*, 1993, pp. 573-588, vol. 22.
Yamamoto, N. et al., "The promoter of a pine photosynthetic gene allows expression of a β-glucuronidase reporter gene in transgenic rice plants in a light-independent but tissue-specific manner" *Plant Cell Physiol*, 1994, pp. 773-778, vol. 35, No. 5, Abstract only.
Yamamoto, Y.Y. et al., "Light-responsive elements of the tobacco PSI-D gene are located both upstream and within the transcribed region," *The Plant Journal*, 1997, pp. 255-265, vol. 12, No. 2.
Yang, N-S. et al., "Maize sucrose synthase-1 promoter directs phloem cell-specific expression of *Gus* gene in transgenic tobacco plants," *Proc. Natl. Acad. Sci. USA*, Jun. 1990, pp. 4144-4148, vol. 87.
Yang, T.T. et al., "Optimized codon usage and chromophore mutations provide enhanced sensitivity with the green fluorescent protein," *Nucleic Acids Res.*, Nov. 15, 1996, pp. 4592-4593 (Abstract only) vol. 24, No. 22.
Zhang, J.Z. et al., DNA Sequences That Activate Isocitrate Lyase Gene Expression during Late Embryogenesis and during Postgerminative Growth, *Plant Physiol.*, 1996, pp. 1069-1079, vol. 110.
Zubieta, C. et al., "Structural Basis for the Modulation of Lignin Monomer Methylation by Caffeic Acid/5 Hydroxyferulic 3/5-*O*-Methyltransferase," *The Plant Cell*, Jun. 2002, pp. 1265-1277, vol. 14.

* cited by examiner

ISOLATION AND TARGETED SUPPRESSION OF LIGNIN BIOSYNTHETIC GENES

GOVERNMENT SUPPORT

The subject matter of this application has been supported by a research grant from the USDA-CSRRES under grant number 00075788. Accordingly, the government has certain rights in this invention.

CROSS-REFERENCE TO RELATED APPLICATIONS

The present application is the National Stage of International Application Number PCT/US2010/037555, filed Jun. 5, 2010, which claims the benefit of U.S. Provisional Application Ser. No. 61/217,950, filed Jun. 5, 2009, each of which is hereby incorporated by reference herein in its entirety, including any figures, tables, nucleic acid sequences, amino acid sequences, and drawings.

BACKGROUND OF THE INVENTION

Sugarcane is the highest yielding biomass producer. Typically, farmers reduce the sugarcane post-harvest leaf residue by open air burning, which negatively impacts air quality. Fuel grade ethanol can be made from sugarcane leaf litter residue following acid hydrolysis pre-treatments to remove lignin which acts as a physical barrier to enzyme hydrolysis. Thus, down-regulation of lignin biosynthesis pathway enzymes is a promising strategy to increase the efficiency of bio-ethanol production from hemicellulosic sugarcane residues. In the lignin pathway, 4-coumarate-CoA ligase (4CL) is a key enzyme that catalyze the formation of CoA thiol esters of 4-coumarate and other hydroxycinnamates. However, sugarcane has a complex polypoid genome and these genes belong to a large gene family. Their broad substrate specificities have made it difficult to identify orthologs that are specifically involved in lignin biosynthesis. Thus, there remains a need in the art for means for inhibiting lignin biosynthesis in sugarcane.

BRIEF SUMMARY OF THE INVENTION

The subject invention concerns materials and methods for modulating lignin biosynthesis in sugarcane plants. In one embodiment, lignin biosynthesis is down-regulated. Genes and the proteins encoded thereby that can be targeted for achieving down-regulation of lignin in sugarcane include, for example, 4-coumarate-CoA ligase (4CL). In a specific embodiment, the 4CL gene is 4CL-M, 4CL-N, or 4CL-L. In another embodiment, lignin biosynthesis is decreased or down-regulated in stem tissue of a sugarcane plant. Expression of one or more target genes can be inhibited or down-regulated using standard methods known in the art. In a specific embodiment, expression of the 4CL-L gene is suppressed or down-regulated.

The subject invention also concerns a sugarcane plant, plant tissue, and plant cells wherein lignin biosynthesis has been down-regulated. In a specific embodiment, expression of one or more 4CL genes is inhibited or down-regulated in the sugarcane plant.

The subject invention also concerns methods for producing a sugarcane plant having decreased or down-regulated biosynthesis of lignin. In one embodiment, lignin biosynthesis is decreased or down-regulated in leaf tissue of a sugarcane plant. In another embodiment, lignin biosynthesis is decreased or down-regulated in stem tissue of a sugarcane plant. In one embodiment, a method of the invention comprises suppressing or inhibiting the expression of one or more 4CL genes. In one embodiment, the gene is inhibited using antisense nucleic acid or RNA interference.

BRIEF DESCRIPTION OF THE SEQUENCES

SEQ ID NO:1 is a nucleotide sequence of a 4CL-L gene of the present invention.

SEQ ID NO:2 is a nucleotide sequence of a 4CL-M gene of the present invention.

SEQ ID NO:3 is a nucleotide sequence of a 4CL-N gene of the present invention.

SEQ ID NO:4 is a nucleotide sequence of a Sc4CL-Li RNAi construct of the present invention.

SEQ ID NO:5 is a nucleotide sequence of a Sc4CL-Mi RNAi construct of the present invention.

SEQ ID NO:6 is an amino acid sequence encoded by SEQ ID NO:1.

SEQ ID NO:7 is an amino acid sequence encoded by SEQ ID NO:2.

SEQ ID NO:8 is an amino acid sequence encoded by SEQ ID NO:3.

SEQ ID NO:9 is an amino acid sequence of *Arabidopsis thaliana* 4CL1.

SEQ ID NO:10 is an amino acid sequence of *Arabidopsis thaliana* 4CL2.

SEQ ID NO:11 is an amino acid sequence of *Arabidopsis thaliana* 4CL3.

SEQ ID NO:12 is an amino acid sequence of *Arabidopsis thaliana* 4CL4.

SEQ ID NO:13 is an amino acid sequence of Poplar 4CL1.

SEQ ID NO:14 is an amino acid sequence of Poplar 4CL2.

SEQ ID NO:15 is an amino acid sequence of Poplar 4CL3.

SEQ ID NO:16 is an amino acid sequence of Poplar 4CL4.

SEQ ID NO:17 is a gene specific primer based on the partial genomic DNA sequence of 4CL-L.

SEQ ID NO:18 is a gene specific primer based on the partial genomic DNA sequence of 4CL-L.

SEQ ID NO:19 is a forward primer for 4CL-N.

SEQ ID NO:20 is a reverse primer for 4CL-N.

SEQ ID NO:21 is a forward primer for 4CL-M and 4CL-L RNAi constructs.

SEQ ID NO:22 is a reverse primer for 4CL-M and 4CL-L RNAi constructs.

SEQ ID NO:23 is an amino acid sequence of a 4CL polypeptide of *Sorghum bicolor* 04g005210 (XP_002451647).

SEQ ID NO:24 is an amino acid sequence of a 4CL polypeptide of *Sorghum bicolor* 10g026130 (XP_002438783).

SEQ ID NO:25 is an amino acid sequence of a 4CL polypeptide of *Sorghum bicolor* 04g031010 (XP_002452704).

SEQ ID NO:26 is an amino acid sequence of a 4CL polypeptide of *Zea mays* LOC542166 (NP_001105258).

SEQ ID NO:27 is an amino acid sequence of a 4CL polypeptide of *Lolium perenne* 4CL3 (AAF37734).

SEQ ID NO:28 is an amino acid sequence of a 4CL polypeptide of *Lolium perenne* 4CL2 (AAF37733).

SEQ ID NO:29 is an amino acid sequence of a 4CL polypeptide of *Lolium perenne* 4CL1 (AAF37732).

SEQ ID NO:30 is an amino acid sequence of a 4CL polypeptide of *Oryza sativa* 4CL3 (NP_001046069).

SEQ ID NO:31 is an amino acid sequence of a 4CL polypeptide of *Oryza sativa* 4CL4 (NP_001058252).

SEQ ID NO:32 is an amino acid sequence of a 4CL polypeptide of *Oryza sativa* 4CL1 (NP_001061353).

SEQ ID NO:33 is an amino acid sequence of a 4CL polypeptide of *Oryza sativa* 4CL2 (NP_001047819).

SEQ ID NO:34 shows the conserved AMP-binding motif of *Arabidopsis thaliana* 4CL1.

SEQ ID NO:35 shows the conserved AMP-binding motif of *Arabidopsis thaliana* 4CL2.

SEQ ID NO:36 shows the conserved AMP-binding motif of *Arabidopsis thaliana* 4CL3.

SEQ ID NO:37 shows the conserved AMP-binding motif of *Arabidopsis thaliana* 4CL4.

SEQ ID NO:38 shows the conserved AMP-binding motif of Poplar 4CL1.

SEQ ID NO:39 shows the conserved AMP-binding motif of Poplar 4CL2.

SEQ ID NO:40 shows the conserved AMP-binding motif of Poplar 4CL3.

SEQ ID NO:41 shows the conserved AMP-binding motif of Poplar 4CL4.

SEQ ID NO:42 shows the conserved AMP-binding motif of Sugarcane 4CL1.

SEQ ID NO:43 shows the conserved AMP-binding motif of Sugarcane 4CLM.

SEQ ID NO:44 shows a signature motif of *Arabidopsis thaliana* 4CL1.

SEQ ID NO:45 shows a signature motif of *Arabidopsis thaliana* 4CL2.

SEQ ID NO:46 shows a signature motif of *Arabidopsis thaliana* 4CL3.

SEQ ID NO:47 shows a signature motif of *Arabidopsis thaliana* 4CL4.

SEQ ID NO:48 shows a signature motif of Poplar 4CL1.
SEQ ID NO:49 shows a signature motif of Poplar 4CL2.
SEQ ID NO:50 shows a signature motif of Poplar 4CL3.
SEQ ID NO:51 shows a signature motif of Poplar 4CL4.
SEQ ID NO:52 shows a signature motif of a Sugarcane 4CL1.

SEQ ID NO:53 shows a signature motif of a Sugarcane 4CLM.

SEQ ID NO:54 shows a common signature motif of 4CL genes.

DETAILED DESCRIPTION OF THE INVENTION

The subject invention concerns materials and methods for modulating lignin biosynthesis in plants, and in particular, sugarcane plants. In one embodiment, lignin biosynthesis is down-regulated in the plant. The subject invention contemplates the use of any method that can be used to inhibit or decrease expression of a gene (including at the transcriptional, post-transcriptional, and translational levels) and/or function or activity of a protein encoded by the gene. Genes, and the proteins encoded thereby, that can be targeted for achieving down-regulation of lignin biosynthesis in sugarcane include, but are not limited to, 4-coumarate-CoA ligase (4CL). In one embodiment, a 4CL gene encodes a 4CL polypeptide comprising an AMP-binding motif sequence (e.g., SEQ ID NO:34) and/or the signature motif sequence of SEQ ID NO:54. In one embodiment, the 4CL gene is 4CL-M, 4CL-L, or 4CL-N. In one embodiment, a 4CL-L gene encodes a polypeptide having the amino acid sequence shown in SEQ ID NO:6, or a fragment or variant thereof. In a further embodiment, a 4CL-M gene encodes a polypeptide having the amino acid sequence shown in SEQ ID NO:7, or a fragment or variant thereof. In another embodiment, a 4CL-N gene encodes a polypeptide having the amino acid sequence shown in SEQ ID NO:8, or a fragment or variant thereof. In a specific embodiment, the 4CL-L gene comprises all or a part of the nucleotide sequence shown in SEQ ID NO:1 and the 4CL-M gene comprises all or a part of the nucleotide sequence shown in SEQ ID NO:2. In a specific embodiment, the 4CL-N gene comprises all or a part of the nucleotide sequence shown in SEQ ID NO:3.

Expression of one or more target genes can be inhibited or down-regulated in a sugarcane plant using standard methods known in the art. In one embodiment, lignin biosynthesis is selectively down-regulated in leaf cells and/or tissue. In a specific embodiment, expression of one or more 4CL genes and/or translation or function of a protein encoded by a 4CL gene is suppressed or down-regulated. In one embodiment, a 4CL gene encodes a 4CL polypeptide comprising an AMP-binding motif sequence (e.g., SEQ ID NO:34) and/or the signature motif sequence of SEQ ID NO:54. In a more specific embodiment, expression of the 4CL-M, 4CL-L, and/or 4CL-N gene is suppressed or down-regulated. In one embodiment, expression of a target gene is down-regulated using antisense technology. In another embodiment, cosuppression technology can be used to inhibit or down-regulate expression of a target gene. In still another embodiment, expression of a target gene is down-regulated using RNA interference (RNAi) technology, including, for example, the use of short interfering RNA (siRNA). In a still further embodiment, mutations in a target gene, such as "knockout" mutations, can be provided in a sugarcane plant of the invention. Expression and/or activity (e.g., enzymatic activity) of a protein encoded by a target gene can also be inhibited, for example, by contacting the protein with an antibody or an aptamer that binds to and blocks functional activity of the protein.

Antisense technology can be used to inhibit expression of a target gene involved in lignin biosynthesis in sugarcane. In antisense methodologies, a nucleic acid that hybridizes with a nucleotide sequence of an mRNA of a target gene is provided in a plant cell. Nucleic acid constructs that when expressed provide the nucleic acid that hybridizes with the mRNA can be incorporated (e.g., stably) in the genome of a sugarcane plant. The antisense nucleic acid can hybridize to an entire coding strand of a target sequence, or to a portion thereof, or to a non-coding portion of a target sequence or to both a coding and non-coding portion of a target sequence. Antisense constructs can have, for example, at least about 70%, at least about 75%, at least about 80%, at least about 85%, at least about 90%, at least about 95%, at least about 96%, 97%, 98%, or 99% sequence identity, or up to 100% sequence identity to the portion of the mRNA that the antisense nucleic acid hybridizes with. Antisense nucleic acids can comprise any suitable number of nucleotides. For example, an antisense nucleic acid construct of the invention can comprise at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more nucleotides. In one embodiment, the antisense nucleic acid comprises at least about 40, or at least about 50, or at least about 60, or at least about 70, or at least about 80, or at least about 90, or at least about 100, or at least about 150, or at least about 200, or at least about 250, or at least about 300, or at least about 350, or at least about 400, or at least about 450, or at least about 500, or at least about 550, or at least about 600 or more nucleotides. In one embodiment, the antisense construct is selectively expressed in leaf cells and/or tissue of the plant, e.g., by use of a leaf-specific promoter. Antisense methods for down-regulating or inhibiting expression of a target gene are known in the art. Plants comprising and expressing the antisense nucleic acid constructs can be grown from cells transformed with and/or incorporating the nucleic acid construct.

Cosuppression or post-transcriptional gene silencing (PTGS) technology can also be used to inhibit expression of a target gene involved in lignin biosynthesis in sugarcane. Generally, a nucleic acid sequence corresponding to and having sequence homology with a target gene sequence is provided in a plant cell in a sense orientation and in a construct suitable for expression of the nucleic acid (e.g., a construct comprising the nucleic acid operably linked to a promoter sequence capable of driving transcription in a plant cell). The nucleic acid can have, for example, at least about 70%, at least about 75%, at least about 80%, at least about 85%, at least about 90%, at least about 95%, or at least about 96%, 97%, 98%, or 99% sequence identity, or up to 100% sequence identity to the target gene sequence. In one embodiment, the nucleic acid construct is selectively expressed in leaf cells and/or tissue of the plant, e.g., by use of a leaf-specific promoter. Plants comprising and expressing the nucleic acid constructs can be grown from cells transformed with and/or incorporating the nucleic acid construct.

RNA interference (RNAi) technologies can also be used to inhibit expression of a target gene involved in lignin biosynthesis in a sugarcane plant. In RNAi, a double-stranded RNA molecule that is complementary to all or a portion of an expressed RNA of a target gene is provided in a plant cell. The double-stranded RNA molecule is processed into smaller RNA molecules which are then processed into a silencing complex which results in inhibition of expression of the target gene, such as by cleavage of target gene mRNA. Generally, the RNAi molecule has 100 or more nucleotides, and more typically has 200 or more nucleotides. RNAi molecules can be provided by introduction and expression in a cell of a nucleic acid construct that results in transcription and production of the RNAi molecule. In one embodiment, RNA interference via expression of a nucleic acid that provides for micro RNA (miRNA) is contemplated within the scope of the invention. miRNAs are generally 19 to 23 nucleotide RNAs that have been processed from a longer precursor RNA comprising hairpin structures. In another embodiment, RNA interference via expression of a nucleic acid that provides for short interfering RNA (siRNA) is contemplated with the scope of the invention. siRNAs are generally 20 to 25 nucleotide RNAs having 3' overhangs and that have been processed from a longer precursor double-stranded RNA. Plants comprising and expressing RNAi molecules, including miRNAs and siRNAi can be grown from cells transformed with and/or incorporating polynucleotide molecules that provide for the RNAi molecules. Methods and materials for RNA interference have been described, for example, in U.S. Pat. Nos. 7,056,704; 7,078,196; 7,365,058; 7,232,086; 6,506,559; 7,282,564; and 7,538,095 and reviewed in Milhavet et al. (2003); Agrawal et al. (2003); Kusaba (2004); and Doran and Helliwell (2009). In one embodiment, an RNAi construct of the invention for inhibiting 4CL gene expression in a plant comprises all or a part of the nucleotide sequence of SEQ ID NO:4 or SEQ ID NO:5. In a specific embodiment, the RNAi molecules are selectively expressed in leaf cells and/or tissue of the plant, e.g., by use of a leaf-specific promoter.

Ribozyme technology can also be used to inhibit expression of a target gene involved in lignin biosynthesis in sugarcane. Ribozymes are a type of RNA that can be engineered to enzymatically cleave and inactivate other RNA targets in a specific, sequence-dependent fashion. By cleaving the target RNA, ribozymes inhibit translation, thus preventing the expression of the target gene. Ribozymes can be chemically synthesized in the laboratory and structurally modified to increase their stability and catalytic activity using methods known in the art. Ribozyme encoding nucleotide sequences can be introduced into plant cells and incorporated into the plant genome through gene-delivery mechanisms known in the art. Plants comprising and expressing the ribozyme encoding sequences can be grown from cells transformed with and/or incorporating the ribozyme encoding sequences. A ribozyme having specificity for 4CL can include one or more sequences complementary to the nucleotide sequence of at least a portion of one or more 4CL mRNA, and a sequence having known catalytic sequence responsible for mRNA cleavage (see U.S. Pat. No. 5,093,246 or Haselhoff et al. 1988). For example, a derivative of a Tetrahymena L-19 IVS RNA can be constructed in which the nucleotide sequence of the active site is complementary to the nucleotide sequence to be cleaved in the 4CL mRNA (see, e.g., U.S. Pat. No. 4,987,071; and U.S. Pat. No. 5,116,742). Alternatively, 4CL mRNA encoding a 4CL protein can be used to select a catalytic RNA having a specific ribonuclease activity from a pool of RNA molecules (see, e.g., Bartel et al. 1993). In one embodiment, the ribozymes are selectively expressed in leaf cells and/or tissue of the plant, e.g., by use of a leaf-specific promoter.

In addition to inhibition of target genes involved in lignin biosynthesis in sugarcane, the subject invention also contemplates mutations in target genes, or wherein mutant genes can be provided for in a plant cell wherein target gene expression or gene product levels or activity is decreased or inhibited. In one embodiment, a mutant 4CL gene is incorporated into the genome of a sugarcane plant wherein the mutant 4CL gene exhibits decreased or no expression of gene transcripts or translation thereof. In one embodiment, a mutation is introduced into a 4CL gene of a plant that results in decreased transcription of the 4CL gene, or decreased translation of mRNA, and/or that results in a protein exhibiting decreased enzymatic activity. In a specific embodiment, one or more mutations are introduced in the protein coding region of a 4CL gene. In another embodiment, a mutation is introduced in a 4CL gene upstream of the transcription start site and/or downstream of the transcription start site. In one embodiment, a mutation is introduced into or near a regulatory sequence of a 4CL gene, e.g., in a promoter sequence. The mutation may block or inhibit transcription of the 4CL gene sequence, e.g., by blocking or inhibiting binding of transcription factors or polymerase to the 4CL nucleic acid sequence. In one embodiment, a mutation in the 4CL gene is selectively introduced into leaf cells and/or leaf tissue of the plant. Mutations can also include one or more nucleotide or amino acid insertions, deletions, and/or substitutions that inhibit or decrease functional activity (e.g., enzymatic) of a 4CL polypeptide. Methods for creating and introducing mutations are known in the art. In one embodiment, the mutation is introduced into one or more wild-type 4CL genes in a plant. In another embodiment, a mutant 4CL gene replaces one or more wild-type 4CL genes in a plant. In one embodiment, mutant 4CL genes are selectively expressed in leaf cells and/ or tissue of the plant.

In addition to inhibition or suppression of target genes involved in lignin biosynthesis, the activity (e.g., enzymatic) of proteins encoded by the target genes of the invention can also be inhibited. In one embodiment, a nucleic acid encoding an antibody, or an antigen binding fragment thereof, that binds to and inhibits activity (e.g., enzymatic activity) of a protein can be incorporated and expressed in a cell of a sugarcane plant. A plant comprising and expressing a nucleic acid encoding an antibody, or an antigen binding fragment thereof, can be grown from cells transformed with and/or incorporating the nucleic acid. Methods for preparing an antibody that binds to and inhibits a specific target protein and for obtaining the nucleic acid that encodes the antibody are well known in the art. In one embodiment, the antibody is a monoclonal antibody, or an antigen binding fragment thereof. Antigen binding fragments include, but are not limited to, F(ab')$_2$, Fab', Fab, and Fv, and can be prepared using standard methods known in the art. The antibody can be derived from any animal capable of producing antibodies to a target protein epitope, and include, for example, human, primate, mouse, rat, goat, sheep, pig, and cow. In a specific embodiment, the antibody binds to a 4CL protein. In one embodiment, a 4CL gene encodes a 4CL polypeptide comprising an AMP-binding motif sequence (e.g., SEQ ID NO:34) and/or the signature motif sequence of SEQ ID NO:54. In a more specific embodiment, the 4CL protein is encoded by a 4CL-M gene, a 4CL-L gene, or a 4CL-N gene. In a specific embodiment, the 4CL-L gene comprises all or a part of the nucleotide sequence shown in SEQ ID NO:1, the 4CL-M gene comprises all or a part of the nucleotide sequence shown in SEQ ID NO:2, and the 4CL-N gene comprises all or a part of the nucleotide sequence shown in SEQ ID NO:3. In one embodiment, the 4CL-M, 4CL-L, and 4CL-N genes encode a polypeptide having the amino acid sequence shown in SEQ ID NOs:6, 7, and 8, respectively, or a fragment or variant thereof. In one embodiment, the antibody binds to a 4CL protein comprising the amino acid sequence of SEQ ID NO:6, 7, or 8, or a fragment or epitope thereof. In a specific embodiment, the nucleic acid encoding the antibody is selectively expressed in leaf tissue of the plant, e.g., by using a leaf specific promoter.

The activity (e.g., enzymatic) of proteins encoded by target genes involved in lignin biosynthesis can also be inhibited by expressing and/or contacting the target protein with an aptamer that binds to a specific target protein. Aptamers are oligonucleotides or peptides that can be selected for binding to a target molecule (see, for example, Ellington and Szostak (1990) and Hoppe-Seyler and Butz (2000) and U.S. Pat. Nos. 5,582,981; 5,270,163; 5,595,877; 5,817,785; 6,344,318; 6,933,116; 7,368,236; and 7,700,759). In one embodiment, a nucleic acid encoding an aptamer that binds to a protein involved in lignin biosynthesis is incorporated and expressed in a cell of a plant. A plant comprising and expressing a nucleic acid encoding an aptamer can be grown from cells transformed with and/or incorporating the nucleic acid. In one embodiment, the aptamer binds to and inhibits a 4CL protein. In one embodiment, a 4CL gene encodes a 4CL polypeptide comprising an AMP-binding motif sequence (e.g., SEQ ID NO:34) and/or the signature motif sequence of SEQ ID NO:54. In a specific embodiment, the 4CL protein is encoded by a 4CL-L, 4CL-M, or a 4CL-N gene of the invention. In a specific embodiment, the 4CL-L gene comprises all or a part of the nucleotide sequence shown in SEQ ID NO:1, the 4CL-M gene comprises all or a part of the nucleotide sequence shown in SEQ ID NO:2, and the 4CL-N gene comprises all or a part of the nucleotide sequence shown in SEQ ID NO:3. In one embodiment, the 4CL-M, 4CL-L, and 4CL-N genes encode a polypeptide having the amino acid sequence shown in SEQ ID NOs:6, 7, and 8, respectively, or a fragment or variant thereof. In one embodiment, the aptamer binds to a 4CL protein comprising the amino acid sequence of SEQ ID NO:6, 7, or 8, or a fragment or epitope thereof. In a specific embodiment, the nucleic acid encoding the aptamer is selectively expressed in leaf tissue of the plant, e.g., by using a leaf specific promoter.

The subject invention also concerns a sugarcane plant wherein lignin biosynthesis has been modulated (e.g., down-regulated). In one embodiment, the lignin biosynthesis is selectively down-regulated in leaf cells and/or tissue. In one embodiment, expression of one or more 4CL genes and/or or translation or activity of a protein encoded by a 4CL gene is inhibited or down-regulated in the sugarcane plant. In one embodiment, a 4CL gene encodes a 4CL polypeptide comprising an AMP-binding motif sequence (e.g., SEQ ID NO:34) and/or the signature motif sequence of SEQ ID NO:54. In one embodiment, the 4CL gene inhibited is 4CL-L, 4CL-M, or 4CL-N. In one embodiment, the 4CL-M, 4CL-L, and 4CL-N genes encode a polypeptide having the amino acid sequence shown in SEQ ID NO:6, 7, and 8, respectively, or a fragment or variant thereof. In a specific embodiment, the 4CL-L gene comprises all or a part of the nucleotide sequence shown in SEQ ID NO:1, the 4CL-M gene comprises all or a part of the nucleotide sequence shown in SEQ ID NO:2, and the 4CL-N gene comprises all or a part of the nucleotide sequence shown in SEQ ID NO:3. Sugarcane plants of the invention can have antisense, cosuppression, RNAi, or ribozyme nucleic acids that target one or more 4CL genes (e.g., 4CL-M, 4CL-N, and/or 4CL-L) incorporated into their genome. Sugarcane plants of the invention can have mutant 4CL genes in their genome wherein 4CL gene expression is inhibiting and/or wherein 4CL polypeptide has a mutation that inhibits or decreased functional activity (e.g., enzymatic) of the 4CL polypeptide. Sugarcane plants of the invention can also have incorporated into their genome nucleic acids that encode one or more antibodies (or antigen binding fragments thereof) and/or aptamers that bind to and inhibit enzymatic activity of a 4CL protein.

Optionally, the plants disclosed herein may further exhibit one or more agronomic traits that primarily are of benefit to a seed company, a grower, or a grain processor, for example, herbicide resistance, virus resistance, bacterial pathogen resistance, insect resistance, nematode resistance, and fungal resistance. See, e.g., U.S. Pat. Nos. 5,569,823; 5,304,730; 5,495,071; 6,329,504; and 6,337,431. Such trait may also be one that increases plant vigor or yield (including traits that allow a plant to grow at different temperatures, soil conditions and levels of sunlight and precipitation), or one that allows identification of a plant exhibiting a trait of interest (e.g., selectable marker gene, seed coat color, etc.). Various traits of interest, as well as methods for introducing these traits into a plant, are described, for example, in U.S. Pat. Nos. 5,569,823; 5,304,730; 5,495,071; 6,329,504; 6,337,431; 5,767,366; 5,928,937; 4,761,373; 5,013,659; 4,975,374; 5,162,602; 4,940,835; 4,769,061; 5,554,798; 5,879,903; 5,276,268; 5,561,236; 4,810,648; and 6,084,155; in European application No. 0242246; in U.S. Patent Application No. 20010016956; and on the worldwide web at www.lifesci.sussex.ac.uk/home/Neil_Crickmore/Bt/.

The subject invention also concerns sugarcane plant tissue and plant parts, including, but not limited to, plant cells, plant protoplasts, plant cell tissue cultures from which plants can be regenerated, plant calli, plant clumps, and plant cells that are intact in plants or parts of plants such as branches, kernels, ears, cobs, husks, root tips, anthers, seeds, roots, embryos, hypocotyls, cotyledons, pollen, ovules, anthers, shoots, stalks, stems, leaves, fruits, and flowers, from a sugarcane plant of the invention having modulated (e.g., down-regulated) lignin biosynthesis. In one embodiment, expression of one or more 4CL genes, or the gene product thereof, is inhibited or down-regulated in the plant tissue or plant cell. In one embodiment, the 4CL gene inhibited is 4CL-M, 4CL-L, or 4CL-N. In one embodiment, the 4CL-M, 4CL-L, and 4CL-N genes encode a polypeptide having the amino acid sequence shown in SEQ ID NO:6, 7, and 8, respectively, or a fragment or variant thereof. In a specific embodiment, the 4CL-L gene comprises all of a part of the nucleotide sequence shown in SEQ ID NO:1, the 4CL-M gene comprises all of a part of the nucleotide sequence shown in SEQ ID NO:2, and the 4CL-N gene comprises all of a part of the nucleotide sequence shown in SEQ ID NO:3.

The subject invention also concerns sugarcane cells or protoplasts having modulated or down-regulated lignin biosynthesis. In one embodiment, expression of one or more 4CL genes or translation or activity of a protein encoded by a 4CL gene is inhibited or down-regulated in the sugarcane cell or protoplast. In one embodiment, the 4CL gene inhibited is 4CL-M, 4CL-L, or 4CL-N. In one embodiment, the 4CL-M, 4CL-L, and 4CL-N genes encode a polypeptide having the amino acid sequence shown in SEQ ID NO:6, 7, and 8, respectively, or a fragment or variant thereof. In a specific embodiment, the 4CL-L gene comprises all of a part of the nucleotide sequence shown in SEQ ID NO:1, the 4CL-M gene comprises all of a part of the nucleotide sequence shown in SEQ ID NO:2, and the 4CL-N gene comprises all of a part of the nucleotide sequence shown in SEQ ID NO:3.

The subject invention also concerns methods for producing a sugarcane plant having decreased or down-regulated biosynthesis of lignin. In one embodiment, lignin biosynthesis is decreased or down-regulated in leaf cells and/or tissue of a sugarcane plant. In another embodiment, lignin biosynthesis is decreased or down-regulated in stem tissue of a sugarcane plant. In one embodiment, a method of the invention comprises suppressing or inhibiting the expression of one or more 4CL genes or inhibiting the translation or activity (e.g., enzymatic) of a protein encoded by a 4CL gene. In one embodiment, a 4CL gene encodes a 4CL polypeptide comprising an AMP-binding motif sequence (e.g., SEQ ID NO:34) and/or the signature motif sequence of SEQ ID NO:54. In one embodiment, the 4CL gene inhibited is 4CL-M, 4CL-L, or 4CL-N. In one embodiment, the 4CL-M, 4CL-L, and 4CL-N genes encode a polypeptide having the amino acid sequence shown in SEQ ID NO:6, 7, and 8, respectively, or a fragment or variant thereof. In a specific embodiment, the 4CL-L gene comprises all of a part of the nucleotide sequence shown in SEQ ID NO:1, the 4CL-M gene comprises all of a part of the nucleotide sequence shown in SEQ ID NO:2, and the 4CL-N gene comprises all of a part of the nucleotide sequence shown in SEQ ID NO:3. In one embodiment, the target gene expression is inhibited using antisense nucleic acid, cosuppression, RNA interference, or ribozymes. In another embodiment, the expression of the target gene is inhibited by mutation of the gene. In a still further embodiment, the activity of the protein encoded by a target gene is inhibited in the plant by expression of an antibody, or an antigen binding fragment thereof, and/or an aptamer that binds to the protein, or by providing mutations in the gene that inhibit translation of the mRNA of the gene into protein or that disrupt or inhibit function of the encoded protein (e.g., via changes in amino acid sequence). Nucleic acid constructs that provide for inhibition of target gene expression can be introduced into a plant genome, and transformed and transgenic plants prepared therefrom using standard methods and materials known in the art.

Polynucleotides useful in the present invention can be provided in an expression construct. Expression constructs of the invention generally include regulatory elements that are functional in the intended host cell in which the expression construct is to be expressed. Thus, a person of ordinary skill in the art can select regulatory elements for use in bacterial host cells, yeast host cells, plant host cells, insect host cells, mammalian host cells, and human host cells. Regulatory elements include promoters, transcription termination sequences, translation termination sequences, enhancers, and polyadenylation elements. As used herein, the term "expression construct" refers to a combination of nucleic acid sequences that provides for transcription of an operably linked nucleic acid sequence. As used herein, the term "operably linked" refers to a juxtaposition of the components described wherein the components are in a relationship that permits them to function in their intended manner. In general, operably linked components are in contiguous relation.

An expression construct of the invention can comprise a promoter sequence operably linked to a polynucleotide sequence of the invention. Promoters can be incorporated into a polynucleotide using standard techniques known in the art. Multiple copies of promoters or multiple promoters can be used in an expression construct of the invention. In a preferred embodiment, a promoter can be positioned about the same distance from the transcription start site in the expression construct as it is from the transcription start site in its natural genetic environment. Some variation in this distance is permitted without substantial decrease in promoter activity. A transcription start site is typically included in the expression construct.

If the expression construct is to be provided in or introduced into a plant cell, then plant viral promoters, such as, for example, a cauliflower mosaic virus (CaMV) 35S (including the enhanced CaMV 35S promoter (see, for example U.S. Pat. No. 5,106,739)) or a CaMV 19S promoter or a cassava vein mosaic can be used. Other promoters that can be used for expression constructs in plants include, for example, prolifera promoter, Ap3 promoter, heat shock promoters, T-DNA 1'- or 2'-promoter of *A. tumefaciens*, polygalacturonase promoter, chalcone synthase A (CHS-A) promoter from petunia, tobacco PR-1a promoter, ubiquitin promoter, actin promoter, alcA gene promoter, pin2 promoter (Xu et al., 1993), maize WipI promoter, maize trpA gene promoter (U.S. Pat. No. 5,625,136), maize CDPK gene promoter, and RUBISCO SSU promoter (U.S. Pat. No. 5,034,322) can also be used. Tissue-specific promoters, for example fruit-specific promoters, such as the E8 promoter of tomato (accession number: AF515784; Good et al. (1994)) can be used with the invention. Leaf-specific promoters that can be used in a nucleic acid construct of the invention include Cab1 promoter (Brusslan and Tobin, 1992), Cab19 promoter (Bassett et al., 2007), PPDK promoter (Matsuoka et al., 1993), and ribulose biphosphate carboxylase (RBCS) promoter (Matsuoka et al. (1994) and U.S. Pat. No. 7,723,575). Other plant leaf-specific promoters that can be used with an expression construct of the invention include, but are not limited to, the Act1 promoter (U.S. Published Application No. 20090031441), AS-1 promoter (U.S. Pat. No. 5,256,558), RBC-3A promoter (U.S. Pat. No. 5,023,179), the CaMV 35S promoter (Odell et al., 1985), the enhanced CaMV 35S promoter, the Figwort Mosaic Virus (FMV) promoter (Richins et al., 1987), the mannopine synthase (mas) promoter, the octopine synthase (ocs) promoter, or others such as the promoters from CaMV 19S (Lawton et al., 1987), nos (Ebert et al., 1987), Adh (Walker et al., 1987), sucrose synthase (Yang et al., 1990), a-tubulin, ubiquitin, actin (Wang et al., 1992), cab (Sullivan et al., 1989), PEPCase (Hudspeth et al., 1989) or those associated with the R gene complex (Chandler et al., 1989). See also published U.S. application 2007/006346 and Yamamoto et al. (1997); Kwon et al. (1994); Yamamoto et al. Fruit-specific promoters such as flower organ-specific promoters can be used with an expression construct of the present invention for expressing a polynucleotide of the invention in the flower organ of a plant. Examples of flower organ-specific promoters include any of the promoter sequences described in U.S. Pat.

Nos. 6,462,185; 5,639,948; and 5,589,610. Seed-specific promoters such as the promoter from a β-phaseolin gene (for example, of kidney bean) or a glycinin gene (for example, of soybean), and others, can also be used. Root-specific promoters, such as any of the promoter sequences described in U.S. Pat. No. 6,455,760 or U.S. Pat. No. 6,696,623, or in published U.S. patent application Nos. 20040078841; 20040067506; 20040019934; 20030177536; 20030084486; or 20040123349, can be used with an expression construct of the invention. Xylem-specific promoters include the cinnomate-4-hydroxylase (C4H) of rice. Constitutive promoters (such as the CaMV, ubiquitin, actin, or NOS promoter), developmentally-regulated promoters, and inducible promoters (such as those promoters than can be induced by heat, light, hormones, or chemicals) are also contemplated for use with polynucleotide expression constructs of the invention.

Methods for identifying and characterizing promoter regions in plant genomic DNA are known in the art and include, for example, those described in the following references: Jordano et al. (1989); Bustos et al. (1989); Green et al. (1988); Meier et al. (1991); and Zhang et al. (1996). Published U.S. application 2009/0199307 also describes methods for identifying tissue-specific promoters using differential display (see, e.g., U.S. Pat. No. 5,599,672). In differential display, mRNAs are compared from different tissue types. By identifying mRNA species which are present in only a particular tissue type, or set of tissue types, corresponding genes can be identified which are expressed in a tissue specific manner. RNA can be transcribed by reverse transcriptase to produce a cDNA, and the cDNA can be used to isolate clones containing the full-length genes. The cDNA can also be used to isolate homeologous or homologous promoters, enhancers or terminators from the respective gene using, for example, suppression PCR. See also U.S. Pat. No. 5,723,763.

Expression constructs of the invention may also optionally contain a transcription termination sequence, a translation termination sequence, a sequence encoding a signal peptide, and/or enhancer elements. Transcription termination regions can typically be obtained from the 3' untranslated region of a eukaryotic or viral gene sequence. Transcription termination sequences can be positioned downstream of a coding sequence to provide for efficient termination. A signal peptide sequence is a short amino acid sequence typically present at the amino terminus of a protein that is responsible for the relocation of an operably linked mature polypeptide to a wide range of post-translational cellular destinations, ranging from a specific organelle compartment to sites of protein action and the extracellular environment. Targeting gene products to an intended cellular and/or extracellular destination through the use of an operably linked signal peptide sequence is contemplated for use with the polypeptides of the invention. Classical enhancers are cis-acting elements that increase gene transcription and can also be included in the expression construct. Classical enhancer elements are known in the art, and include, but are not limited to, the CaMV 35S enhancer element, cytomegalovirus (CMV) early promoter enhancer element, and the SV40 enhancer element. Intron-mediated enhancer elements that enhance gene expression are also known in the art. These elements must be present within the transcribed region and are orientation dependent. Examples include the maize shrunken-1 enhancer element (Clancy and Hannah, 2002).

DNA sequences which direct polyadenylation of mRNA transcribed from the expression construct can also be included in the expression construct, and include, but are not limited to, a CaMV 35S, octopine synthase, or nopaline synthase signal. The expression constructs of the invention can also include a polynucleotide sequence that directs transposition of other genes, i.e., a transposon.

Expression constructs can also include one or more dominant selectable marker genes, including, for example, genes encoding antibiotic resistance for selecting transformed cells. Antibiotic-resistance genes can provide for resistance to one or more of the following antibiotics: hygromycin, kanamycin, bleomycin, G418, streptomycin, paromomycin, neomycin, and spectinomycin. Kanamycin resistance can be provided by neomycin phosphotransferase (NPT II). Other markers used for cell transformation screening include genes encoding β-glucuronidase (GUS), β-galactosidase, luciferase, nopaline synthase, chloramphenicol acetyltransferase (CAT), green fluorescence protein (GFP), or enhanced GFP (Yang et al. (1996)).

The subject invention also concerns polynucleotide vectors comprising a polynucleotide sequence of the invention that encodes a desired protein that is to be provided to a cell or cells provided with the bioreactor device of the invention. Unique restriction enzyme sites can be included at the 5' and 3' ends of an expression construct or polynucleotide of the invention to allow for insertion into a polynucleotide vector. As used herein, the term "vector" refers to any genetic element, including for example, plasmids, cosmids, chromosomes, phage, virus, and the like, which is capable of replication when associated with proper control elements and which can transfer polynucleotide sequences between cells. Vectors contain a nucleotide sequence that permits the vector to replicate in a selected host cell. A number of vectors are available for expression and/or cloning, and include, but are not limited to, pBR322, pUC series, M13 series, and pBLUESCRIPT vectors (Stratagene, La Jolla, Calif.).

Polynucleotides of the present invention can be composed of either RNA or DNA. Preferably, the polynucleotides are composed of DNA. The subject invention also encompasses those polynucleotides that are complementary in sequence to the polynucleotides disclosed herein.

Techniques for transforming plant cells with a gene are known in the art and include, for example, Agrobacterium infection, biolistic methods, electroporation, calcium chloride treatment, PEG-mediated transformation, etc. See, for example, U.S. Pat. Nos. 5,036,006; 5,591,616; 5,100,792; published U.S. Application No. 2006/0260011; and published PCT Application No. WO 93/07278 and WO 93/21335. U.S. Pat. No. 5,661,017 teaches methods and materials for transforming an algal cell with a heterologous polynucleotide. Transformed cells can be selected, redifferentiated, and grown into plants that contain and express a polynucleotide of the invention using standard methods known in the art. The seeds and other plant tissue and progeny of any transformed or transgenic plant cells or plants of the invention are also included within the scope of the present invention.

Polynucleotides and polypeptides of the subject invention can also be defined in terms of more particular identity and/or similarity ranges with those sequences exemplified herein. The sequence identity will typically be greater than 60%, preferably greater than 75%, more preferably greater than 80%, even more preferably greater than 90%, and can be greater than 95%. The identity and/or similarity of a sequence can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein. Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used. See NCBI/NIH website.

The subject invention also contemplates those polynucleotide molecules of the invention (and those encoding polypeptides of the invention) having sequences which are sufficiently homologous with the polynucleotide sequences encoding a polypeptide of the invention so as to permit hybridization with that sequence under standard stringent conditions and standard methods (Maniatis, T. et al., 1982). As used herein, "stringent" conditions for hybridization refers to conditions wherein hybridization is typically carried out overnight at 20-25 C below the melting temperature (Tm) of the DNA hybrid in 6×SSPE, 5×Denhardt's solution, 0.1% SDS, 0.1 mg/ml denatured DNA. The melting temperature is described by the following formula (Beltz, G. A. et al., 1983):

Tm=81.5 C+16.6 Log [Na+]+0.41 (% G+C)−0.61(% formamide)−600/length of duplex in base pairs.

Washes are typically carried out as follows:

(1) Twice at room temperature for 15 minutes in 1×SSPE, 0.1% SDS (low stringency wash).

(2) Once at Tm−20 C for 15 minutes in 0.2×SSPE, 0.1% SDS (moderate stringency wash).

As used herein, the terms "nucleic acid" and "polynucleotide sequence" refer to a deoxyribonucleotide or ribonucleotide polymer in either single- or double-stranded form, and unless otherwise limited, would encompass known analogs of natural nucleotides that can function in a similar manner as naturally-occurring nucleotides. The polynucleotide sequences include both the DNA strand sequence that is transcribed into RNA and the RNA sequence that is translated into protein. The polynucleotide sequences include both full-length sequences as well as shorter sequences derived from the full-length sequences. It is understood that a particular polynucleotide sequence includes the degenerate codons of the native sequence or sequences which may be introduced to provide codon preference in a specific host cell. The polynucleotide sequences falling within the scope of the subject invention further include sequences which specifically hybridize with the sequences coding for a polypeptide of the invention. The polynucleotide includes both the sense and antisense strands as either individual strands or in the duplex.

Polypeptides having substitution of amino acids other than those specifically exemplified in the subject polypeptides are also contemplated within the scope of the present invention. For example, non-natural amino acids can be substituted for the amino acids of a polypeptide of the invention, so long as the polypeptide having substituted amino acids retains substantially the same activity as the polypeptide in which amino acids have not been substituted. Examples of non-natural amino acids include, but are not limited to, ornithine, citrulline, hydroxyproline, homoserine, phenylglycine, taurine, iodotyrosine, 2,4-diaminobutyric acid, a-amino isobutyric acid, 4-aminobutyric acid, 2-amino butyric acid, γ-amino butyric acid, e-amino hexanoic acid, 6-amino hexanoic acid, 2-amino isobutyric acid, 3-amino propionic acid, norleucine, norvaline, sarcosine, homocitrulline, cysteic acid, t-butylglycine, t-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Non-natural amino acids also include amino acids having derivatized side groups. Furthermore, any of the amino acids in the protein can be of the D (dextrorotary) form or L (levorotary) form.

Amino acids can be generally categorized in the following classes: non-polar, uncharged polar, basic, and acidic. Conservative substitutions whereby a polypeptide having an amino acid of one class is replaced with another amino acid of the same class fall within the scope of the subject invention so long as the polypeptide having the substitution still retains substantially the same biological activity as a polypeptide that does not have the substitution. Nonpolar amino acids include Ala, Val, Leu, Ile, Pro, Met, Phe, and Trp. Uncharged polar amino acids include Gly, Ser, Thr, Cys, Tyr, Asn, and Gln. Acidic amino acids include Asp and Glu. Basic amino acids include Lys, Arg, and His.

Once a nucleic acid sequence of the present invention has been incorporated into an expression system, it can be transformed into a plant cell. The word "plant" refers to any plant, particularly to seed plant, and "plant cell" is a structural and physiological unit of the plant, which comprises a cell wall but may also refer to a protoplast. The plant cell may be in form of an isolated single cell or a cultured cell, or as a part of higher organized unit such as, for example, a plant tissue, or a plant organ. The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms."

Examples of methods of transformation of plants and plant cells include *Agrobacterium*-mediated transformation (Deblaere et al. (1987)) and particle bombardment technology (Klein et al. (1987); U.S. Pat. No. 4,945,050). Whole plants may be regenerated from transgenic cells by methods well known to the skilled artisan (see, for example, Fromm et al. (1990)).

The expression constructs of the present invention can be introduced into the plant cell in a number of art-recognized ways. The term "introducing" in the context of a polynucleotide, for example, a nucleotide encoding an enzyme disclosed herein, is intended to mean presenting to the plant the polynucleotide in such a manner that the polynucleotide gains access to the interior of a cell of the plant. Where more than one polynucleotide is to be introduced, these polynucleotides can be assembled as part of a single nucleotide construct, or as separate nucleotide constructs, and can be located on the same or different transformation vectors.

Accordingly, these polynucleotides can be introduced into the host cell of interest in a single transformation event, in separate transformation events, or, for example, in plants, as part of a breeding protocol. The methods of the invention do not depend on a particular method for introducing one or more polynucleotides into a plant, only that the polynucleotide(s) gains access to the interior of at least one cell of the plant. Methods for introducing polynucleotides into plants are known in the art and include, but are not limited to, transient transformation methods, stable transformation methods, and virus-mediated methods.

"Transient transformation" in the context of a polynucleotide is intended to mean that a polynucleotide is introduced into the plant and does not integrate into the genome of the plant.

By "stably introducing" or "stably introduced" in the context of a polynucleotide introduced into a plant is intended to mean that the introduced polynucleotide is stably incorporated into the plant genome, and thus the plant is stably transformed with the polynucleotide.

"Stable transformation" or "stably transformed" is intended to mean that a polynucleotide, for example, a nucleotide construct described herein, introduced into a plant integrates into the genome of the plant and is capable of being inherited by the progeny thereof, more particularly, by the progeny of multiple successive generations.

Numerous transformation vectors available for plant transformation are known to those of ordinary skill in the plant transformation arts, and the genes pertinent to this invention can be used in conjunction with any such vectors. The selection of vector will depend upon the preferred transformation technique and the target species for transformation. For certain target species, different antibiotic or herbicide selection markers may be preferred.

Methods for regeneration of transformed plants are well known in the art. For example, Ti plasmid vectors have been utilized for the delivery of foreign DNA, as well as direct DNA uptake, liposomes, electroporation, microinjection, and microprojectiles. In addition, bacteria from the genus *Agrobacterium* can be utilized to transform plant cells. Below are descriptions of representative techniques for transforming both dicotyledonous and monocotyledonous plants, as well as a representative plastid transformation technique.

Many vectors are available for transformation using *Agrobacterium tumefaciens*. These typically carry at least one T-DNA border sequence and include vectors such as pBIN19 (Bevan (1984)). For the construction of vectors useful in *Agrobacterium* transformation, see, for example, U.S. Patent Application Publication No. 2006/0260011.

Transformation without the use of *Agrobacterium tumefaciens* circumvents the requirement for T-DNA sequences in the chosen transformation vector and consequently vectors lacking these sequences can also be utilized. Transformation techniques that do not rely on *Agrobacterium* include, but are not limited to, transformation via particle bombardment, protoplast uptake (e.g., PEG and electroporation) and microinjection. The choice of vector depends largely on the preferred selection for the species being transformed. For the construction of such vectors, see, for example, U.S. Published Application No. 2006/0260011.

Transformation techniques for dicotyledons are well known in the art and include *Agrobacterium*-based techniques and techniques that do not require *Agrobacterium*. Non-*Agrobacterium* techniques involve the uptake of exogenous genetic material directly by protoplasts or cells and can be accomplished, for example, by PEG or electroporation mediated uptake, particle bombardment-mediated delivery, or microinjection. Examples of these techniques are described by Paszkowski et al. (1984), Potrykus et al. (1985), Reich et al. (1986), and Klein et al. (1987). In each case the transformed cells are regenerated to whole plants using standard techniques known in the art.

*Agrobacterium*-mediated transformation is a preferred technique for transformation of dicotyledons because of its high efficiency of transformation and its broad utility with many different species. *Agrobacterium* transformation typically involves the transfer of the binary vector carrying the foreign DNA of interest to an appropriate *Agrobacterium* strain which may depend of the complement of vir genes carried by the host *Agrobacterium* strain either on a co-resident Ti plasmid or chromosomally (Uknes et al. (1993)). The transfer of the recombinant binary vector to *Agrobacterium* is accomplished by a triparental mating procedure using *E. coli* carrying the recombinant binary vector, a helper *E. coli* strain which carries a plasmid that is able to mobilize the recombinant binary vector to the target *Agrobacterium* strain. Alternatively, the recombinant binary vector can be transferred to *Agrobacterium* by DNA transformation (Hofgen and Willmitzer (1988)).

Transformation of the target plant species by recombinant *Agrobacterium* usually involves co-cultivation of the *Agrobacterium* with explants from the plant and follows protocols well known in the art. Transformed tissue is regenerated on selectable medium carrying the antibiotic or herbicide resistance marker present between the binary plasmid T-DNA borders.

Another approach to transforming plant cells with a gene involves propelling inert or biologically active particles at plant tissues and cells. This technique is disclosed in U.S. Pat. Nos. 4,945,050, 5,036,006, and 5,100,792. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium or a bacteriophage, each containing DNA sought to be introduced) can also be propelled into plant cell tissue.

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e., co-transformation) and both of these techniques are suitable for use with this invention. Co-transformation may have the advantage of avoiding complete vector construction and of generating transgenic plants with unlinked loci for the gene of interest and the selectable marker, enabling the removal of the selectable marker in subsequent generations, should this be regarded desirable.

Patent Applications EP 0292435, EP 0392225, and WO 93/07278 describe techniques for the preparation of callus and protoplasts from an elite inbred line of maize, transformation of protoplasts using PEG or electroporation, and the regeneration of maize plants from transformed protoplasts. Gordon-Kamm et al. (1990) and Fromm et al. (1990) have published techniques for transformation of A188-derived maize line using particle bombardment. Furthermore, WO 93/07278 and Koziel et al. (1993) describe techniques for the transformation of elite inbred lines of maize by particle bombardment. This technique utilizes immature maize embryos of 1.5-2.5 mm length excised from a maize ear 14-15 days after pollination and a PDS-1000He Biolistics device for bombardment.

The plants obtained via transformation with a nucleic acid sequence of the present invention can be any of a wide variety of plant species, including those of monocots and dicots. The expression of a gene of the present invention in combination with other characteristics important for production and quality can be incorporated into plant lines through breeding. The polynucleotides of the invention disclosed herein may also be incorporated into or maintained in plant lines through breeding or through common genetic engineering technologies. Breeding approaches and techniques are known in the art. See, for example, Welsh (1981); Wood (1983); Mayo (1987); Singh (1986); and Wricke and Weber (1986).

The genetic properties engineered into the transgenic seeds and plants described above are passed on by sexual reproduction or vegetative growth and can thus be maintained and propagated in progeny plants. Generally, maintenance and propagation make use of known agricultural methods developed to fit specific purposes such as tilling, sowing or harvesting.

The relevant techniques are well known in the art and include but are not limited to hybridization, inbreeding, backcross breeding, multi-line breeding, dihaploid inbreeding, variety blend, interspecific hybridization, aneuploid techniques, etc. Hybridization techniques also include the sterilization of plants to yield male or female sterile plants by mechanical, genetic (including transgenic), chemical, or biochemical means.

For the purposes of the present invention, "sugarcane" will refer to any *Saccharum* plant or hybrid. Sugarcane plants included within the scope of the invention include, for example, *Saccharum arundinaceum, Saccharum bengalense, Saccharum edule, Saccharum officinarum, Saccharum procerum, Saccharum ravennae, Saccharum robustum, Saccharum sinense*, and *Saccharum spontaneum*. Sugarcane plants of the invention can be inbred lines or hybrids. Hybrid plants include those generated by the traditional *Saccharum spontaneum* by *Saccharum officianarum* hybrid material that makes up all current commercial sugarcane and energycane germplasm, and any other hybrids that are produced by crossing sugarcane with closely or distantly related species. Examples of other species that sugarcane can be crossed with to generate hybrid plants or new varieties of sugarcane include *Miscanthus, Erianthus*, and *Sorghum*.

"Isolated" means altered "by the hand of man" from its natural state, i.e., if it occurs in nature, it has been changed or removed from its original environment, or both. For example, a naturally occurring polynucleotide or a polypeptide naturally present in a living animal in its natural state is not "isolated," but the same polynucleotide or polypeptide separated from the coexisting materials of its natural state is "isolated," as the term is employed herein. For example, with respect to polynucleotides, the term isolated means that it is separated from the chromosome and cell in which it naturally occurs. A sequence is also isolated if separated from the chromosome and cell in which it naturally occurs in but inserted into a genetic context, chromosome, or cell in which it does not naturally occur.

As used herein the term "transgenic" refers to plants that include an exogenous polynucleotide (e.g., gene) that is stably maintained in the transformed plant and is stably inherited by progeny in successive generations. The term "transgenic plant" can refer either to the initially transformed plant or to the progeny of the initially transformed plant. Techniques for transforming plants, plant cells or plant tissues can include, but are not limited to, transformation with DNA employing *A. tumefaciens* or *A. rhizogenes* as the transforming agent, electroporation, DNA injection, microprojectile bombardment, and particle acceleration. See, for example, EP 295959 and EP 138341. As used herein, the terms "plant material" or "plant part" includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, tubers, rhizomes and the like.

TABLE 1

| Letter Symbol | Amino Acid | Letter Symbol | Amino Acid |
|---|---|---|---|
| A | Alanine | M | Methionine |
| B | Asparagine or aspartic acid | N | Asparagine |
| C | Cysteine | P | Proline |
| D | Aspartic Acid | Q | Glutamine |
| E | Glutamic Acid | R | Arginine |
| F | Phenylalanine | S | Serine |
| G | Glycine | T | Threonine |
| H | Histidine | V | Valine |
| I | Isoleucine | W | Tryptophan |
| K | Lysine | Y | Tyrosine |
| L | Leucine | Z | Glutamine or glutamic acid |

Materials and Methods

Plant Materials.

Field grown mature sugarcane (*Saccharum* spp. Hybrid) var. CP88-1762 in addition to green-house grown immature CP88-1762 and L 79-1002 were used in expression analysis.

RNA Extraction, Isolation of Genes, and RT-PCR.

Total RNA was isolated using TRIzol regent (Invitrogen) from leaves, stems, nodes, and roots. First-strand cDNAs were synthesized from 1 ug of total RNA using a cDNA synthesis kit (Bio-Rad).

Isolation of 4CL from Sugarcane

Sc4CL-L

Partial 4CL-L was obtained by RACE (Rapid Amplification of cDNA Ends) technique. RACE was performed using SMART RACE kit (Clontech) according to the manufacturer's instructions. 5'- and 3'-RACE ready cDNA pools were synthesized from 2 ug of total RNA, and these pools were used as the PCR template. Primary (LPF: 5'-CGTTGCCTGT-GAAGTCCGGCGC-3' (SEQ ID NO:17)) and nested (LNF: 5'-CCACGGCGAAGACCATCGACTCG-3' (SEQ ID NO:18)) gene specific primer designed based on the partial genomic DNA sequence of 4CL-L. Primary PCR was performed with the LPF and manufacturer provided Universal Primer Mix (UPM). The PCR conditions consisted of 25 cycles of 94° C. for 30 sec, 68° C. for 60 sec and 72° C. for 180 sec. The primary PCR products were diluted from one to 50 and used as templates for the secondary PCR with the LNF and manufacturer provided Nested Universal Primer (NUP). The second PCR was performed under 20 cycles of the same conditions as the first PCR. The product of 3'-RACE PCR product were cloned into the pCR2.1 TOPO vector (Invitrogen) and sequenced.

Sc4CL-M

4CL-M was isolated by cDNA library screening. Leaf, internode, node and immature leaf roll of sugarcane (*Saccharum* spp. Hybrid) var. CP88-1762 were harvested from field grown plants (Belle Grade and Citra, Fla.). Root and emerging shoot were collected from hydroponic solution grown plants. Total RNA was extracted from each tissue using Trizol (Invitrogen) and Total RNA from each sample was mixed in the same proportion. mRNA was purified from mixed total RNA using Oligotex mRNA Mini Kit (Qiagen). cDNA was synthesized form 5.9 ug of mRNA and ligated to the Uni-ZAP XR vector using cDNA Synthesis Kit and ZAP-cDNA Synthesis Kit (Stratagene). Packing and amplification were performed using ZAP-cDNA Gigapack III Gold Cloning Kit according to the manufacturer's instructions (Stratagene). For screening, 447 bp partial 4CLM specific probe was generated by PCR and labeled with $^{32}$P-dCTP, using a random primer kit (Promega). Approximately $2.0 \times 10^5$ of recombinant phages were screened, and one positive phages was isolated. To obtain the cDNA containing pBluscript phagemid, in vivo excision was performed, and the isolate was sequence.

Sc4CL-N

4CL-N was PCR-amplified from cDNA with gene-specific primer deduced from the sugarcane EST sequences. '4-coumarate coenzyme A ligase' were used as subjects for keyword search against the DFCI *Saccharum officinarum* Gene Index (SoGI; see: compbio.dfci.harvard.edu/cgi-bin/tgi/gireport.pl?gudb=s_*officinarum*). One Tentative Consensus (TC) sequences, TC88322, which had the complete open reading frame, was detected and used for primer design. Forward primer (4CL 1 F: 5'-ATGGGTTCCGTGGACACG-GCGGTCGCG-3' (SEQ ID NO:19)) and reverse primer (4CL1R: 5'-TCAGTGAACACCGGCGGCGAGCCTGG-3' (SEQ ID NO:20)) were designed from start and stop codon regions, respectively. Total RNA was isolated from leaf, internode, node, and shoot using Trizol according to the manufacturer's instructions (Invitrogen), and cDNA synthesis was performed using the iScript cDNA synthesis kit (Bio-rad). 200 ng of cDNA mixture from each tissue was used as the PCR template. PCR was carried out using TaKaRa LA taq polymerase (Takara BIO Inc.), and the PCR conditions consisted of 35 cycles of 95° C. for 45 sec, 56° C. for 45 sec and 72° C. for 120 sec. PCR product of two independent amplifications were cloned into pCR2.1 TOPO vector (Invitrogen) and sequenced.

Construction of the Sc4CL RNAi Suppression Constructs

Based on the sequencing information for Sc4CL-L (SEQ ID NO:1) and Sc4CL-M (SEQ ID NO:2), specific primers were designed to amplify 200 bp region named exon 2 and exon 1, respectively. Sequence correspondent to two restriction enzymes, EcoRI and XbaI, were added to the forward primer and for the reverse primer sequence specific to EcoRV restriction enzyme was added to facilitate subcloning. The plasmid pWF BgH4CL_RNAi consist of two inverted repeats separated by Bg4CL native intron and the transcription terminator CaMV35SpolyA was used for the construction Sc4CL interference constructs. In two separate and sequential subcloning steps the inverted repeats in the plasmid pWF BgH4CL_RNAi were replaced by Sc4CL specific sequences. Then the rice C4H promoter was subcloned and the two for Sc4CL-Li and Sc4CL-Mi were generated (SEQ ID NO:4 and SEQ ID NO:5).

Generation of 4CLi Sugarcane Lines

Transverse sections of immature leaf rolls of sugarcane (*Saccharum* spp. Hybrid) var. CP88-1762, were used to induce callus on modified MS basal medium (CI-3), supplemented with 20 g/L sucrose and 13.6 uM 2,4-D, pH adjusted to 5.8 (Chengalrayan and Gallo-Meagher, 2001). After callus induction, biolistic gene transfer was carried out using the PDS-1000/He biolistic particle delivery system. (Bio-Rad) as described previously (James et al., 2008). Selection was performed with geneticin as described (Chengalrayan and Gallo-Meagher, 2001) with minor modification where further selection was conducted for the regenerated plants as they subcultured at MS basal medium containing paromomycin (30 mg/L) at the rooting stage for 4 biweekly subcultures. Selected plants that developed healthy roots were transferred to the soil and were transferred to the greenhouse.

Characterization of Transgenic Lines

Transgenic sugarcane plants were confirmed by NPTII-ELISA and PCR following selection and regeneration of plants. Total protein extraction and NPTII-ELISA were performed using Pathoscreen nptII ELISA kit (Agdia) according to the manufacturer's instruction. Genomic DNA was extracted from the expanding leaf of each regenerated plant using DNeasy Plant Mini kit (Qiagen). 75 ng of genomic DNA was used as the PCR template. To detect each expression construct, primers were designed from each gene and promoter regions as follows: For the Sc4CL-Mi and Sc4CL-Li RNAi constructs, 4CL SF (5'-CATCAAGGGTACGG-GATGAC-3' (SEQ ID NO:21)) and OSPRO SR (5'-GTAGC-CTGCTAGTCTTCTCTCTCATT-3' (SEQ ID NO:22)). PCR was performed using iTaq polymerase (Bio-Rad) as following conditions: 35 cycles of 95° C. for 30 sec, 58° C. for 30 sec, and 72° C. for 60 sec. For Northern blot analysis, total RNA was extracted from the $3^{rd}$ leaf of the plant for the 4CL-Li lines and from a side-tiller around 25 cm long for the 4CL-Mi lines (Sambrook et at., 1989). Samples from the wild type plants growing under the same conditions as the transgenic plants were collected at the same developmental stage. Northern hybridization was carried out with a radio-labeled probe from the open reading frame of the targeted 4CL gene following electrophoresis and transfer of 20 ug total RNA.

Total lignin was quantified in transgenic sugarcane and non-transgenic (wild type) sugarcane plants using Klason procedure form senescent leaves and internodes of 4CL-Li lines and 4CL-Mi lines, respectively as described by Browning (1967) with minor modifications (Yoshihara et al., 1984). Briefly, after grinding the dried samples (0.5- to 1-mm screen), samples were extracted with 50% warm ethanol to remove soluble sugars and dried. Then 0.1 g dry cell wall samples were subjected to hydrolysis using 12M $H_2SO_4$ at 30° C. for 2 h. The contents were diluted with distilled water and autoclaved for 1 h. After autoclaving the insoluble materials (lignin and ash) were collected by filtrations and weighed. Then the lignin was burned at 500° C. for 5 h. Following this step the ash was weighed and the lignin was calculated as the difference in the weight before and after burning.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

EXAMPLE 1

Isolation of Sc4CL Genes

The sequences of two full-length and one partial sugarcane 4CL genes were isolated and characterized in this study. The cDNA sequences of Sc4CL-N and Sc4CL-M have an open reading frame of 1665 and 1728 nucleotides encoding a 555 and a 576 amino acid protein, respectively. The partial Sc4CL-L cDNA sequence is 616 bp long that includes the 3'UTR, and 141 amino acid residue of the open reading frame. A pairwise comparison between the Sc4CL-N and Sc4CL-M showed 59% similarity. Sc4CL-N is the most closely related to previously identified 4CLs, showing 96% and 86% similarities with Sb4CL-like 1 from *Sorghum bicolor* and Os4CL3 from *Oryza sativa*, respectively, whereas Sc4CL-M shares lower similarities with Sb4CL-like 1 and Os4CL3, but it shows higher similarities with Sb4CL-like 2 and Os4CL3 (96% and 83%, respectively). A comparison of the deduced amino acid sequences between the Sc4CLs and the At4CLs from *Arabidopsis thaliana* showed similarities ranging from 60% to 63% (Table 2).

Alignment (performed by CLUSTALW (see: npsa-pbil.ibcp.fr/cgi-bin/npsa_automat.pl?page=/NPSA/npsa_clustalw.html) using the default parameters) between Sc4CLs and other 4CLs, Ptd4CLs from Poplar and At4CLs from *Arabidopsis thaliana*, which were functionally characterized, shows a conserved AMP-binding motif (see, for example, SEQ ID NOs:34, 35, 36, 37, 38, 39, 40, 41, 42, and 43) and the signature motif 'GEICIRG' (SEQ ID NO:54), which is thought to be a substrate recognition site (Ehlting et al. 2001). Phylogenetic analysis showed 4CL gene family members in poaceae family can be grouped into two major phylogenetically related clusters, Group I and Group II. Sc4CL-N and Sc4CL-M were grouped into plant 4CL Group I and Group II, respectively. Group I includes *Zea mays* 4CL2, *Oryza sativa* 4CL1, *Arabidopsis thaliana* 4CL1, *Lolium perenne* 4CL2, Poplar 4CL3, Poplar 4CL1, Poplar 4CL2, *Arabidopsis thaliana* 4CL2, *Sorghum bicolor* 04g005210, *Zea mays* L00542166, and *Zea mays* ACF84437. Group II includes *Oryza sativa* 4CL2, *Sorghum bicolor* 04g031010, *Arabidopsis thaliana* 4CL3, *Lolium perenne* 4CL1, Poplar 4CL4, *Arabidopsis thaliana* 4CL4, *Oryza sativa* 4CL3, *Oryza sativa* 4CL5, *Sorghum bicolor* 10g026130, *Lolium perenne* 4CL3, and *Oryza sativa* 4CL4.

individual 4CL gene products in lignin biosynthesis, 4CL down-regulated sugarcane was generated utilizing the sequence information for Sc4CL, two RNA suppression constructs were generated (SEQ ID NO:4 and SEQ ID NO:5), targeting different regions of Sc4CL-L, and Sc4CL-M genes, under the control of a xylem specific promoter, the rice cinnamate-4-hydroxylase (C4H) promoter (Fouad and Altpeter, unpublished) and CaMV 35S polyA signal. The generated suppression cassettes were co-introduced, individually or together, into embryogenic sugarcane callus with selectable nptII gene under regulatory control of the strong constitutive maize ubiquitin promoter with first intron (pUbi) and 35S 3'UTR using biolistic gene transfer. The selection of transgenic events was conducted using the nptII/geneticin and paromomycin selection system where several transgenic lines were generated.

A total of 88 bombardments were conducted utilizing the two generated suppression cassettes and 160 plants were regenerated following callus selection. 152 indepentent plants showed NPTII expression using Pathoscreen nptII ELISA kit (Table 4). The presence of the 4CL-RNAi suppression cassette in the genomic DNA of the transgenic plants was confirmed using PCR (Table 4).

TABLE 2

The percentage similarities between 4CL amino acid sequences

|  | Sc4CL1 | Sc4CL2 | Sb4CL-like 1 | Sb4CL-like 2 | Os4CL2 | Os4CL3 | At4CL1 | At4CL2 |
|---|---|---|---|---|---|---|---|---|
| Sc4CL1 |  | 59 | 96 | 60 | 59 | 86 | 61 | 60 |
| Sc4CL2 |  |  | 58 | 96 | 83 | 59 | 61 | 62 |
| Sb4CL-like 1 |  |  |  | 60 | 59 | 87 | 62 | 61 |
| Sb4CL-like 2 |  |  |  |  | 85 | 61 | 61 | 63 |
| Os4CL2 |  |  |  |  |  | 59 | 60 | 60 |
| Os4CL3 |  |  |  |  |  |  | 62 | 62 |
| At4CL1 |  |  |  |  |  |  |  | 80 |
| At4CL2 |  |  |  |  |  |  |  |  |

Sc: Sugarcane,
Sb: *Sorghum bicolor*,
Os: *Oryza sativa*,
At: *Arabidopsis thaliana*

EXAMPLE 2

Expression Profile of the 4CL Genes

Sugarcane 4CL-M was predominantly expressed in stems, while Sc4CL-L was predominantly expressed in leaves (Table 3). This suggests that expression of different 4CL genes can be regulated in a tissue specific manner and offers the opportunity to suppress lignin in specific tissues.

TABLE 3

Tissue and cultivar-specific expression of Sc4CL genes

| Sugarcane | L79-1002 | | | CP88-1762 | | |
|---|---|---|---|---|---|---|
| cultivar | Leaf | Stem | Node | Leaf | Stem | Node |
| 4CL-M | − | + | − | + | ++ | − |
| 4CL-L | ++ | − | − | +++ | ++ | − |

L, S, and N indicate leaves, stems, and nodes; respectively.

EXAMPLE 3

Generation of 4CL Down-Regulated Sugarcane

RNAi is a powerful tool for crop improvement and to study gene function. Thus, to investigate physiological roles of The expression analysis for sugarcane 4CL in the transgenic sugarcane plants indicated suppression of the Sc4CL-L (Table 5) and Sc4CL-M gene (Table 6) in several transgenic sugarcane plants compared to non-transgenic (WT) sugarcane.

TABLE 4

Summary of transgenic 4CLi sugarcane

| Construct(s) | Plants regenerated following selection | NPT II ELISA (positive/tested) | PCR for 4CL (positive/tested) | 4CL Northern Suppressed/tested |
|---|---|---|---|---|
| C4H-4CL-L | 13 | 11/13 | 10/13 | 8/9 |
| C4H-4CL-M | 66 | 65/66 | NA | 11/20 |
| Total | 79 | 76/79 | | |

NA = Not analyzed

TABLE 5

Expression levels of 4CL-L gene and lignin content in senescent leaves of sugarcane 4CL-Li transgenic plants

| Lines | 4CL-L expression[1] (percentage) | Klason Lignin (percentage DW) |
|---|---|---|
| WT | 100 | 24.225[2] |
| 3 | 20 | 23.9 |
| 6 | 0-10 | 23.25[2] |
| 9 | 0-10 | 24.3 |
| 14-2A | 0-10 | 21.267[2] |

[1]Expression based on RNA blot analysis relative to the WT expression (100%)
[2]Mean of two to three biological replicates, generated by analyzing two to three individual plants of the same genotype.

TABLE 6

Expression levels of 4CL-M gene and lignin content in immature internodes of sugarcane 4CL-Mi transgenic plants

| Lines | 4CL-M expression[1] (percentage) | Klason Lignin (percentage DW) |
|---|---|---|
| WT | 100 | 15.73[2] |
| 5b-A1 | 10 | 14.45 |
| 4a | 5 | 14.45[2] |
| 7c-B2 | 30 | 15.25 |

[1]Expression based on RNA blot analysis relative to the WT expression (100%)
[2]Mean of two biological replicates, generated by analyzing two individual plants of the same genotype.

EXAMPLE 4

Generation Sugarcane with Reduced Lignin

Total lignin was quantified in senescent leaves of 4CL-Li transgenic plants and non-transgenic sugarcane using the Klason procedure form lines following the standard protocol. As shown in Table 5, Klason lignin was about 23.6% in senescent leaves of the non-transgenic sugarcane plants. In contrast, transgenic line 14-2A with suppression of the 4CL-L gene had an average of 21% Klason lignin in senescent leaves (Table 5), indicating 11% reduction in total lignin through 4CL-L suppression. Lignin was also analyzed in the immature internodes of 4CL-Mi lines (Table 6) and wild type plants. Line 4a exhibited about 8% reductions in total lignin compared to wild type plants. Lines 5b-A1 also showed a similar level of lignin reduction (Table 6). Greater lignin reduction in these transgenic 4CL-Mi plants is expected in mature internodes, where lignin content of non-transgenic plants increase to more than 20%.

EXAMPLE 5

Quantitative PCR Analysis of 4CLM Expression

Quantitative real-time RT-PCR analysis confirmed 4CLM suppression in several transgenic lines. Table 7 shows the relative expression ratio of 4CLM gene to the reference gene (Sugarcane GAPDH). Table 7 shows strong suppression of the 4CLM transcript in transgenic sugarcane lines, including lines 4A and 5BA1. Developmentally matching side tillers were harvested and total RNA was extracted from the first internode. 4CLM gene specific primers were designed from 3'UTR. All reactions were performed in parallel and each reaction was carried out in triplicate. Standard errors were calculated using Q-gene software.

TABLE 7

Quantitative PCR analysis of 4CLM expression

| | Plant line | Mean normalized expression of 4CLM | standard error |
|---|---|---|---|
| wild-type | WT1 | 0.158183469 | 0.030398171 |
| | WT2 | 0.085389181 | 0.023563549 |
| | WT3 | 0.068677827 | 0.008813278 |
| | WT4 | 0.095779515 | 0.0036248 |
| 4CLM RNAi transgenic lines | 4A | 0.002506449 | 0.000235822 |
| | 5BA1 | 0.00765043 | 0.001561502 |
| | 2D301 | 0.030256393 | 0.006236083 |
| | D303 | 0.032826712 | 0.007700117 |
| | 3D101 | 0.042700512 | 0.000739096 |
| | 2E301 | 0.051611828 | 0.013784677 |
| | 2F302 | 0.067672462 | 0.013071891 |
| | F302 | 0.106257424 | 0.001041556 |
| | 2D101 | 0.10903124 | 0.022234267 |
| | 2E201 | 0.147694218 | 0.022925399 |
| | 2E401 | 0.171012655 | 0.009865807 |

EXAMPLE 6

Estimates of Evolutionary Divergence among Plant 4CL Genes

The number of amino acid substitutions per site from analysis between Sugarcane 4CLs and other plant 4CLs is shown in Table 8. All results are based on the pairwise analysis of amino acid sequences. Analyses were conducted using the Poisson correction method in MEGA4 (Zuckerkandl and Pauling (1965); Tamura et al. (2007)). All positions containing gaps and missing data were eliminated from the dataset (Complete deletion option). There were a total of 513 positions in the final dataset.

TABLE 8

Estimates of evolutionary divergence among plant 4CLs.

| | Sc4CL1 | Sc4CLM | Sb 04g005210 | Sb 04g031010 | Sb 10g026130 | Zm LOC542166 |
|---|---|---|---|---|---|---|
| Sc4CL1 | | | | | | |
| Sc4CLM | 0.47 | | | | | |
| Sb_04g005210 | 0.03 | 0.47 | | | | |
| Sb_04g031010 | 0.45 | 0.03 | 0.45 | | | |
| Sb_10g026130 | 0.16 | 0.44 | 0.15 | 0.43 | | |
| Zm_LOC542166 | 0.07 | 0.46 | 0.06 | 0.44 | 0.18 | |
| At4CL1 | 0.42 | 0.41 | 0.42 | 0.41 | 0.38 | 0.43 |
| At4CL2 | 0.43 | 0.40 | 0.43 | 0.39 | 0.39 | 0.43 |
| At4CL3 | 0.46 | 0.37 | 0.46 | 0.35 | 0.47 | 0.46 |
| At4CL4 | 0.55 | 0.53 | 0.54 | 0.52 | 0.52 | 0.55 |
| Lp4CL1 | 0.48 | 0.16 | 0.48 | 0.14 | 0.45 | 0.47 |

TABLE 8-continued

Estimates of evolutionary divergence among plant 4CLs.

| | | | | | | |
|---|---|---|---|---|---|---|
| Lp4CL2 | 0.18 | 0.45 | 0.17 | 0.44 | 0.13 | 0.18 |
| Lp4CL3 | 0.16 | 0.49 | 0.15 | 0.47 | 0.19 | 0.18 |
| Os4CL1 | 0.38 | 0.50 | 0.38 | 0.49 | 0.35 | 0.38 |
| Os4CL2 | 0.46 | 0.14 | 0.47 | 0.13 | 0.44 | 0.46 |
| Os4CL3 | 0.10 | 0.46 | 0.09 | 0.44 | 0.14 | 0.10 |
| Os4CL4 | 0.15 | 0.44 | 0.14 | 0.43 | 0.13 | 0.14 |
| Po4CL1 | 0.40 | 0.41 | 0.39 | 0.41 | 0.37 | 0.39 |
| Po4CL2 | 0.41 | 0.44 | 0.40 | 0.43 | 0.39 | 0.41 |
| Po4CL3 | 0.46 | 0.49 | 0.46 | 0.48 | 0.45 | 0.46 |
| Po4CL4 | 0.44 | 0.32 | 0.44 | 0.31 | 0.44 | 0.46 |

| | At4CL1 | At4CL2 | At4CL3 | At4CL4 | Lp4CL1 | Lp4CL2 | Lp4CL3 |
|---|---|---|---|---|---|---|---|
| Sc4CL1 | | | | | | | |
| Sc4CLM | | | | | | | |
| Sb_04g005210 | | | | | | | |
| Sb_04g031010 | | | | | | | |
| Sb_10g026130 | | | | | | | |
| Zm_LOC542166 | | | | | | | |
| At4CL1 | | | | | | | |
| At4CL2 | 0.16 | | | | | | |
| At4CL3 | 0.44 | 0.42 | | | | | |
| At4CL4 | 0.37 | 0.39 | 0.51 | | | | |
| Lp4CL1 | 0.44 | 0.43 | 0.34 | 0.51 | | | |
| Lp4CL2 | 0.39 | 0.41 | 0.45 | 0.51 | 0.44 | | |
| Lp4CL3 | 0.44 | 0.45 | 0.50 | 0.54 | 0.50 | 0.20 | |
| Os4CL1 | 0.42 | 0.45 | 0.49 | 0.53 | 0.48 | 0.34 | 0.38 |
| Os4CL2 | 0.44 | 0.44 | 0.34 | 0.51 | 0.13 | 0.43 | 0.49 |
| Os4CL3 | 0.42 | 0.41 | 0.46 | 0.52 | 0.47 | 0.16 | 0.15 |
| Os4CL4 | 0.41 | 0.41 | 0.45 | 0.53 | 0.46 | 0.13 | 0.19 |
| Po4CL1 | 0.30 | 0.29 | 0.38 | 0.45 | 0.42 | 0.40 | 0.44 |
| Po4CL2 | 0.31 | 0.31 | 0.39 | 0.44 | 0.45 | 0.41 | 0.46 |
| Po4CL3 | 0.31 | 0.33 | 0.44 | 0.45 | 0.48 | 0.47 | 0.49 |
| Po4CL4 | 0.43 | 0.42 | 0.26 | 0.53 | 0.31 | 0.45 | 0.51 |

| | Os4CL1 | Os4CL2 | Os4CL3 | Os4CL4 | Po4CL1 | Po4CL2 | Po4CL3 | Po4CL4 |
|---|---|---|---|---|---|---|---|---|
| Sc4CL1 | | | | | | | | |
| Sc4CLM | | | | | | | | |
| Sb_04g005210 | | | | | | | | |
| Sb_04g031010 | | | | | | | | |
| Sb_10g026130 | | | | | | | | |
| Zm_LOC542166 | | | | | | | | |
| At4CL1 | | | | | | | | |
| At4CL2 | | | | | | | | |
| At4CL3 | | | | | | | | |
| At4CL4 | | | | | | | | |
| Lp4CL1 | | | | | | | | |
| Lp4CL2 | | | | | | | | |
| Lp4CL3 | | | | | | | | |
| Os4CL1 | | | | | | | | |
| Os4CL2 | 0.49 | | | | | | | |
| Os4CL3 | 0.36 | 0.45 | | | | | | |
| Os4CL4 | 0.36 | 0.44 | 0.14 | | | | | |
| Po4CL1 | 0.47 | 0.44 | 0.38 | 0.39 | | | | |
| Po4CL2 | 0.47 | 0.47 | 0.41 | 0.41 | 0.12 | | | |
| Po4CL3 | 0.47 | 0.49 | 0.46 | 0.47 | 0.27 | 0.27 | | |
| Po4CL4 | 0.50 | 0.31 | 0.45 | 0.43 | 0.37 | 0.40 | 0.46 | |

Sc: Sugarcane,
Sb: *Sorghum bicolor*,
Zm: *Zea Mays*,
At: *Arabidopsis Thaliana*,
Lp: *Lolium perenne*,
Os: *Oryza Sativa*,
Po: Poplar Hybrid (*Populus trichocarpa* × *Populus deltoids*)

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

U.S. Pat. No. 4,761,373
U.S. Pat. No. 4,769,061
U.S. Pat. No. 4,810,648

U.S. Pat. No. 4,940,835
U.S. Pat. No. 4,945,050
U.S. Pat. No. 4,975,374
U.S. Pat. No. 4,987,071
U.S. Pat. No. 5,013,659
U.S. Pat. No. 5,023,179
U.S. Pat. No. 5,034,322
U.S. Pat. No. 5,036,006
U.S. Pat. No. 5,093,246
U.S. Pat. No. 5,100,792
U.S. Pat. No. 5,106,739
U.S. Pat. No. 5,116,742
U.S. Pat. No. 5,162,602
U.S. Pat. No. 5,256,558
U.S. Pat. No. 5,270,163
U.S. Pat. No. 5,276,268
U.S. Pat. No. 5,304,730
U.S. Pat. No. 5,495,071
U.S. Pat. No. 5,554,798
U.S. Pat. No. 5,561,236
U.S. Pat. No. 5,569,823
U.S. Pat. No. 5,582,981
U.S. Pat. No. 5,589,610
U.S. Pat. No. 5,591,616
U.S. Pat. No. 5,595,877
U.S. Pat. No. 5,599,672
U.S. Pat. No. 5,625,136
U.S. Pat. No. 5,639,948
U.S. Pat. No. 5,661,017
U.S. Pat. No. 5,723,763
U.S. Pat. No. 5,767,366
U.S. Pat. No. 5,817,785
U.S. Pat. No. 5,879,903
U.S. Pat. No. 5,928,937
U.S. Pat. No. 6,084,155
U.S. Pat. No. 6,329,504
U.S. Pat. No. 6,337,431
U.S. Pat. No. 6,344,318
U.S. Pat. No. 6,455,760
U.S. Pat. No. 6,462,185
U.S. Pat. No. 6,506,559
U.S. Pat. No. 6,696,623
U.S. Pat. No. 6,933,116
U.S. Pat. No. 7,056,704
U.S. Pat. No. 7,078,196
U.S. Pat. No. 7,232,086
U.S. Pat. No. 7,282,564
U.S. Pat. No. 7,365,058
U.S. Pat. No. 7,368,236
U.S. Pat. No. 7,538,095
U.S. Pat. No. 7,700,759
U.S. Pat. No. 7,723,575
U.S. Published Application No. 20010016956
U.S. Published Application No. 20030084486
U.S. Published Application No. 20030177536
U.S. Published Application No. 20040019934
U.S. Published Application No. 20040067506
U.S. Published Application No. 20040078841
U.S. Published Application No. 20040123349
U.S. Published Application No. 20060260011
U.S. Published Application No. 2007006346
U.S. Published Application No. 20090031441
U.S. Published Application No. 20090199307
PCT Published Application No. WO 93/07278
PCT Published Application No. WO 93/21335
EP 0242246
EP 0292435
EP 0392225
EP 138341
EP 295959
Agrawal et al. (2003) *Microbiology and Molecular Biology Reviews*, 67(4):657-685.
Altschul, S. F. et al. (1990) "Basic Local Alignment Search Tool" *J. Mol. Biol.* 215:403-410.
Altschul, S. F. et al. (1997) "Gapped BLAST and PSI-BLAST: A New Generation of Protein Database Search Programs" *Nucl. Acids Res.* 25:3389-3402.
Bartel, D. and Szostak, J. W. *Science* 261:1411-1418 (1993).
Bassett, C. L., Callahan, A., Artlip, T., Scorza, R. Srinivasan, C. (2007) "A minimal peach type II chlorophyll a/b-binding protein promoter retains tissue-specificity and light regulation in tomato" *BMC Biotechnol.*, 7:47.
Beltz, G. A., Jacobs, K. A., Eickbush, T. H., Cherbas, P. T., Kafatos, F. C. (1983) "Isolation of multigene families and determination of homologies by filter hybridization methods" *Methods of Enzymology*, R. Wu, L. Grossman and K. Moldave [eds.] Academic Press, New York 100:266-285.
Bevan, M. (1984) "Binary *Agrobacterium* vectors for plant transformation" *Nucl. Acids Res.*, 12(22):8711-21.
Browning, B. L. 1967. Methods of wood chemistry. Wiley-Interscience, New York.
Brusslan, J. A. and Tobin, E. M. (1992) "Light-independent developmental regulation of cab gene expression in *Arabidopsis thaliana* seedlings" *Proc Natl Acad Sci USA*, 89(16):7791-5.
Bustos et al. (1989) *Plant Cell*, 1:839-854.
Chandler et al. (1989) "Two Regulatory Genes of the Maize Anthocyanin Pathway Are Homologous: Isolation of B Utilizing R Genomic Sequences" *The Plant Cell*, 1:1175-1183.
Chengalrayan, K. and Gallo-Meagher, M. (2001) "Effect of various growth regulators on shoot regeneration of sugarcane" *In Vitro Cell. Dev. Biol. Plant*, 37:434-439.
Clancy, M. and Hannah, L. C. (2002) "Splicing of the maize Sh1 first intron is essential for enhancement of gene expression, and a T-rich motif increases expression without affecting splicing" *Plant Physiol.* 130(2):918-29.
Deblaere, R., Reynaerts, A., Hofte, H., Hernalsteens, J.-P., Leemans, J., and Van Montagu, M. (1987) "Vectors for cloning in plant cells" *Methods Enzymol.*, 153:77-292.
Doran, T. and Helliwell, C. (2009) RNA interference: Methods for plants and animals; Publisher: CABI, Wallingford, UK.
Ebert et al. (1987) *Proc. Nat'l Acad. Sci.* USA. 84:5745-5749.
Ehlting, J., Buttner, D., Wang, Q., Douglas, C. J., Somssich, I., and Kombrink, E. (1999). Three 4-coumarate:coenzyme A ligases in *Arabidopsis thaliana* represent two evolutionarily divergent classes in angiosperms. Plant J. 19, 9-20.
Ellington, A. D. and Szostak, J. W. (1990) "In vitro selection of RNA molecules that bind specific ligands" *Nature*, 346 (6287):818-822.
Fromm et al. *Biotechnology* 8:833-839 (1990).
Good, X. et al. (1994) "Reduced ethylene synthesis by transgenic tomatoes expressing S-adenosylmethionine hydrolase" *Plant Molec. Biol.* 26:781-790.
Gordon-Kamm et al. *Plant Cell* 2:603-618 (1990).
Green et al., *EMBO J.*, 7:4035-4044 (1988).
Haseloff and Gerlach *Nature* 334:585-591 (1988).
Hofgen & Willmitzer, *Nucl. Acids Res.* 16:9877 (1988).
Hoppe-Seyler, F. and Butz, K. (2000) "Peptide aptamers: powerful new tools for molecular medicine" *J. Mol. Med.*, 78(8):426-430.
Hudspeth et al. (1989) *Plant Mol. Biol.*, 12:579-589.

James V A, Neibaur I, Altpeter F: Stress inducible expression of the DREB1A transcription factor from xeric, *Hordeum spontaneum* L. in turf and forage grass (*Paspalum notatum* Flugge) enhances abiotic stress tolerance. Transgenic Res 2008, 17:93-104.
Jordano et al., *Plant Cell,* 1:855-866 (1989).
Karlin S., Altschul, S. F. (1990) "Methods for Assessing the Statistical Significance of Molecular Sequence Features by Using General Scoring Schemes" *Proc. Natl. Acad. Sci. USA* 87:2264-2268.
Karlin S., Altschul, S. F. (1993) "Applications and Statistics for Multiple High-Scoring Segments in Molecular Sequences" *Proc. Natl. Acad. Sci.* USA 90:5873-5877.
Klein et al. (1987) *Nature* 327:70-73.
Koziel et al. (1993) *Biotechnology* 11:194-200.
Kusaba (2004) *Current Opinion in Biotechnology,* 15:139-143.
Kwon et al. (1994) *Plant Physiol.* 105:357-67.
Lawton et al. (1987) *Plant Mol. Biol.* 9:315-324.
Maniatis, T., Fritsch, E. F., Sambrook, J. (1982) *Molecular Cloning: A Laboratory Manual,* Cold Spring Harbor Laboratory, Cold Spring Harbor, N.Y.
Matsuoka et al. (1993) "Tissue-specific light-regulated expression directed by the promoter of a C4 gene, maize pyruvate, orthophosphate dikinase, in a C3 plant, rice" *PNAS* USA, 90(20):9586-90.
Matsuoka et al. (1994) *Plant J.* 6:311-319.
Mayo, O. (1987) The Theory of Plant Breeding, Second Edition, Clarendon Press, Oxford.
Meier et al. (1991) *Plant Cell,* 3:309-316.
Milhavet et al. (2003) *Pharmacological Reviews,* 55(4):629-648.
Odell et al. (1985) *Nature* 313:810-812.
Paszkowski et al. (1984) *EMBO J.* 3:2717-2722.
Potrykus et al. (1985) *Mol. Gen. Genet.* 199:169-177.
Reich et al. (1986) *Biotechnology* 4:1001-1004.
Richins et al. (1987) *Nucleic Acids Res.* 20:8451.
Sambrook, J., Fritsch, E. F., and Maniatis, T. (1989) *Molecular Cloning: A Laboratory Manual.* Vols. 1 and 3. Cold Spring Harbor Laboratory Press, Cold Spring Harbor, N.Y.
Singh, D. P. (1986) Breeding for Resistance to Diseases and Insect Pests, Springer-Verlag, NY.
Sullivan et al. (1989) "Isolation and characterization of a maize chlorophyll a/b binding protein gene that produces high levels of mRNA in the dark" *Mol. Gen. Genet.,* 215 (3):431-440.
Tamura K., Dudley J., Nei M., and Kumar S (2007) MEGA4: Molecular Evolutionary Genetics Analysis (MEGA) software version 4.0. Molecular Biology and Evolution 24:1596-1599.
Theander, O., and E. A. Westerlund (1986). Studies on dietary fiber. 3. Improved procedures for analysis of dietary fiber. J. Agric. Food Chem. 34:330-336
Uknes et al. (1993) *Plant Cell* 5: 159-169.
Walker et al. (1987) *Proc. Nat'l Acad. Sci.* USA, 84:6624-6628.
Wang et al. (1992) "Characterization of cis-Acting Elements Regulating Transcription from the Promoter of a Constitutively Active Rice Actin Gene" *Molecular and Cellular Biology,* 12(8):3399-3406.
Welsh J. R. (1981) Fundamentals of Plant Genetics and Breeding, John Wiley & Sons, NY.
Wood D. R. (1983) (Ed.) Crop Breeding, American Society of Agronomy Madison, Wis.
Wricke and Weber (1986) Quantitative Genetics and Selection Plant Breeding, Walter de Gruyter and Co., Berlin.
www.lifesci.sussex.ac.uk/home/Neil_Crickmore/Bt/
Xu, D., McElroy, D., Thornburg, R. W., Wu, R. et al. (1993) "Systemic induction of a potato pin2 promoter by wounding, methyl jasmonate, and abscisic acid in transgenic rice plants" *Plant Molecular Biology* 22:573-588.
Yamamoto et al. (1994) *Plant Cell Physiol.* 35:773-778.
Yamamoto et al. (1997) *Plant J.* 12(2):255-265.
Yang et al. (1990) *Proc. Nat'l Acad. Sci.* USA, 87:4144-4148.
Yang, T. T. et al. (1996) "Optimized Codon Usage and Chromophore Mutations Provide Enhanced Sensitivity with the Green Fluorescent Protein" *Nucleic Acid Research* 24(22): 4592-4593.
Yoshihara, K., T. Kobayashi, T. Fujii, and I. Akamatsu (1984). A novel modification of Klason lignin quantitative method. J. Japan Tappi 38:86-95.
Zhang et al. (1996) *Plant Physiology,* 110:1069-1079.
Zubieta, C, Kota, P, Ferrer, J. L., Dixon, R. A., Noel, J. P. (2002) "Structural basis for the modulation of lignin monomer methylation by caffeic acid/5-hydroxyferulic acid 3/5-O-methyltransferase" *Plant Cell.,* 14(6):1265-77.
Zuckerkandl E & Pauling L (1965) Evolutionary divergence and convergence in proteins, pp. 97-166 in *Evolving Genes and Proteins*, edited by V. Bryson and H. J. Vogel. Academic Press, New York.

We claim:

1. A method for reducing lignin biosynthesis in a plant, comprising suppressing or downregulating the expression of one or more 4-coumarate-CoA ligase (4CL) genes and/or function of one or more 4CL enzymes involved in the lignin biosynthesis pathway in the plant, wherein said 4CL gene or said 4CL enzyme is 4CL-M, 4CL-N, or 4CL-L, and wherein lignin biosynthesis is reduced in the plant.

2. The method according to claim 1, wherein lignin biosynthesis is selectively downregulated in leaf tissue or a leaf cell.

3. The method according to claim 1, wherein suppression or downregulation is achieved by introducing in a cell of said plant a polynucleotide sequence that provides for an antisense, cosuppression, RNA interference (RNAi), short interfering RNA (siRNA), or ribozyme sequence that when expressed in a cell of said plant suppresses or downregulates expression of said one or more 4CL genes and/or one or more 4CL enzymes; or wherein suppression or downregulation is achieved by introducing in a cell of said plant a knockout mutation in one or more genes encoding said one or more 4CL enzymes.

4. The method according to claim 1, wherein suppression or downregulation is achieved by contacting said one or more 4CL enzymes with an antibody, or an antigen binding fragment thereof, or an aptamer that can bind to and block or inhibit function of said enzyme.

5. The method according to claim 3, wherein suppression or downregulation is achieved using said RNAi sequence to downregulate expression of one or more 4CL genes.

6. A transformed or transgenic plant, plant tissue, or plant cell having suppressed or downregulated lignin biosynthesis, wherein expression of one or more 4-coumarate-CoA ligase (4CL) genes and/or function of one or more 4-coumarate-CoA ligase (4CL) enzymes involved in a lignin biosynthesis pathway is suppressed or downregulated, wherein said 4CL gene or said 4CL enzyme is 4CL-M, 4CL-N, or 4CL-L, and wherein lignin biosynthesis is reduced in the plant, plant tissue, or plant cell.

7. The plant, plant tissue, or plant cell according to claim 6, wherein lignin biosynthesis is selectively downregulated in leaf tissue.

8. The plant, plant tissue, or plant cell according to claim 6, wherein suppression or downregulation is achieved by introducing in a cell of said plant a polynucleotide sequence that provides for an anti sense, cosuppression, RNA interference (RNAi), short interfering RNA (siRNA), or ribozyme sequence that when expressed in a cell of said plant suppresses or downregulates expression of said one or more 4CL genes and/or one or more 4CL enzymes; or wherein suppression or downregulation is achieved by introducing in a cell of said plant a knockout mutation in one or more genes encoding said one or more 4CL enzymes.

9. The plant, plant tissue, or plant cell according to claim 6, wherein suppression or downregulation is achieved by contacting said one or more 4CL enzymes with an antibody, or an antigen binding fragment thereof, or an aptamer that can bind to and block or inhibit function of said enzyme.

10. The plant, plant tissue, or plant cell according to claim 6, wherein said plant tissue is from branches, kernels, ears, cobs, husks, root tips, anthers, seeds, roots, embryos, hypocotyls, cotyledons, pollen, ovules, shoots, stalks, stems, leaves, fruits, or flowers.

11. The plant, plant tissue, or plant cell according to claim 6, wherein said plant, plant tissue, or plant cell is from sugarcane.

12. The sugarcane plant, plant tissue, or plant cell according to claim 11, wherein said sugarcane plant is *Saccharum arundinaceum, Saccharum bengalense, Saccharum edule, Saccharum officinarum, Saccharum procerum, Saccharum ravennae, Saccharum robustum, Saccharum sinense*, or *Saccharum spontaneum*.

13. The plant, plant tissue, or plant cell according to claim 6, wherein said plant is a hybrid or inbred line.

14. The plant, plant tissue, or plant cell according to claim 6, wherein said plant comprises one or more agronomic traits of interest.

15. The plant, plant tissue, or plant cell according to claim 14, wherein said agronomic trait is herbicide resistance, virus resistance, bacterial pathogen resistance, insect resistance, nematode resistance, fungal resistance, plant vigor, or plant yield.

16. An RNAi construct comprising a polynucleotide sequence that downregulates or suppresses expression of a 4CL gene of a plant wherein said 4CL ene is 4CL-M, 4CL-N, or 4CL-L.

17. A method for preparing a transformed or transgenic plant, plant tissue, or plant cell having suppressed or downregulated lignin biosynthesis, wherein expression of one or more 4-coumarate-CoA ligase (4CL) genes and/or function of one or more 4-coumarate-CoA ligase (4CL) enzymes involved in a lignin biosynthesis pathway is suppressed or downregulated, the method comprising: incorporating a polynucleotide in a cell of said plant, wherein expression of said polynucleotide suppresses or downregulates the expression of one or more 4CL genes and/or the function of one or more 4CL enzymes involved in lignin biosynthesis in said plant, wherein said 4CL gene or said 4CL enzyme is 4CL-M, 4CL-N, or 4CL-L, and wherein lignin biosynthesis is reduced in the plant, plant tissue, or plant cell.

18. The method according to claim 17, wherein lignin biosynthesis is selectively downregulated in leaf tissue or a leaf cell.

19. The method according to claim 17, wherein suppression or downregulation is achieved by introducing in a cell of said plant a polynucleotide sequence that provides for an antisense, cosuppression, RNA interference (RNAi), short interfering RNA (siRNA), or ribozyme sequence that when expressed in a cell of said plant suppresses or downregulates expression of said one or more 4CL genes and/or one or more 4CL enzymes; or wherein suppression or downregulation is achieved by introducing in a cell of said plant a knockout mutation in one or more genes encoding said one or more 4CL enzymes.

20. The method according to claim 17, wherein suppression or downregulation is achieved by contacting said one or more 4CL enzymes with an antibody, or an antigen binding fragment thereof, or an aptamer that can bind to and block or inhibit function of said enzyme.

21. The method according to claim 1, wherein said plant is sugarcane.

22. The method according to claim 21, wherein said sugarcane plant is *Saccharum arundinaceum, Saccharum bengalense, Saccharum edule, Saccharum officinarum, Saccharum procerum, Saccharum ravennae, Saccharum robustum, Saccharum sinense*, or *Saccharum spontaneum*.

23. The method according to claim 1, wherein said plant is a hybrid or inbred line.

24. The method according to claim 17, wherein said plant, plant tissue, or plant cell is sugarcane.

25. The method according to claim 24, wherein said sugarcane plant is *Saccharum arundinaceum, Saccharum bengalense, Saccharum edule, Saccharum officinarum, Saccha-

*rum procerum, Saccharum ravennae, Saccharum robustum, Saccharum sinense*, or *Saccharum spontaneum*.

26. The method according to claim 17, wherein said plant is a hybrid or inbred line.

27. The sugarcane plant, plant tissue, or plant cell according to claim 11, wherein said sugarcane plant is a hybrid of *Saccharum* and *Miscanthus* or *Erianthus*, or *Sorghum*.

28. The method according to claim 21, wherein said sugarcane plant is a hybrid of *Saccharum* and *Miscanthus* or *Erianthus*, or *Sorghum*.

29. The method according to claim 24, wherein said sugarcane plant is a hybrid of *Saccharum* and *Miscanthus* or *Erianthus*, or *Sorghum*.

30. The method according to claim 1, wherein said plant is transformed with a polynucleotide that is stably incorporated into the genome of said plant, wherein expression of said polynucleotide inhibits or downregulates lignin biosynthesis in said plant.

31. The transformed or transgenic plant, plant tissue, or plant cell according to claim 6, wherein said plant is transformed with a polynucleotide that is stably incorporated into the genome of said plant, wherein expression of said polynucleotide inhibits or downregulates lignin biosynthesis in said plant.

32. The method according to claim 17, wherein said plant cell is transformed with a polynucleotide that is stably incorporated into the genome of said plant, wherein expression of said polynucleotide inhibits or downregulates lignin biosynthesis in said plant.

33. The method according to claim 5, wherein said RNAi sequence comprises the nucleotide sequence of SEQ ID NO:4.

34. The method according to claim 5, wherein said RNAi sequence comprises the nucleotide sequence of SEQ ID NO:5.

35. The method according to claim 1, wherein said 4CL gene is 4CL-L.

36. The plant, plant tissue, or plant cell according to claim 8, wherein suppression or downregulation is achieved using said RNAi sequence to suppress or downregulate expression of one or more 4CL genes.

37. The plant, plant tissue, or plant cell according to claim 36, wherein said RNAi sequence comprises the nucleotide sequence of SEQ ID NO:4 or SEQ ID NO:5.

38. The RNAi construct according to claim 16, wherein said RNAi construct comprises the nucleotide sequence of SEQ ID NO:4 or SEQ ID NO:5.

39. The method according to claim 19, wherein suppression or downregulation is achieved using said RNAi sequence to suppress or downregulate expression of one or more 4CL genes.

40. The method according to claim 39, wherein said RNAi sequence comprises the nucleotide sequence of SEQ ID NO:4 or SEQ ID NO:5.

41. The method according to claim 1, wherein said method further comprises assaying for lignin content in said plant.

42. The method according to claim 17, wherein said method further comprises assaying for lignin content in said plant.

43. The method according to claim 1, wherein said 4CL gene is 4CL-M.

44. The method according to claim 1, wherein said 4CL gene is 4CL-N.

45. The plant, plant tissue, or plant cell according to claim 6, wherein said 4CL gene is 4CL-L.

46. The plant, plant tissue, or plant cell according to claim 6, wherein said 4CL gene is 4CL-M.

47. The plant, plant tissue, or plant cell according to claim 6, wherein said 4CL gene is 4CL-N.

48. The method according to claim 17, wherein said 4CL gene is 4CL-L.

49. The method according to claim 17, wherein said 4CL gene is 4CL-M.

50. The method according to claim 17, wherein said 4CL gene is 4CL-N.

51. The method according to claim 17, further comprising growing a plant from said cell.

52. The method according to claim 23, wherein said plant is a hybrid of *Saccharum spontaneum* and *Saccharum officianarum*.

53. The method according to claim 26, wherein said plant is a hybrid of *Saccharum spontaneum* and *Saccharum officianarum*.

54. The plant, plant tissue, or plant cell according to claim 13, wherein said plant is a hybrid of *Saccharum spontaneum* and *Saccharum officianarum*.

\* \* \* \* \*

UNITED STATES PATENT AND TRADEMARK OFFICE
CERTIFICATE OF CORRECTION

Page 1 of 1

PATENT NO. : 9,187,757 B2
APPLICATION NO. : 13/376286
DATED : November 17, 2015
INVENTOR(S) : Fredy Altpeter et al.

It is certified that error appears in the above-identified patent and that said Letters Patent is hereby corrected as shown below:

IN THE SPECIFICATION

Column 2,
Line 67, "*Oryza saliva*" should read --*Oryza sativa*--

IN THE CLAIMS

Column 109,
Line 47, "anti sense" should read --antisense--

Column 110,
Line 19, "4CL ene is" should read --4CL gene is--

Signed and Sealed this
Fifth Day of April, 2016

Michelle K. Lee
*Director of the United States Patent and Trademark Office*

SEQUENCE LISTING

```
<160> NUMBER OF SEQ ID NOS: 54

<210> SEQ ID NO 1
<211> LENGTH: 617
<212> TYPE: DNA
<213> ORGANISM: Saccharum

<400> SEQUENCE: 1
ccacggcgaa gaccatcgac tcggagggct ggctgcacac cggagacatc gggtacgtcg      60
acgacgacga cgaaatcttc atcgtcgacc ggctcaagga gctcatcaag tacaaggggt     120
tccaagtcgc tccggcggag ctcgaggcca tgctcatcgc ccaccccagc atcgccgacg     180
ccgccgtcgt cccactgaag gatgactcct gcggcgagat cccggtggcg ttcgtcgtga     240
cgtccggcgg ctcggagatc accgaggacg aaatcaaaca gtacgtggcg aaacaggtgg     300
tgttctataa gaggctgcac aagatcttct tcgtggagga tatcccgaag gcgccatctg     360
```

```
gcaagatttt gaggaaggat ctgagagcaa agctggcgtc tggattttcc aacggatcat    420
cttgttgatg accctgaggg cctgagttct ttctatacga aaacgacccc ggttttagtt    480
gttttttatg ctgaacaagc taaaaaaga tatacagaaa acggtgtaaa cgagaagcag     540
tcaaccatgt acaagacatg ttatctagat aaatgaaagc ttttttgaaa aaaaaaaaa     600 aaaaaaaaaa aaaaaa                                                    617
```

```
<210> SEQ ID NO 2
<211> LENGTH: 1728
<212> TYPE: DNA
<213> ORGANISM: Saccharum

<400> SEQUENCE: 2
```

```
atgatcacgg tggctgcacc ggaggcgcag tcacaggtgg cggcggcggc cgtggcgccc     60
gcggcgccgg aggagaccgt gttccggtcg aagctgccgg acatcgacat ccccagccac    120
ctgcccctgc acgagtactg cttcgcgagg cggcggagg tcgcggacgc gccgtgcctc     180
atcgcggcgg ccacggggag gacctacacg tacgccgaga cgcgcctcct gtgccgcaag    240
gccgcggcgt cgctgcacgg gctcggcgtc ggccagggcg actgcgtcat gatcctgctc    300
cagaactccg tcgagttcgt gctcaccttc ttcggcgcgt cgttcctcgg cgccgtcacc    360
acggccgcca acccgttctg cacgccgctg gagatccaca agcagttcag ggcctccggc    420
tcgaagctca tcgtcaccca gtccgcctac gtcgacaagc tccggcacga ggccttcccg    480
aggatcgggg cggcgagcga cggcggcgag gacgaggaca tgccctcac cgtcctcacc     540 atcgacgacg cggccagcac cccggaaggc tgcctggcgt tctgggagct ggtcacgccc    600
gccgacgacg ccgcgctccc ggaggtgtcc atctcccccg acgacccgt ggcgctgccg     660 ttctcgtcgg gcaccacggg gctgcccaag ggcgtggtgc tcacccacgg cgggcaggtg    720
tccaacgtgg cgcagcaggt ggacggcgcg aacccgaacc tgtacatgcg agagggcgac    780
gtcgcgctct gcgtgctgcc gctgttccac atcttctcgc tcaactcggt gctgctgtgc    840
gcgctgcgcg ccggcgcggc ggtgatgctg atgcccaagt cgagatgggg cgcgatgctg    900
gagggcatcc agcggtggcg cgtcacggtg ccgccgtcg tgccaccgct ggtgctcgcg     960
ctggccaagg accccgcgct ggagaagtac gacctcagct ccatccggat cgtgctctcc   1020
ggcgccgcgc gcttggcaa ggagctcgtc gacgcgctcc gcgcccgcgt gccacaggcc    1080
gtcttcggac aggggtacgg gatgacggag gccgggcccg tgctgtccat gtgcccagcg   1140
ttcgccaagg agccgacgcc cgccaagccg gagtcgtgcg gcacggtggt gcgcaacgca    1200
gagctcaagg tggtggaccc cgacacgggc ctctcgctca gccgcaacct ccccggcgag    1260
atctgcatcc ggggccccgca gatcatgaaa gggtacctga cgacccgga ggccaccgcg    1320 aggacgatcg acgtcgacgg ctggctccac accggcgaca tcggctacgt cgacgacgac   1380
gaggaggtct tcatcgtcga ccgcgtcaag gagctcatca agttcagggg cttccaggtg    1440 ccgccggcc agctcgaggc tctgctaatc gcccacccat ccatcgccga cgcagccgtc    1500
gtcccgcaaa aggatgacgc cgccggcgag gtccctgtcg ccttcgtggt tcgcgccacc    1560
gattctgaca tcgcggagga tgccatcaag gacttcatct ccaagcaggt ggtgttctac    1620
aagaggctat acaaggtgta cttcacccc tccatcccca gtcagcgtc cgggaagatc      1680 ctgaggagag agctgcgcgc caagctcgcg gcagccgcaa ccacttga                 1728
```

```
<210> SEQ ID NO 3
<211> LENGTH: 1665
```

```
<212> TYPE: DNA
<213> ORGANISM: Saccharum

<400> SEQUENCE: 3
atgggttccg tggacacggc ggtcgcggtg ccggtgccgg tggcggagcc ggcggcggag      60
gagaaggcgg tggtgttccg gtccaagctt cccgatatcg agatcaacaa cagccagtcg     120
ctgcacgcct actgcttcgg gaagatgagc gaggtggcgg accgcgcctg cctcgtcgac     180
gggcagaccg cgcgtcgta cacgtacgcg gaggtggagt ccctgtcccg ccgcgccgcg      240
tcgggcctgc gcgccatggg cgtgggcaag ggcgacgtgg tgatgaacct gctccgcaac     300 tgcccccgagt tcgccttcac cttcttcggc gccgcgcggc tgggcgccgc caccaccacg    360
gccaacccgt tctacacccc gcacgagatc accgccagg cggaggcggc cggcgccaag      420
ctcatcgtca ccgaggcctg cgccgtggag aaggtgcgcg agttcgcggc ggggcggggc     480
gtccccgtcg tcaccgtcga cggccgcttc gacggctgcg tcgagttcgc cgaggtgatc     540
gcggccgagg agctcgaggc cgacgtcgac gtccaccccg acgacgtcgt cgcgctgcct     600
tactcctccg gcaccaccgg actccccaag ggcgtcatgc tcacccaccg cagcctcatc     660
accagcgtcg cgcagcaggt tgacggcgag aacccgaacc tgtacttcag caaggacgac     720
gtgctgctgt gcctgctgcc gctgttccac atctactcgc tcaactcggt gctgctggcg     780
gggctgcgcg cgggctccac catcgtgatc atgcgcaagt cgacctgggg cgcgctggtg     840
gacctggtgc gcaagcacgc catcaccatc gcgcccttcg tgccgcccat cgtggtggag     900
atcgccaaga gccccgcgt gaccgccgcc gacctgcct ccatccgcat ggtcatgtcc       960
ggcgccgcgc ccatgggcaa ggagctccag gacgccttca tgaccaagat ccccaacgcc    1020
gtcctcgggc aggggtacgg gatgacggag gcggggcccg tgctggcgat gtgcctggcg    1080
ttcgccaagg agccgttcca ggtcaagtcc gggtcgtgcg gcaccgtggt gcgcaacgcg    1140
gagctgaaga tcgtcgaccc cgacaccggc gccgccctcg gccggaacca gcccggcgag    1200
atctgcatcc gcggggagca gatcatgaaa ggttacctga cgaccccga gtcgacaaag     1260 aacaccatcg acaagggcgg ctggctgcac accggcgaca tcggctacgt cgacgacgac    1320
gacgagatct tcatcgtcga caggctcaag gagatcatca agtacaaggg gttccaggtg    1380
cccccggcgg agatcgaggc gctcctcatc acgcacccgg agatcaagga cgccgccgtc    1440
gtgtcaatga aggatgatct tgctggtgaa atccctgtcg ccttcatcgt gcggaccgaa    1500
ggctctgaag tcaccgagga tgtgatcaag caatttgtcg ccaaggaggt ggttttctac    1560
aagaaggtac acaaggtttt cttcaccgaa tccatcccca gaacccgtc cggcaagatc      1620 ctaaggaagg acttgagagc caggctcgcc gccgctgttc actga                    1665

<210> SEQ ID NO 4
<211> LENGTH: 2739
<212> TYPE: DNA
<213> ORGANISM: Artificial Sequence
<220> FEATURE:
<223> OTHER INFORMATION: ScL4CL-Li RNAi construct

<400> SEQUENCE: 4
aattcggtac cgtatgcgga tgaattaaga gccccgaata cgaaaatacc cttattttcg     60
cgtgtgggtg ttttaagtga tccgtttgga aaaattgatt ttttgcatac gggtctttaa    120
ggagccgtat gggaaaacgg aggtcgagtt ttgcatacgt ggacacttat ggtccgtctg    180
taatttattg gatgctcgtt cagaaaaatt atttttagt aatgttagtt gctgagcaaa      240
```

-continued

```
tgacaattgt caccgctcca cctaactcaa aaagacacag ggagcttttg attgaaatgg      300
tccaaaccga agagctgaac atctggttgg taaatgtctc ctctcagttc aacgaatatc      360
gggcagataa cagattctcg catatataat tgtctcgtaa taaactgtgc aatgtcaacc      420
tcattttagt agcacatttg ttttggatag tagcatggcc tagctttgtc catctctttt      480
cttcccttct ccgtgccata ccacacaaca ttttgatttg ggacaaaagg ttggtgaaat      540
ggacatattt tcacatatat atatgctata ttttcttct cagtttaccg aaaagatgta       600
cccttatatc tcgtcatcga ttttgggtca ggccagaaaa ccattggtaa cagaatatat      660
gcatagtttt ctttatcaat aaaattaatg ttttatttaa aaatcgataa aggaactttt      720
tacaaaatta ggctagaaat ggtctgtcta ttatgacaag gtaaacttt gcgacattaa       780
tttggatggc aacttcaaca attcaaattg tcgttgtcca caaatctctt ggttgtagaa      840
gacccacgcg tctgcaacat ttttgcgccg aaaactaat acataaactt gatttgttgg       900
gatacatggt gcagaagata cgatcattaa taattcaaac agtgcatttc atggtccaac      960
tgactgccac gtcattgaac ccgtaatcat tcgctaagcc aaatcaaatt ggcctcaaat     1020
gaatttcag cacgactttt tacgcccaa aaacctagta ctccctccag ttggaaatgt      1080
accctaccaa gaaacttgtg tccgtcacga cgcctgtatc atcaatctag tcctcttttg     1140
taacaaaata attttagaag atttctttta atgccgtaga aattaaatta atcctaatga    1200
aaatcatgta aaactcaccc gttataaaat gtcactaacc cctcacacgg ttggtgtcct    1260
ctttgtagcc gaaatgcctc ctctttggcc actgcatctc cacccatttt tcaaacatct    1320
ccaactaact ttttgttcca tttgcaaaaa tgcaaaatgc gaaatgttaa cttcacacac    1380
acccccctac cactacaaaa ctctcaccaa ccccaatcta gctatcagtt cagaaagcac    1440
cttcccttct ttccctatta gagcaagtct aatagtacag ctcactacta gcttcaattt    1500
atctataacc aatctaatag tcaattcata caatagttgc ttattatact attaatatat    1560
ggtctcacct gtcatacaca cagtgtgtct tatagtccgt gctgcagctg gctacatatc    1620
tgtagcctgc tagtcttctc tctcattgtt tatctcatta aaatatgttt atagctggct    1680
aatagcttgc taatagcatg ctattgtacc tgctcttacc accttctttc ccttttggca    1740
aatggcaatg agtgcaaaaa tgcttggaaa ataaccccc ccccccccac ccccacctga     1800
ttatttccag tagggccaaa atccgggccc acgtccgcaa cccatgtggg ccccacatcc    1860
cccacaccaa ccctctgcac ccaaaatccc catcccccca ctatatataa tccccgccgt    1920
tggatcatcg ccctcagcag agcagcgcat ctgcatccaa aaccaaaccc aaactcgtct    1980
tctccaccgg agcagagcag cggcgcgcca ctagtgaatt ctagacgggg cgtcggcgat    2040
gctgggtgg gcgatgagca tggcctcgag ctccgccgga gcgacttgga accccttgta    2100
cttgatgagc tccttgagcc ggtcgacgat gaagatttcg tcgtcgtcgt cgacgtaccc    2160
gatgtctccg gtgtgcagcc agccctccga gtcgatggtc ttcgccgtgg catccgggtt    2220
gttgatgggt agtactacct actccaaaac aaagccttga actcttgaaa aaaaagaga    2280
gaaggtgacg cactcgctga cgatcttgga acgtacgcgc agatatcaac aacccggatg    2340
ccacggcgaa gaccatcgac tcggagggct ggctgcacac cggagacatc gggtacgtcg    2400
acgacgacga cgaaatcttc atcgtcgacc ggctcaagga gctcatcaag tacaagggt     2460
tccaagtcgc tccggcggag ctcgaggcca tgctcatcgc ccaccccagc atcgccgacg    2520
ccccgtctag actcgagttt ctccataata atgtgtgagt agttcccaga taagggaatt    2580
agggttccta tagggtttcg ctcatgtgtt gagcatataa gaaacccctta gtatgtattt    2640
```

```
gtatttgtaa aatacttcta tcaataaaat ttctaattcc taaaaccaaa atccagtact    2700
aaaatccaga tccccatta ccctgttatc cctagaatt                            2739

<210> SEQ ID NO 5
<211> LENGTH: 2747
<212> TYPE: DNA
<213> ORGANISM: Artificial Sequence
<220> FEATURE:
<223> OTHER INFORMATION: ScL4CL-Mi RNAi construct

<400> SEQUENCE: 5
aattcggtac cgtatgcgga tgaattaaga gccccgaata cgaaaatacc cttattttcg      60
cgtgtgggtg ttttaagtga tccgtttgga aaaattgatt ttttgcatac gggtctttaa     120
ggagccgtat gggaaaacgg aggtcgagtt ttgcatacgt ggacacttat ggtccgtctg     180
taatttattg gatgctcgtt cagaaaaatt attttttagt aatgttagtt gctgagcaaa     240
tgacaattgt caccgctcca cctaactcaa aagacacag ggagcttttg attgaaatgg      300
tccaaaccga agagctgaac atctggttgg taaatgtctc ctctcagttc aacgaatatc     360
gggcagataa cagattctcg catatataat tgtctcgtaa taaactgtgc aatgtcaacc     420
tcattttagt agcacatttg ttttggatag tagcatggcc tagctttgtc catctctttt     480
cttcccttct ccgtgccata ccacacaaca ttttgatttg ggacaaaagg ttggtgaaat     540
ggacatattt tcacatatat atatgctata tttttcttct cagtttaccg aaaagatgta     600
cccttatatc tcgtcatcga tttttgggtca ggccagaaaa ccattggtaa cagaatatat    660
gcatagtttt ctttatcaat aaaattaatg ttttatttaa aaatcgataa aggaacttt      720 tacaaaatta ggctagaaat ggtctgtcta ttatgacaag gtaaactttt gcgacattaa     780
tttggatggc aacttcaaca attcaaattg tcgttgtcca caaatctctt ggttgtagaa     840
gacccacgcg tctgcaacat ttttgcgccg aaaacttaat acataaactt gatttgttgg     900
gatacatggt gcagaagata cgatcattaa taattcaaac agtgcatttc atggtccaac     960
tgactgccac gtcattgaac ccgtaatcat tcgctaagcc aaatcaaatt ggcctcaaat    1020
gaattttcag cacgactttt tacgccccaa aaacctagta ctccctccag ttggaaatgt    1080
accctaccaa gaaacttgtg tccgtcacga cgcctgtatc atcaatctag tcctcttttg    1140
taacaaaata attttagaag atttctttta atgccgtaga aattaaatta atcctaatga    1200
aaatcatgta aaactcaccc gttataaaat gtcactaacc ccctacacgg ttggtgtcct    1260
ctttgtagcc gaaatgcctc ctctttggcc actgcatctc cacccatttt tcaaacatct    1320
ccaactaact ttttgttcca tttgcaaaaa tgcaaaatgc gaaatgttaa cttcacacac    1380 accccctac cactacaaaa ctctcaccaa ccccaatcta gctatcagtt cagaaagcac    1440
cttcccttct ttccctatta gagcaagtct aatagtacag ctcactacta gcttcaattt    1500
atctataacc aatctaatag tcaattcata caatagttgc ttattatact attaatatat    1560
ggtctcacct gtcatacaca cagtgtgtct tatagtccgt gctgcagctg gctacatatc    1620
tgtagcctgc tagtcttctc tctcattgtt tatctcatta aaatatgttt atagctggct    1680
aatagcttgc taatagcatg ctattgtacc tgctcttacc accttctttc ccttttggca    1740
aatggcaatg agtgcaaaaa tgcttggaaa ataaccccc cccccccac ccccacctga     1800 ttatttccag tagggccaaa atccgggccc acgtccgcaa cccatgtggg ccccacatcc    1860
cccacaccaa ccctctgcac ccaaaatccc catccccca ctatatataa tccccgccgt     1920
```

```
tggatcatcg ccctcagcag agcagcgcat ctgcatccaa aaccaaaccc aaactcgtct    1980
tctccaccgg agcagagcag cggcgcgcca ctagtgaatt cccttttcatg atctgcgggc   2040
cccggatgca gatctcgccg gggaggttgc ggctgagcga gaggcccgtg tcggggtcca   2100
ccaccttgag ctctgcgttg cgcaccaccg tgccgcacga ccccggcttg gcgggcgtcg   2160
gctccttggc gaacgccggg cacatggaca gcacgggccc ggcttccgtc atcccgtacc   2220
cttgatgggt agtactacct actccaaaac aaagccttga actcttgaaa aaaaagaga    2280
gaaggtgacg cactcgctga cgatcttgga acgtacgcgc agatatcaag ggtacgggat   2340
gacggaagcc gggcccgtgc tgtccatgtg cccggcgttc gccaaggagc cgacgcccgc   2400
caagccgggg tcgtgcggca cggtggtgcg caacgcagag ctcaaggtgg tggaccccga   2460
cacgggcctc tcgctcagcc gcaacctccc cggcgagatc tgcatccggg cccgcagat    2520
catgaaaggg aattctagac tcgagtttct ccataataat gtgtgagtag ttcccagata   2580
agggaattag ggttcctata gggtttcgct catgtgttga gcatataaga aacccttagt   2640
atgtatttgt atttgtaaaa tacttctatc aataaaattt ctaattccta aaaccaaaat   2700
ccagtactaa aatccagatc ccccattacc ctgttatccc tagaatt                2747
```

<210> SEQ ID NO 6
<211> LENGTH: 141
<212> TYPE: PRT
<213> ORGANISM: Saccharum

<400> SEQUENCE: 6

Thr Ala Lys Thr Ile Asp Ser Glu Gly Trp Leu His Thr Gly Asp Ile
1               5                   10                  15

Gly Tyr Val Asp Asp Asp Glu Ile Phe Ile Val Asp Arg Leu Lys
            20                  25                  30

Glu Leu Ile Lys Tyr Lys Gly Phe Gln Val Ala Pro Ala Glu Leu Glu
        35                  40                  45

Ala Met Leu Ile Ala His Pro Ser Ile Ala Asp Ala Val Val Pro
    50                  55                  60

Leu Lys Asp Asp Ser Cys Gly Glu Ile Pro Val Ala Phe Val Val Thr
65                  70                  75                  80

Ser Gly Gly Ser Glu Ile Thr Glu Asp Glu Ile Lys Gln Tyr Val Ala
                85                  90                  95

Lys Gln Val Val Phe Tyr Lys Arg Leu His Lys Ile Phe Phe Val Glu
            100                 105                 110

Asp Ile Pro Lys Ala Pro Ser Gly Lys Ile Leu Arg Lys Asp Leu Arg
        115                 120                 125

Ala Lys Leu Ala Ser Gly Phe Ser Asn Gly Ser Ser Cys
    130                 135                 140

<210> SEQ ID NO 7
<211> LENGTH: 575
<212> TYPE: PRT
<213> ORGANISM: Saccharum

<400> SEQUENCE: 7

Met Ile Thr Val Ala Ala Pro Glu Ala Gln Ser Gln Val Ala Ala Ala
1               5                   10                  15

Ala Val Ala Pro Ala Pro Glu Glu Thr Val Phe Arg Ser Lys Leu
            20                  25                  30

Pro Asp Ile Asp Ile Pro Ser His Leu Pro Leu His Gly Tyr Cys Phe
        35                  40                  45

```
Ala Arg Ala Ala Glu Val Ala Asp Ala Pro Cys Leu Ile Ala Ala
    50                  55                  60

Thr Gly Arg Thr Tyr Thr Tyr Ala Glu Thr Arg Leu Leu Cys Arg Lys
65              70                  75                  80

Ala Ala Ala Ser Leu His Gly Leu Gly Val Gly Gln Gly Asp Cys Val
                85                  90                  95

Met Ile Leu Leu Gln Asn Ser Val Glu Phe Val Leu Thr Phe Phe Gly
            100                 105                 110

Ala Ser Phe Leu Gly Ala Val Thr Thr Ala Ala Asn Pro Phe Cys Thr
        115                 120                 125

Pro Leu Glu Ile His Lys Gln Phe Arg Ala Ser Gly Ser Lys Leu Ile
    130                 135                 140

Val Thr Gln Ser Ala Tyr Val Asp Lys Leu Arg His Glu Ala Phe Pro
145                 150                 155                 160

Arg Ile Gly Ala Ala Ser Asp Gly Gly Glu Asp Glu Asp Asn Ala Leu
                165                 170                 175

Thr Val Leu Thr Ile Asp Asp Ala Ala Ser Thr Pro Glu Gly Cys Leu
            180                 185                 190

Ala Phe Trp Glu Leu Val Thr Pro Ala Asp Ala Ala Leu Pro Glu
        195                 200                 205

Val Ser Ile Ser Pro Asp Asp Pro Val Ala Leu Pro Phe Ser Ser Gly
210                 215                 220

Thr Thr Gly Leu Pro Lys Gly Val Val Leu Thr His Gly Gly Gln Val
225                 230                 235                 240

Ser Asn Val Ala Gln Gln Val Asp Gly Ala Asn Pro Asn Leu Tyr Met
                245                 250                 255

Arg Glu Gly Asp Val Ala Leu Cys Val Leu Pro Leu Phe His Ile Phe
            260                 265                 270

Ser Leu Asn Ser Val Leu Leu Cys Ala Leu Arg Ala Gly Ala Ala Val
        275                 280                 285

Met Leu Met Pro Lys Phe Glu Met Gly Ala Met Leu Glu Gly Ile Gln
    290                 295                 300

Arg Trp Arg Val Thr Val Ala Ala Val Pro Pro Leu Val Leu Ala
305                 310                 315                 320

Leu Ala Lys Asp Pro Ala Leu Glu Lys Tyr Asp Leu Ser Ser Ile Arg
                325                 330                 335

Ile Val Leu Ser Gly Ala Ala Pro Leu Gly Lys Glu Leu Val Asp Ala
            340                 345                 350

Leu Arg Ala Arg Val Pro Gln Ala Val Phe Gly Gln Gly Tyr Gly Met
        355                 360                 365

Thr Glu Ala Gly Pro Val Leu Ser Met Cys Pro Ala Phe Ala Lys Glu
    370                 375                 380

Pro Thr Pro Ala Lys Pro Glu Ser Cys Gly Thr Val Val Arg Asn Ala
385                 390                 395                 400

Glu Leu Lys Val Val Asp Pro Asp Thr Gly Leu Ser Leu Ser Arg Asn
                405                 410                 415

Leu Pro Gly Glu Ile Cys Ile Arg Gly Pro Gln Ile Met Lys Gly Tyr
            420                 425                 430

Leu Asn Asp Pro Glu Ala Thr Ala Arg Thr Ile Asp Val Asp Gly Trp
        435                 440                 445

Leu His Thr Gly Asp Ile Gly Tyr Val Asp Asp Glu Glu Val Phe
    450                 455                 460
```

```
Ile Val Asp Arg Val Lys Glu Leu Ile Lys Phe Arg Gly Phe Gln Val
465                 470                 475                 480

Pro Pro Ala Glu Leu Glu Ala Leu Leu Ile Ala His Pro Ser Ile Ala
            485                 490                 495

Asp Ala Ala Val Val Pro Gln Lys Asp Asp Ala Ala Gly Glu Val Pro
            500                 505                 510

Val Ala Phe Val Val Arg Ala Thr Asp Ser Asp Ile Ala Glu Asp Ala
            515                 520                 525

Ile Lys Asp Phe Ile Ser Lys Gln Val Val Phe Tyr Lys Arg Leu Tyr
            530                 535                 540

Lys Val Tyr Phe Thr Pro Ser Ile Pro Lys Ser Ala Ser Gly Lys Ile
545                 550                 555                 560

Leu Arg Arg Glu Leu Arg Ala Lys Leu Ala Ala Ala Thr Thr
            565                 570                 575

<210> SEQ ID NO 8
<211> LENGTH: 554
<212> TYPE: PRT
<213> ORGANISM: Saccharum

<400> SEQUENCE: 8

Met Gly Ser Val Asp Thr Ala Val Ala Val Pro Val Pro Val Ala Glu
1               5                   10                  15

Pro Ala Glu Glu Lys Ala Val Val Phe Arg Ser Lys Leu Pro Asp
            20                  25                  30

Ile Glu Ile Asn Asn Ser Gln Ser Leu His Ala Tyr Cys Phe Gly Lys
            35                  40                  45

Met Ser Glu Val Ala Asp Arg Ala Cys Leu Val Asp Gly Gln Thr Gly
50                  55                  60

Ala Ser Tyr Thr Tyr Ala Glu Val Glu Ser Leu Ser Arg Arg Ala Ala
65                  70                  75                  80

Ser Gly Leu Arg Ala Met Gly Val Gly Lys Gly Asp Val Val Met Asn
            85                  90                  95

Leu Leu Arg Asn Cys Pro Glu Phe Ala Phe Thr Phe Phe Gly Ala Ala
            100                 105                 110

Arg Leu Gly Ala Ala Thr Thr Thr Ala Asn Pro Phe Tyr Thr Pro His
            115                 120                 125

Glu Ile His Arg Gln Ala Glu Ala Ala Gly Ala Lys Leu Ile Val Thr
            130                 135                 140

Glu Ala Cys Ala Val Glu Lys Val Arg Glu Phe Ala Ala Gly Arg Gly
145                 150                 155                 160

Val Pro Val Val Thr Val Asp Gly Arg Phe Asp Gly Cys Val Glu Phe
            165                 170                 175

Ala Glu Val Ile Ala Ala Glu Glu Leu Glu Ala Asp Val Asp Val His
            180                 185                 190

Pro Asp Asp Val Val Ala Leu Pro Tyr Ser Ser Gly Thr Thr Gly Leu
            195                 200                 205

Pro Lys Gly Val Met Leu Thr His Arg Ser Leu Ile Thr Ser Val Ala
            210                 215                 220

Gln Gln Val Asp Gly Glu Asn Pro Asn Leu Tyr Phe Ser Lys Asp Asp
225                 230                 235                 240

Val Leu Leu Cys Leu Leu Pro Leu Phe His Ile Tyr Ser Leu Asn Ser
            245                 250                 255

Val Leu Leu Ala Gly Leu Arg Ala Gly Ser Thr Ile Val Ile Met Arg
            260                 265                 270
```

```
Lys Phe Asp Leu Gly Ala Leu Val Asp Leu Val Arg Lys His Ala Ile
        275                 280                 285

Thr Ile Ala Pro Phe Val Pro Pro Ile Val Val Glu Ile Ala Lys Ser
        290                 295                 300

Pro Arg Val Thr Ala Ala Asp Leu Ala Ser Ile Arg Met Val Met Ser
305                 310                 315                 320

Gly Ala Ala Pro Met Gly Lys Glu Leu Gln Asp Ala Phe Met Thr Lys
                    325                 330                 335

Ile Pro Asn Ala Val Leu Gly Gln Gly Tyr Gly Met Thr Glu Ala Gly
                340                 345                 350

Pro Val Leu Ala Met Cys Leu Ala Phe Ala Lys Glu Pro Phe Gln Val
            355                 360                 365

Lys Ser Gly Ser Cys Gly Thr Val Val Arg Asn Ala Glu Leu Lys Ile
        370                 375                 380

Val Asp Pro Asp Thr Gly Ala Ala Leu Gly Arg Asn Gln Pro Gly Glu
385                 390                 395                 400

Ile Cys Ile Arg Gly Glu Gln Ile Met Lys Gly Tyr Leu Asn Asp Pro
                    405                 410                 415

Glu Ser Thr Lys Asn Thr Ile Asp Lys Gly Gly Trp Leu His Thr Gly
                420                 425                 430

Asp Ile Gly Tyr Val Asp Asp Asp Glu Ile Phe Ile Val Asp Arg
            435                 440                 445

Leu Lys Glu Ile Ile Lys Tyr Lys Gly Phe Gln Val Pro Pro Ala Glu
        450                 455                 460

Ile Glu Ala Leu Leu Ile Thr His Pro Glu Ile Lys Asp Ala Ala Val
465                 470                 475                 480

Val Ser Met Lys Asp Asp Leu Ala Gly Glu Ile Pro Val Ala Phe Ile
                    485                 490                 495

Val Arg Thr Glu Gly Ser Glu Val Thr Glu Asp Val Ile Lys Gln Phe
                500                 505                 510

Val Ala Lys Glu Val Val Phe Tyr Lys Lys Val His Lys Val Phe Phe
            515                 520                 525

Thr Glu Ser Ile Pro Lys Asn Pro Ser Gly Lys Ile Leu Arg Lys Asp
        530                 535                 540

Leu Arg Ala Arg Leu Ala Ala Ala Val His
545                 550

<210> SEQ ID NO 9
<211> LENGTH: 561
<212> TYPE: PRT
<213> ORGANISM: Arabidopsis thaliana

<400> SEQUENCE: 9

Met Ala Pro Gln Glu Gln Ala Val Ser Gln Val Met Glu Lys Gln Ser
1               5                   10                  15

Asn Asn Asn Asn Ser Asp Val Ile Phe Arg Ser Lys Leu Pro Asp Ile
                20                  25                  30

Tyr Ile Pro Asn His Leu Ser Leu His Asp Tyr Ile Phe Gln Asn Ile
            35                  40                  45

Ser Glu Phe Ala Thr Lys Pro Cys Leu Ile Asn Gly Pro Thr Gly His
        50                  55                  60

Val Tyr Thr Tyr Ser Asp Val His Val Ile Ser Arg Gln Ile Ala Ala
65                  70                  75                  80

Asn Phe His Lys Leu Gly Val Asn Gln Asn Asp Val Val Met Leu Leu
```

```
                    85                  90                  95
Leu Pro Asn Cys Pro Glu Phe Val Leu Ser Phe Leu Ala Ala Ser Phe
                100                 105                 110

Arg Gly Ala Thr Ala Thr Ala Ala Asn Pro Phe Phe Thr Pro Ala Glu
            115                 120                 125

Ile Ala Lys Gln Ala Lys Ala Ser Asn Thr Lys Leu Ile Ile Thr Glu
        130                 135                 140

Ala Arg Tyr Val Asp Lys Ile Lys Pro Leu Gln Asn Asp Asp Gly Val
145                 150                 155                 160

Val Ile Val Cys Ile Asp Asp Asn Glu Ser Val Pro Ile Pro Glu Gly
                165                 170                 175

Cys Leu Arg Phe Thr Glu Leu Thr Gln Ser Thr Thr Glu Ala Ser Glu
            180                 185                 190

Val Ile Asp Ser Val Glu Ile Ser Pro Asp Val Val Ala Leu Pro
        195                 200                 205

Tyr Ser Ser Gly Thr Thr Gly Leu Pro Lys Gly Val Met Leu Thr His
    210                 215                 220

Lys Gly Leu Val Thr Ser Val Ala Gln Gln Val Asp Gly Glu Asn Pro
225                 230                 235                 240

Asn Leu Tyr Phe His Ser Asp Asp Val Ile Leu Cys Val Leu Pro Met
                245                 250                 255

Phe His Ile Tyr Ala Leu Asn Ser Ile Met Leu Cys Gly Leu Arg Val
            260                 265                 270

Gly Ala Ala Ile Leu Ile Met Pro Lys Phe Glu Ile Asn Leu Leu Leu
        275                 280                 285

Glu Leu Ile Gln Arg Cys Lys Val Thr Val Ala Pro Met Val Pro Pro
    290                 295                 300

Ile Val Leu Ala Ile Ala Lys Ser Ser Glu Thr Glu Lys Tyr Asp Leu
305                 310                 315                 320

Ser Ser Ile Arg Val Val Lys Ser Gly Ala Ala Pro Leu Gly Lys Glu
                325                 330                 335

Leu Glu Asp Ala Val Asn Ala Lys Phe Pro Asn Ala Lys Leu Gly Gln
            340                 345                 350

Gly Tyr Gly Met Thr Glu Ala Gly Pro Val Leu Ala Met Ser Leu Gly
        355                 360                 365

Phe Ala Lys Glu Pro Phe Pro Val Lys Ser Gly Ala Cys Gly Thr Val
    370                 375                 380

Val Arg Asn Ala Glu Met Lys Ile Val Asp Pro Asp Thr Gly Asp Ser
385                 390                 395                 400

Leu Ser Arg Asn Gln Pro Gly Glu Ile Cys Ile Arg Gly His Gln Ile
                405                 410                 415

Met Lys Gly Tyr Leu Asn Asn Pro Ala Ala Thr Ala Glu Thr Ile Asp
            420                 425                 430

Lys Asp Gly Trp Leu His Thr Gly Asp Ile Gly Leu Ile Asp Asp Asp
        435                 440                 445

Asp Glu Leu Phe Ile Val Asp Arg Leu Lys Glu Leu Ile Lys Tyr Lys
    450                 455                 460

Gly Phe Gln Val Ala Pro Ala Glu Leu Glu Ala Leu Leu Ile Gly His
465                 470                 475                 480

Pro Asp Ile Thr Asp Val Ala Val Val Ala Met Lys Glu Glu Ala Ala
                485                 490                 495

Gly Glu Val Pro Val Ala Phe Val Val Lys Ser Lys Asp Ser Glu Leu
            500                 505                 510
```

```
Ser Glu Asp Asp Val Lys Gln Phe Val Ser Lys Gln Val Val Phe Tyr
        515                 520                 525

Lys Arg Ile Asn Lys Val Phe Phe Thr Glu Ser Ile Pro Lys Ala Pro
        530                 535                 540

Ser Gly Lys Ile Leu Arg Lys Asp Leu Arg Ala Lys Leu Ala Asn Gly
545                 550                 555                 560

Leu

<210> SEQ ID NO 10
<211> LENGTH: 556
<212> TYPE: PRT
<213> ORGANISM: Arabidopsis thaliana

<400> SEQUENCE: 10

Met Thr Thr Gln Asp Val Ile Val Asn Asp Gln Asn Asp Gln Lys Gln
1               5                   10                  15

Cys Ser Asn Asp Val Ile Phe Arg Ser Arg Leu Pro Asp Ile Tyr Ile
            20                  25                  30

Pro Asn His Leu Pro Leu His Asp Tyr Ile Phe Glu Asn Ile Ser Glu
        35                  40                  45

Phe Ala Ala Lys Pro Cys Leu Ile Asn Gly Pro Thr Gly Glu Val Tyr
    50                  55                  60

Thr Tyr Ala Asp Val His Val Thr Ser Arg Lys Leu Ala Ala Gly Leu
65                  70                  75                  80

His Asn Leu Gly Val Lys Gln His Asp Val Val Met Ile Leu Leu Pro
                85                  90                  95

Asn Ser Pro Glu Val Val Leu Thr Phe Leu Ala Ala Ser Phe Ile Gly
            100                 105                 110

Ala Ile Thr Thr Ser Ala Asn Pro Phe Phe Thr Pro Ala Glu Ile Ser
        115                 120                 125

Lys Gln Ala Lys Ala Ser Ala Ala Lys Leu Ile Val Thr Gln Ser Arg
    130                 135                 140

Tyr Val Asp Lys Ile Lys Asn Leu Gln Asn Asp Gly Val Leu Ile Val
145                 150                 155                 160

Thr Thr Asp Ser Asp Ala Ile Pro Glu Asn Cys Leu Arg Phe Ser Glu
                165                 170                 175

Leu Thr Gln Ser Glu Glu Pro Arg Val Asp Ser Ile Pro Glu Lys Ile
            180                 185                 190

Ser Pro Glu Asp Val Val Ala Leu Pro Phe Ser Ser Gly Thr Thr Gly
        195                 200                 205

Leu Pro Lys Gly Val Met Leu Thr His Lys Gly Leu Val Thr Ser Val
    210                 215                 220

Ala Gln Gln Val Asp Gly Glu Asn Pro Asn Leu Tyr Phe Asn Arg Asp
225                 230                 235                 240

Asp Val Ile Leu Cys Val Leu Pro Met Phe His Ile Tyr Ala Leu Asn
                245                 250                 255

Ser Ile Met Leu Cys Ser Leu Arg Val Gly Ala Thr Ile Leu Ile Met
            260                 265                 270

Pro Lys Phe Glu Ile Thr Leu Leu Leu Glu Gln Ile Gln Arg Cys Lys
        275                 280                 285

Val Thr Val Ala Met Val Val Pro Pro Ile Val Leu Ala Ile Ala Lys
    290                 295                 300

Ser Pro Glu Thr Glu Lys Tyr Asp Leu Ser Ser Val Arg Met Val Lys
305                 310                 315                 320
```

Ser Gly Ala Ala Pro Leu Gly Lys Glu Leu Glu Asp Ala Ile Ser Ala
            325                 330                 335

Lys Phe Pro Asn Ala Lys Leu Gly Gln Gly Tyr Gly Met Thr Glu Ala
            340                 345                 350

Gly Pro Val Leu Ala Met Ser Leu Gly Phe Ala Lys Glu Pro Phe Pro
            355                 360                 365

Val Lys Ser Gly Ala Cys Gly Thr Val Val Arg Asn Ala Glu Met Lys
            370                 375                 380

Ile Leu Asp Pro Asp Thr Gly Asp Ser Leu Pro Arg Asn Lys Pro Gly
385                 390                 395                 400

Glu Ile Cys Ile Arg Gly Asn Gln Ile Met Lys Gly Tyr Leu Asn Asp
            405                 410                 415

Pro Leu Ala Thr Ala Ser Thr Ile Asp Lys Asp Gly Trp Leu His Thr
            420                 425                 430

Gly Asp Val Gly Phe Ile Asp Asp Asp Glu Leu Phe Ile Val Asp
            435                 440                 445

Arg Leu Lys Glu Leu Ile Lys Tyr Lys Gly Phe Gln Val Ala Pro Ala
            450                 455                 460

Glu Leu Glu Ser Leu Leu Ile Gly His Pro Glu Ile Asn Asp Val Ala
465                 470                 475                 480

Val Val Ala Met Lys Glu Glu Asp Ala Gly Glu Val Pro Val Ala Phe
            485                 490                 495

Val Val Arg Ser Lys Asp Ser Asn Ile Ser Glu Asp Glu Ile Lys Gln
            500                 505                 510

Phe Val Ser Lys Gln Val Val Phe Tyr Lys Arg Ile Asn Lys Val Phe
            515                 520                 525

Phe Thr Asp Ser Ile Pro Lys Ala Pro Ser Gly Lys Ile Leu Arg Lys
            530                 535                 540

Asp Leu Arg Ala Arg Leu Ala Asn Gly Leu Met Asn
545                 550                 555

<210> SEQ ID NO 11
<211> LENGTH: 560
<212> TYPE: PRT
<213> ORGANISM: Arabidopsis thaliana

<400> SEQUENCE: 11

Met Ile Thr Ala Ala Leu His Glu Pro Gln Ile His Lys Pro Thr Asp
1               5                   10                  15

Thr Ser Val Val Ser Asp Asp Val Leu Pro His Ser Pro Pro Thr Pro
            20                  25                  30

Arg Ile Phe Arg Ser Lys Leu Pro Asp Ile Asp Ile Pro Asn His Leu
            35                  40                  45

Pro Leu His Thr Tyr Cys Phe Glu Lys Leu Ser Ser Val Ser Asp Lys
        50                  55                  60

Pro Cys Leu Ile Val Gly Ser Thr Gly Lys Ser Tyr Thr Tyr Gly Glu
65                  70                  75                  80

Thr His Leu Ile Cys Arg Arg Val Ala Ser Gly Leu Tyr Lys Leu Gly
            85                  90                  95

Ile Arg Lys Gly Asp Val Ile Met Ile Leu Leu Gln Asn Ser Ala Glu
            100                 105                 110

Phe Val Phe Ser Phe Met Gly Ala Ser Met Ile Gly Ala Val Ser Thr
            115                 120                 125

Thr Ala Asn Pro Phe Tyr Thr Ser Gln Glu Leu Tyr Lys Gln Leu Lys

-continued

```
            130                 135                 140
Ser Ser Gly Ala Lys Leu Ile Ile Thr His Ser Gln Tyr Val Asp Lys
145                 150                 155                 160

Leu Lys Asn Leu Gly Glu Asn Leu Thr Leu Ile Thr Thr Asp Glu Pro
                    165                 170                 175

Thr Pro Glu Asn Cys Leu Pro Phe Ser Thr Leu Ile Thr Asp Asp Glu
                180                 185                 190

Thr Asn Pro Phe Gln Glu Thr Val Asp Ile Gly Gly Asp Asp Ala Ala
            195                 200                 205

Ala Leu Pro Phe Ser Ser Gly Thr Thr Gly Leu Pro Lys Gly Val Val
        210                 215                 220

Leu Thr His Lys Ser Leu Ile Thr Ser Val Ala Gln Gln Val Asp Gly
225                 230                 235                 240

Asp Asn Pro Asn Leu Tyr Leu Lys Ser Asn Asp Val Ile Leu Cys Val
                    245                 250                 255

Leu Pro Leu Phe His Ile Tyr Ser Leu Asn Ser Val Leu Leu Asn Ser
                260                 265                 270

Leu Arg Ser Gly Ala Thr Val Leu Leu Met His Lys Phe Glu Ile Gly
            275                 280                 285

Ala Leu Leu Asp Leu Ile Gln Arg His Arg Val Thr Ile Ala Ala Leu
        290                 295                 300

Val Pro Pro Leu Val Ile Ala Leu Ala Lys Asn Pro Thr Val Asn Ser
305                 310                 315                 320

Tyr Asp Leu Ser Ser Val Arg Phe Val Leu Ser Gly Ala Ala Pro Leu
                    325                 330                 335

Gly Lys Glu Leu Gln Asp Ser Leu Arg Arg Arg Leu Pro Gln Ala Ile
                340                 345                 350

Leu Gly Gln Gly Tyr Gly Met Thr Glu Ala Gly Pro Val Leu Ser Met
            355                 360                 365

Ser Leu Gly Phe Ala Lys Glu Pro Ile Pro Thr Lys Ser Gly Ser Cys
        370                 375                 380

Gly Thr Val Val Arg Asn Ala Glu Leu Lys Val Val His Leu Glu Thr
385                 390                 395                 400

Arg Leu Ser Leu Gly Tyr Asn Gln Pro Gly Glu Ile Cys Ile Arg Gly
                    405                 410                 415

Gln Gln Ile Met Lys Glu Tyr Leu Asn Asp Pro Glu Ala Thr Ser Ala
                420                 425                 430

Thr Ile Asp Glu Glu Gly Trp Leu His Thr Gly Asp Ile Gly Tyr Val
            435                 440                 445

Asp Glu Asp Asp Glu Ile Phe Ile Val Asp Arg Leu Lys Glu Val Ile
        450                 455                 460

Lys Phe Lys Gly Phe Gln Val Pro Pro Ala Glu Leu Glu Ser Leu Leu
465                 470                 475                 480

Ile Asn His His Ser Ile Ala Asp Ala Ala Val Val Pro Gln Asn Asp
                    485                 490                 495

Glu Val Ala Gly Glu Val Pro Val Ala Phe Val Val Arg Ser Asn Gly
                500                 505                 510

Asn Asp Ile Thr Glu Glu Asp Val Lys Glu Tyr Val Ala Lys Gln Val
            515                 520                 525

Val Phe Tyr Lys Arg Leu His Lys Val Phe Phe Val Ala Ser Ile Pro
        530                 535                 540

Lys Ser Pro Ser Gly Lys Ile Leu Arg Lys Asp Leu Lys Ala Lys Leu
545                 550                 555                 560
```

<210> SEQ ID NO 12
<211> LENGTH: 570
<212> TYPE: PRT
<213> ORGANISM: Arabidopsis thaliana

<400> SEQUENCE: 12

```
Met Val Leu Gln Gln Gln Thr His Phe Leu Thr Lys Lys Ile Asp Gln
1               5                   10                  15

Glu Asp Glu Glu Glu Pro Ser His Asp Phe Ile Phe Arg Ser Lys
            20                  25                  30

Leu Pro Asp Ile Phe Ile Pro Asn His Leu Pro Leu Thr Asp Tyr Val
            35                  40                  45

Phe Gln Arg Phe Ser Gly Asp Gly Asp Ser Ser Thr Thr Cys
        50                  55                  60

Ile Ile Asp Gly Ala Thr Gly Arg Ile Leu Thr Tyr Ala Asp Val Gln
65                  70                  75                  80

Thr Asn Met Arg Arg Ile Ala Ala Gly Ile His Arg Leu Gly Ile Arg
                85                  90                  95

His Gly Asp Val Val Met Leu Leu Leu Pro Asn Ser Pro Glu Phe Ala
            100                 105                 110

Leu Ser Phe Leu Ala Val Ala Tyr Leu Gly Ala Val Ser Thr Thr Ala
        115                 120                 125

Asn Pro Phe Tyr Thr Gln Pro Glu Ile Ala Lys Gln Ala Lys Ala Ser
    130                 135                 140

Ala Ala Lys Met Ile Ile Thr Lys Lys Cys Leu Val Asp Lys Leu Thr
145                 150                 155                 160

Asn Leu Lys Asn Asp Gly Val Leu Ile Val Cys Leu Asp Asp Asp Gly
                165                 170                 175

Asp Asn Gly Val Val Ser Ser Asp Asp Gly Cys Val Ser Phe Thr
            180                 185                 190

Glu Leu Thr Gln Ala Asp Glu Thr Glu Leu Leu Lys Pro Lys Ile Ser
        195                 200                 205

Pro Glu Asp Thr Val Ala Met Pro Tyr Ser Ser Gly Thr Thr Gly Leu
    210                 215                 220

Pro Lys Gly Val Met Ile Thr His Lys Gly Leu Val Thr Ser Ile Ala
225                 230                 235                 240

Gln Lys Val Asp Gly Glu Asn Pro Asn Leu Asn Phe Thr Ala Asn Asp
                245                 250                 255

Val Ile Leu Cys Phe Leu Pro Met Phe His Ile Tyr Ala Leu Asp Ala
            260                 265                 270

Leu Met Leu Ser Ala Met Arg Thr Gly Ala Ala Leu Leu Ile Val Pro
        275                 280                 285

Arg Phe Glu Leu Asn Leu Val Met Glu Leu Ile Gln Arg Tyr Lys Val
    290                 295                 300

Thr Val Val Pro Val Ala Pro Pro Val Val Leu Ala Phe Ile Lys Ser
305                 310                 315                 320

Pro Glu Thr Glu Arg Tyr Asp Leu Ser Ser Val Arg Ile Met Leu Ser
                325                 330                 335

Gly Ala Ala Thr Leu Lys Lys Glu Leu Glu Asp Ala Val Arg Leu Lys
            340                 345                 350

Phe Pro Asn Ala Ile Phe Gly Gln Gly Tyr Gly Met Thr Glu Ser Gly
        355                 360                 365

Thr Val Ala Lys Ser Leu Ala Phe Ala Lys Asn Pro Phe Lys Thr Lys
```

-continued

```
            370                 375                 380
Ser Gly Ala Cys Gly Thr Val Ile Arg Asn Ala Glu Met Lys Val Val
385                 390                 395                 400

Asp Thr Glu Thr Gly Ile Ser Leu Pro Arg Asn Lys Ser Gly Glu Ile
                405                 410                 415

Cys Val Arg Gly His Gln Leu Met Lys Gly Tyr Leu Asn Asp Pro Glu
            420                 425                 430

Ala Thr Ala Arg Thr Ile Asp Lys Asp Gly Trp Leu His Thr Gly Asp
            435                 440                 445

Ile Gly Phe Val Asp Asp Asp Glu Ile Phe Ile Val Asp Arg Leu
        450                 455                 460

Lys Glu Leu Ile Lys Phe Lys Gly Tyr Gln Val Ala Pro Ala Glu Leu
465                 470                 475                 480

Glu Ala Leu Leu Ile Ser His Pro Ser Ile Asp Asp Ala Val Val
                485                 490                 495

Ala Met Lys Asp Glu Val Ala Asp Glu Val Pro Val Ala Phe Val Ala
                500                 505                 510

Arg Ser Gln Gly Ser Gln Leu Thr Glu Asp Asp Val Lys Ser Tyr Val
                515                 520                 525

Asn Lys Gln Val Val His Tyr Lys Arg Ile Lys Met Val Phe Phe Ile
            530                 535                 540

Glu Val Ile Pro Lys Ala Val Ser Gly Lys Ile Leu Arg Lys Asp Leu
545                 550                 555                 560

Arg Ala Lys Leu Glu Thr Met Cys Ser Lys
                565                 570

<210> SEQ ID NO 13
<211> LENGTH: 557
<212> TYPE: PRT
<213> ORGANISM: Poplar

<400> SEQUENCE: 13

Met Glu Ala Lys Asn Asp Gln Ala Gln Glu Phe Ile Phe Arg Ser Lys
1               5                   10                  15

Leu Pro Asp Ile His Ile Pro Asn His Leu Pro Leu His Thr Tyr Cys
            20                  25                  30

Phe Glu Asn Leu Ser Arg Phe Lys Asp Asn Pro Cys Leu Ile Asn Gly
        35                  40                  45

Pro Thr Gly Glu Ile His Thr Tyr Ala Glu Val Glu Leu Thr Ser Arg
    50                  55                  60

Lys Val Ala Ser Gly Leu Asn Lys Leu Gly Ile Lys Gln Gly Asp Val
65                  70                  75                  80

Ile Leu Leu Leu Leu Gln Asn Ser Pro Glu Phe Val Phe Ala Phe Leu
                85                  90                  95

Gly Ala Ser Ile Ile Gly Ala Ile Ser Thr Thr Ala Asn Pro Phe Tyr
            100                 105                 110

Thr Pro Ala Glu Val Ala Lys Gln Ala Thr Ala Ser Lys Ala Lys Leu
            115                 120                 125

Ile Ile Thr Gln Ala Val Tyr Ala Glu Lys Val Gln Glu Phe Val Lys
        130                 135                 140

Glu Asn Val His Val Lys Ile Val Thr Val Asp Ser Pro Pro Glu Asn
145                 150                 155                 160

Tyr Leu His Phe Ser Glu Leu Thr Asn Ser Asp Glu Asp Ile Pro
                165                 170                 175
```

-continued

```
Ala Val Glu Ile Asn Pro Asp Asp Val Val Ala Leu Pro Tyr Ser Ser
            180                 185                 190

Gly Thr Thr Gly Leu Pro Lys Gly Val Met Leu Thr His Lys Gly Leu
        195                 200                 205

Val Thr Ser Val Ala Gln Gln Val Asp Gly Glu Asn Pro Asn Leu Tyr
    210                 215                 220

Phe His Glu Lys Asp Val Ile Leu Cys Val Leu Pro Leu Phe His Ile
225                 230                 235                 240

Tyr Ser Leu Asn Ser Val Leu Cys Gly Leu Arg Val Gly Ser Ala
                245                 250                 255

Ile Leu Leu Met Gln Lys Phe Glu Ile Val Thr Leu Met Glu Leu Val
            260                 265                 270

Gln Lys Tyr Lys Val Thr Ile Ala Pro Phe Val Pro Val Val Leu
        275                 280                 285

Ala Val Ala Lys Cys Pro Val Val Asp Lys Tyr Asp Leu Ser Ser Ile
    290                 295                 300

Arg Thr Val Met Ser Gly Ala Ala Pro Met Gly Lys Glu Leu Glu Asp
305                 310                 315                 320

Thr Val Arg Ala Lys Leu Pro Asn Ala Lys Leu Gly Gln Gly Tyr Gly
                325                 330                 335

Met Thr Glu Ala Gly Pro Val Leu Ser Met Cys Leu Ala Phe Ala Lys
            340                 345                 350

Glu Pro Phe Glu Ile Lys Ser Gly Ala Cys Gly Thr Val Val Arg Asn
        355                 360                 365

Ala Glu Met Lys Ile Val Asp Pro Asp Thr Gly Arg Ser Leu Pro Arg
    370                 375                 380

Asn Gln Ser Gly Glu Ile Cys Ile Arg Gly Ser Gln Ile Met Lys Gly
385                 390                 395                 400

Tyr Leu Asn Asp Pro Glu Ala Thr Glu Arg Thr Val Asp Asn Asp Gly
                405                 410                 415

Trp Leu His Thr Gly Asp Ile Gly Tyr Ile Asp Gly Asp Glu Leu
            420                 425                 430

Phe Ile Val Asp Arg Leu Lys Glu Leu Ile Lys Tyr Lys Gly Phe Gln
        435                 440                 445

Val Ala Pro Ala Glu Leu Glu Ala Met Leu Ile Ala His Pro Asp Ile
    450                 455                 460

Ser Asp Cys Ala Val Val Pro Met Lys Asp Glu Ala Ala Gly Glu Val
465                 470                 475                 480

Pro Ile Ala Phe Val Val Arg Ala Asn Gly Ser Lys Ile Thr Glu Asp
                485                 490                 495

Glu Ile Lys Gln Tyr Ile Ser Lys Gln Val Val Phe Tyr Lys Arg Ile
            500                 505                 510

Ser Arg Val Phe Phe Thr Glu Ala Ile Pro Lys Ala Pro Ser Gly Lys
        515                 520                 525

Ile Leu Arg Lys Asp Leu Arg Ala Arg Leu Ala Thr Gly Asp Phe Leu
    530                 535                 540

Ile Lys Phe Gln His Asp Thr Tyr Met Gln Lys Gln Gln
545                 550                 555
```

<210> SEQ ID NO 14
<211> LENGTH: 548
<212> TYPE: PRT
<213> ORGANISM: Poplar

<400> SEQUENCE: 14

-continued

```
Met Glu Ala Asn Lys Asp Gln Val Gln Glu Phe Ile Phe Arg Ser Lys
1               5                   10                  15

Leu Pro Asp Ile Tyr Ile Pro Asn His Leu Pro Leu His Thr Tyr Cys
            20                  25                  30

Phe Glu Lys Leu Ser Gln Phe Lys Asp Asn Pro Cys Leu Ile Asn Gly
        35                  40                  45

Pro Thr Gly Asp Ile Tyr Thr Tyr Ala Asp Val Glu Leu Thr Ser Arg
    50                  55                  60

Lys Val Ala Ser Gly Leu Tyr Lys Leu Gly Leu Gln Gln Gly Asp Val
65                  70                  75                  80

Ile Leu Leu Leu Leu Gln Asn Ser Pro Glu Phe Val Phe Ala Phe Leu
                85                  90                  95

Gly Ala Ser Phe Ile Gly Ala Ile Ser Ser Thr Ala Asn Pro Phe Tyr
                100                 105                 110

Thr Ser Ala Glu Ile Ala Lys Gln Ala Thr Ala Ser Lys Ala Lys Leu
        115                 120                 125

Ile Ile Thr His Ala Ala Tyr Ala Glu Lys Val Gln Gln Phe Ala Gln
        130                 135                 140

Glu Asn Asp His Val Lys Ile Met Thr Ile Asp Ser Leu Thr Glu Asn
145                 150                 155                 160

Cys Leu His Phe Ser Glu Leu Thr Ser Ser Asp Glu Asn Glu Ile Pro
                165                 170                 175

Thr Val Lys Ile Lys Pro Asp Asp Ile Met Ala Leu Pro Tyr Ser Ser
                180                 185                 190

Gly Thr Thr Gly Leu Pro Lys Gly Val Met Leu Thr His Lys Gly Leu
                195                 200                 205

Val Thr Ser Val Ala Gln Gln Val Asp Gly Glu Asn Pro Asn Leu Tyr
        210                 215                 220

Phe His Glu Arg Asp Val Ile Leu Cys Val Leu Pro Leu Phe His Ile
225                 230                 235                 240

Tyr Ser Leu Asn Ser Val Phe Leu Cys Gly Leu Arg Ala Gly Ser Ala
                245                 250                 255

Ile Leu Val Met Gln Lys Phe Asp Thr Val Ser Leu Met Asp Leu Val
                260                 265                 270

Gln Lys Tyr Lys Val Thr Ile Ala Pro Leu Val Pro Pro Ile Cys Leu
        275                 280                 285

Ala Ile Ala Lys Ser Pro Val Val Asp Gln Tyr Asp Leu Ser Ser Ile
        290                 295                 300

Arg Thr Val Leu Ser Gly Ala Ala Pro Leu Gly Lys Glu Leu Glu Asp
305                 310                 315                 320

Thr Val Arg Ala Lys Leu Pro Asn Ala Lys Leu Gly Gln Gly Tyr Gly
                325                 330                 335

Met Thr Glu Ala Gly Pro Val Ile Ala Met Cys Leu Ala Phe Ala Lys
        340                 345                 350

Glu Pro Phe Glu Ile Lys Ser Gly Ala Cys Gly Thr Val Val Arg Asn
        355                 360                 365

Ala Glu Met Lys Ile Val Asp Pro Glu Thr Gly Glu Ser Gln Pro Arg
    370                 375                 380

Asn Lys Thr Gly Glu Ile Cys Ile Arg Gly Cys Gln Ile Met Lys Gly
385                 390                 395                 400

Tyr Leu Asn Asp Pro Glu Ala Thr Glu Arg Thr Ile Asp Lys Asp Gly
                405                 410                 415
```

```
Trp Leu His Thr Gly Asp Ile Gly Tyr Ile Asp Glu Leu Phe
            420                 425                 430

Ile Val Asp Arg Leu Lys Glu Leu Ile Lys Tyr Lys Gly Phe Gln Val
            435                 440                 445

Ala Pro Ala Glu Leu Glu Ala Met Leu Ile Ala His Pro Asn Ile Ser
450                         455                 460

Asp Ala Ala Val Val Pro Met Lys Asp Glu Ala Ala Gly Glu Val Pro
465                 470                 475                 480

Val Ala Phe Val Val Arg Ser Asn Gly Ser Lys Ile Thr Glu Asp Glu
                    485                 490                 495

Ile Lys Gln Tyr Ile Ser Lys Gln Val Ile Phe Tyr Lys Arg Ile Gly
            500                 505                 510

Arg Val Phe Phe Thr Glu Ala Ile Pro Lys Ala Pro Ser Gly Lys Ile
            515                 520                 525

Leu Arg Lys Asp Leu Arg Ala Arg Val Ser Ala Gly Asp Leu Pro Cys
            530                 535                 540

Thr Ser Asp Ser
545

<210> SEQ ID NO 15
<211> LENGTH: 540
<212> TYPE: PRT
<213> ORGANISM: Poplar

<400> SEQUENCE: 15

Met Asp Ala Ile Met Asn Ser Gln Glu Glu Phe Ile Phe Arg Ser Lys
1               5                   10                  15

Leu Pro Asp Ile Tyr Ile Pro Lys Asn Leu Pro Leu His Ser Tyr Val
            20                  25                  30

Leu Glu Asn Leu Ser Lys Tyr Ser Lys Pro Cys Leu Ile Asn Gly
            35                  40                  45

Ala Asn Gly Asp Val Tyr Thr Tyr Ala Asp Val Glu Leu Thr Ala Arg
50                  55                  60

Arg Val Ala Ser Gly Leu Asn Lys Ile Gly Ile Gln Gln Gly Asp Val
65                  70                  75                  80

Ile Met Leu Phe Leu Pro Ser Ser Pro Glu Phe Val Leu Ala Phe Leu
                85                  90                  95

Gly Ala Ser His Arg Gly Ala Ile Val Thr Ala Ala Asn Pro Phe Ser
            100                 105                 110

Thr Pro Ala Glu Leu Ala Lys His Ala Lys Pro Pro Arg Thr Lys Leu
            115                 120                 125

Leu Ile Thr Gln Ala Cys Tyr Tyr Asp Lys Val Lys Asp Phe Ala Arg
130                 135                 140

Glu Ser Asp Val Lys Val Met Cys Val Asp Ser Ala Pro Asp Gly Cys
145                 150                 155                 160

Leu His Phe Ser Glu Leu Thr Gln Ala Asp Glu Asn Glu Val Pro Gln
            165                 170                 175

Val Asp Phe Ser Pro Asp Asp Val Val Ala Leu Pro Tyr Ser Ser Gly
            180                 185                 190

Thr Thr Gly Leu Pro Lys Gly Val Met Leu Thr His Lys Gly Leu Ile
            195                 200                 205

Thr Ser Val Ala Gln Gln Val Asp Gly Asp Asn Pro Asn Leu Tyr Phe
210                 215                 220

His Ser Glu Asp Val Ile Leu Cys Val Leu Pro Met Phe His Ile Tyr
225                 230                 235                 240
```

```
Ala Leu Asn Ser Ile Met Leu Cys Gly Leu Arg Val Gly Ala Ser Ile
                245                 250                 255

Leu Ile Met Pro Lys Phe Asp Ile Gly Thr Leu Leu Gly Leu Ile Glu
            260                 265                 270

Lys Tyr Lys Val Ser Ile Ala Pro Val Val Pro Val Met Leu Ala
        275                 280                 285

Ile Ala Lys Ser Pro Asp Phe Asp Lys His Asp Leu Ser Ser Leu Arg
        290                 295                 300

Met Ile Lys Ser Gly Gly Ala Pro Leu Gly Lys Glu Leu Glu Asp Thr
305                 310                 315                 320

Val Arg Ala Lys Phe Pro Gln Ala Arg Leu Gly Gln Gly Tyr Gly Met
                325                 330                 335

Thr Glu Ala Gly Pro Val Leu Ala Met Cys Leu Ala Phe Ala Lys Glu
            340                 345                 350

Pro Phe Asp Ile Lys Pro Gly Ala Cys Gly Thr Val Val Arg Asn Ala
        355                 360                 365

Glu Met Lys Ile Val Asp Pro Glu Thr Gly Ala Ser Leu Arg Arg Asn
        370                 375                 380

Gln Pro Gly Glu Ile Cys Ile Arg Gly Asp Gln Ile Met Lys Gly Tyr
385                 390                 395                 400

Leu Asn Asp Pro Glu Ala Thr Ser Arg Thr Ile Asp Lys Glu Gly Trp
                405                 410                 415

Leu His Thr Gly Asp Ile Gly Tyr Ile Asp Asp Asp Glu Leu Phe
            420                 425                 430

Ile Val Asp Arg Leu Lys Glu Leu Ile Lys Tyr Lys Gly Phe Gln Val
        435                 440                 445

Ala Pro Ala Glu Leu Glu Ala Leu Leu Leu Ala His Pro Gln Ile Ser
450                 455                 460

Asp Ala Ala Val Val Gly Met Lys Asp Glu Asp Ala Gly Glu Val Pro
465                 470                 475                 480

Val Ala Phe Val Val Lys Ser Glu Lys Ser Gln Ala Thr Glu Asp Glu
                485                 490                 495

Ile Lys Gln Tyr Ile Ser Lys Gln Val Ile Phe Tyr Lys Arg Ile Lys
            500                 505                 510

Arg Val Phe Phe Ile Glu Ala Ile Pro Lys Ala Pro Ser Gly Lys Ile
        515                 520                 525

Leu Arg Lys Asn Leu Arg Glu Thr Leu Pro Gly Ile
        530                 535                 540

<210> SEQ ID NO 16
<211> LENGTH: 579
<212> TYPE: PRT
<213> ORGANISM: Poplar

<400> SEQUENCE: 16

Met Met Ser Val Ala Thr Val Glu Pro Pro Lys Pro Glu Leu Ser Pro
1               5                   10                  15

Pro Gln Asn Gln Asn Ala Pro Ser Ser His Glu Thr Asp His Ile Phe
            20                  25                  30

Arg Ser Lys Leu Pro Asp Ile Thr Ile Ser Asn His Leu Pro Leu His
        35                  40                  45

Ala Tyr Cys Phe Glu Asn Leu Ser Asp Phe Ser Asp Arg Pro Cys Leu
    50                  55                  60

Ile Ser Gly Ser Thr Gly Lys Thr Tyr Ser Phe Ala Glu Thr His Leu
```

```
                65                  70                  75                  80
        Ile Ser Arg Lys Val Ala Gly Leu Ser Asn Leu Gly Ile Lys Lys
                            85                  90                  95

Gly Asp Val Ile Met Thr Leu Leu Gln Asn Cys Pro Glu Phe Val Phe
                        100                 105                 110

Ser Phe Met Gly Ala Ser Met Ile Gly Ala Val Thr Thr Val Asn
                    115                 120                 125

Pro Phe Tyr Thr Pro Gly Glu Ile Phe Lys Gln Phe Ser Ala Ser Arg
                130                 135                 140

Ala Lys Leu Ile Ile Thr Gln Ser Gln His Val Asn Lys Leu Arg Asp
        145                 150                 155                 160

Ser Asp Tyr His Glu Asn Asn Gln Lys Pro Glu Glu Asp Phe Ile Val
                        165                 170                 175

Ile Thr Ile Asp Asp Pro Pro Glu Asn Cys Leu His Phe Asn Val Leu
                    180                 185                 190

Val Glu Ala Asn Glu Ser Glu Met Pro Thr Val Ser Ile His Pro Asp
                195                 200                 205

Asp Pro Val Ala Leu Pro Phe Ser Ser Gly Thr Thr Gly Leu Pro Lys
        210                 215                 220

Gly Val Ile Leu Thr His Lys Ser Leu Ile Thr Ser Val Ala Gln Gln
        225                 230                 235                 240

Val Asp Gly Glu Ile Pro Asn Leu Tyr Leu Lys Gln Asp Asp Val Val
                        245                 250                 255

Leu Cys Val Leu Pro Leu Phe His Ile Phe Ser Leu Asn Ser Val Leu
                    260                 265                 270

Leu Cys Ser Leu Arg Ala Gly Ser Ala Val Leu Leu Met Gln Lys Phe
                275                 280                 285

Glu Ile Gly Ser Leu Leu Glu Leu Ile Gln Lys His Asn Val Ser Val
            290                 295                 300

Ala Ala Val Val Pro Pro Leu Val Leu Ala Leu Ala Lys Asn Pro Met
        305                 310                 315                 320

Val Ala Asn Phe Asp Leu Ser Ser Ile Arg Val Val Leu Ser Gly Ala
                        325                 330                 335

Ala Pro Leu Gly Lys Glu Leu Glu Glu Ala Leu Arg Ser Arg Val Pro
                    340                 345                 350

Gln Ala Ile Leu Gly Gln Gly Tyr Gly Met Thr Glu Ala Gly Pro Val
                355                 360                 365

Leu Ser Met Cys Leu Ala Phe Ser Lys Gln Pro Leu Pro Thr Lys Ser
        370                 375                 380

Gly Ser Cys Gly Thr Val Val Arg Asn Ala Glu Leu Lys Val Ile Asp
        385                 390                 395                 400

Pro Glu Thr Gly Ser Ser Leu Gly Arg Asn Gln Pro Gly Glu Ile Cys
                        405                 410                 415

Ile Arg Gly Ser Gln Ile Met Lys Gly Tyr Leu Asn Asp Ala Glu Ala
                    420                 425                 430

Thr Ala Asn Ile Ile Asp Val Glu Gly Trp Leu His Thr Gly Asp Ile
                435                 440                 445

Gly Tyr Val Asp Asp Asp Glu Ile Phe Ile Val Asp Arg Val Lys
        450                 455                 460

Glu Ile Ile Lys Phe Lys Gly Phe Gln Val Pro Pro Ala Glu Leu Glu
        465                 470                 475                 480

Ala Leu Leu Val Asn His Pro Ser Ile Ala Asp Ala Val Val Pro
                        485                 490                 495
```

```
Arg Asp Asn Leu Tyr Gly Asn Asn Arg Gln Lys Asp Glu Val Ala Gly
                500                 505                 510

Glu Val Pro Val Ala Phe Val Val Arg Ser Asn Asp Leu Asp Leu Asn
            515                 520                 525

Glu Glu Ala Val Lys Asp Tyr Ile Ala Lys Gln Val Val Phe Tyr Lys
        530                 535                 540

Lys Leu His Lys Val Phe Phe Val His Ser Ile Pro Lys Ser Ala Ser
545                 550                 555                 560

Gly Lys Ile Leu Arg Lys Asp Leu Arg Ala Lys Leu Ala Thr Ala Thr
                565                 570                 575

Thr Met Ser

<210> SEQ ID NO 17
<211> LENGTH: 22
<212> TYPE: DNA
<213> ORGANISM: Artificial Sequence
<220> FEATURE:
<223> OTHER INFORMATION: gene specific primer based on the partial
      genomic DNA sequence of 4CL-L

<400> SEQUENCE: 17
cgttgcctgt gaagtccggc gc                                          22

<210> SEQ ID NO 18
<211> LENGTH: 23
<212> TYPE: DNA
<213> ORGANISM: Artificial Sequence
<220> FEATURE:
<223> OTHER INFORMATION: gene specific primer based on the partial
      genomic DNA sequence of 4CL-L

<400> SEQUENCE: 18
ccacggcgaa gaccatcgac tcg                                         23

<210> SEQ ID NO 19
<211> LENGTH: 27
<212> TYPE: DNA
<213> ORGANISM: Artificial Sequence
<220> FEATURE:
<223> OTHER INFORMATION: forward primer for 4CL-N

<400> SEQUENCE: 19
atgggttccg tggacacggc ggtcgcg                                     27

<210> SEQ ID NO 20
<211> LENGTH: 26
<212> TYPE: DNA
<213> ORGANISM: Artificial Sequence
<220> FEATURE:
<223> OTHER INFORMATION: reverse primer for 4CL-N

<400> SEQUENCE: 20
tcagtgaaca ccggcggcga gcctgg                                      26

<210> SEQ ID NO 21
<211> LENGTH: 20
<212> TYPE: DNA
<213> ORGANISM: Artificial Sequence
<220> FEATURE:
<223> OTHER INFORMATION: forward primer for 4CL-M and 4CL-L RNAi
      constructs

<400> SEQUENCE: 21
```

-continued

```
catcaagggt acgggatgac                                              20
```

<210> SEQ ID NO 22
<211> LENGTH: 26
<212> TYPE: DNA
<213> ORGANISM: Artificial Sequence
<220> FEATURE:
<223> OTHER INFORMATION: reverse primer for 4CL-M and 4CL-L RNAi
       constructs

<400> SEQUENCE: 22

```
gtagcctgct agtcttctct ctcatt                                       26
```

<210> SEQ ID NO 23
<211> LENGTH: 555
<212> TYPE: PRT
<213> ORGANISM: Sorghum bicolor

<400> SEQUENCE: 23

```
Met Gly Ser Val Asp Thr Ala Val Ala Val Pro Val Pro Val Pro Glu
1               5                   10                  15

Pro Glu Ala Glu Glu Lys Ala Ala Val Val Phe Arg Ser Lys Leu Pro
                20                  25                  30

Asp Ile Glu Ile Asn Asn Ser Gln Ser Leu Gln Thr Tyr Cys Phe Gly
            35                  40                  45

Lys Met Ser Glu Val Ala Asp Arg Ala Cys Leu Ile Asp Gly Gln Thr
        50                  55                  60

Gly Ala Ser Tyr Thr Tyr Ala Glu Val Glu Ser Leu Ser Arg Arg Ala
65                  70                  75                  80

Ala Ser Gly Leu Arg Ala Met Gly Val Gly Lys Gly Asp Val Val Met
                85                  90                  95

Asn Leu Leu Arg Asn Cys Pro Glu Phe Ala Phe Thr Phe Leu Gly Ala
            100                 105                 110

Ala Arg Leu Gly Ala Ala Thr Thr Thr Ala Asn Pro Phe Tyr Thr Pro
        115                 120                 125

His Glu Ile His Arg Gln Ala Glu Ala Ala Gly Ala Lys Val Ile Val
    130                 135                 140

Thr Glu Ala Cys Ala Val Glu Lys Val Arg Glu Phe Ala Ala Gly Arg
145                 150                 155                 160

Gly Val Pro Val Val Thr Val Asp Gly Arg Phe Asp Gly Cys Val Glu
                165                 170                 175

Phe Ala Glu Val Ile Ala Ala Glu Leu Asp Ala Asp Ala Asp Val
            180                 185                 190

His Pro Asp Asp Val Val Ala Leu Pro Tyr Ser Ser Gly Thr Thr Gly
        195                 200                 205

Leu Pro Lys Gly Val Met Leu Thr His Arg Ser Leu Ile Thr Ser Val
    210                 215                 220

Ala Gln Gln Val Asp Gly Glu Asn Pro Asn Leu Tyr Phe Ser Lys Asp
225                 230                 235                 240

Asp Val Val Leu Cys Leu Leu Pro Leu Phe His Ile Tyr Ser Leu Asn
                245                 250                 255

Ser Val Leu Leu Ala Gly Leu Arg Ala Gly Ser Thr Ile Val Ile Met
            260                 265                 270

Arg Lys Phe Asp Leu Gly Ala Leu Val Asp Leu Val Arg Lys His Gly
        275                 280                 285

Ile Thr Ile Ala Pro Phe Val Pro Pro Ile Val Val Glu Ile Ala Lys
    290                 295                 300
```

Ser Pro Arg Val Thr Ala Asp Asp Leu Ala Ser Ile Arg Met Val Met
305                 310                 315                 320

Ser Gly Ala Ala Pro Met Gly Lys Glu Leu Gln Asp Ala Phe Met Thr
                325                 330                 335

Lys Ile Pro Asn Ala Val Leu Gly Gln Gly Tyr Gly Met Thr Glu Ala
            340                 345                 350

Gly Pro Val Leu Ala Met Cys Leu Ala Phe Ala Lys Glu Pro Phe Gln
        355                 360                 365

Val Lys Ser Gly Ser Cys Gly Thr Val Val Arg Asn Ala Glu Leu Lys
    370                 375                 380

Val Val Asp Pro Asp Thr Gly Ala Ala Leu Gly Arg Asn Gln Pro Gly
385                 390                 395                 400

Glu Ile Cys Ile Arg Gly Glu Gln Ile Met Lys Gly Tyr Leu Asn Asp
                405                 410                 415

Leu Glu Ser Thr Lys Asn Thr Ile Asp Lys Asp Gly Trp Leu His Thr
            420                 425                 430

Gly Asp Ile Gly Tyr Val Asp Asp Asp Glu Ile Phe Ile Val Asp
        435                 440                 445

Arg Leu Lys Glu Ile Ile Lys Tyr Lys Gly Phe Gln Val Pro Pro Ala
    450                 455                 460

Glu Leu Glu Ala Leu Leu Ile Thr His Pro Glu Ile Lys Asp Ala Ala
465                 470                 475                 480

Val Val Ser Met Lys Asp Asp Leu Ala Gly Glu Ile Pro Val Ala Phe
                485                 490                 495

Ile Val Arg Thr Glu Gly Ser Glu Val Thr Glu Asp Glu Ile Lys Gln
            500                 505                 510

Phe Val Ala Lys Glu Val Phe Tyr Lys Lys Ile His Lys Val Phe
        515                 520                 525

Phe Thr Glu Ser Ile Pro Lys Asn Pro Ser Gly Lys Ile Leu Arg Lys
    530                 535                 540

Asp Leu Arg Ala Arg Leu Ala Ala Gly Val His
545                 550                 555

<210> SEQ ID NO 24
<211> LENGTH: 557
<212> TYPE: PRT
<213> ORGANISM: Sorghum bicolor

<400> SEQUENCE: 24

Met Gly Ser Val Ala Glu Asp Ser Ala Ala Pro Ala Ala Ser Val
1               5                   10                  15

Val Phe Arg Ser Lys Leu Pro Asp Ile Glu Ile Pro Arg His Leu Ser
            20                  25                  30

Leu Gln Ala Tyr Cys Phe Glu Arg Leu Pro Glu Val Ser Ser Arg Pro
        35                  40                  45

Cys Leu Ile Asp Gly Gln Thr Gly Ala Val His Thr Tyr Ala Asp Val
    50                  55                  60

Glu Arg Leu Ser Arg Thr Ala Ala Ala Leu Arg Gly Leu Gly Val
65                  70                  75                  80

Gly Lys Gly Asp Val Val Met Asn Leu Leu Arg Asn Cys Pro Glu Phe
                85                  90                  95

Ala Phe Val Phe Leu Gly Ala Ala Arg Leu Gly Ala Ala Thr Thr Thr
            100                 105                 110

Ala Asn Pro Phe Tyr Thr Pro His Glu Ile His Arg Gln Ala Ala Ala

```
            115                 120                 125
Ala Gly Ala Lys Val Ile Val Thr Glu Ala Cys Ala Val Glu Lys Val
130                 135                 140

Arg Gly Phe Ala Ala Glu Arg Gly Val Pro Val Ala Thr Val Asp Gly
145                 150                 155                 160

Gly Ala Phe Asp Gly Cys Leu Glu Leu Gly Ala Leu Met Asp Ala Ala
                165                 170                 175

Glu Pro Leu Ala Asp Asp Glu Glu Val Asp Pro Asp Asp Val Val Ala
                180                 185                 190

Leu Pro Tyr Ser Ser Gly Thr Thr Gly Met Pro Lys Gly Val Met Leu
                195                 200                 205

Thr His Arg Ser Leu Val Thr Ser Val Ala Gln Gln Val Asp Gly Glu
210                 215                 220

Asn Pro Asn Leu His Phe Ser Ser Asp Val Val Leu Cys Val Leu
225                 230                 235                 240

Pro Leu Phe His Ile Tyr Ser Leu Asn Ser Val Leu Leu Ala Gly Leu
                245                 250                 255

Arg Ala Gly Cys Ala Ile Val Ile Met Arg Lys Phe Glu Ile Gly Ala
                260                 265                 270

Leu Val Glu Leu Val Arg Ala His Gly Val Thr Val Ala Pro Phe Val
                275                 280                 285

Pro Pro Ile Val Val Glu Ile Ala Lys Ser Pro Arg Val Gly Ala Ala
290                 295                 300

Asp Leu Ala Ser Ile Arg Met Val Met Ser Gly Ala Ala Pro Met Gly
305                 310                 315                 320

Lys Asp Leu Gln Asp Ala Phe Met Ala Lys Ile Pro Asn Ala Val Leu
                325                 330                 335

Gly Gln Gly Tyr Gly Met Thr Glu Ala Gly Pro Val Leu Ala Met Cys
                340                 345                 350

Leu Ala Phe Ala Lys Glu Pro Phe Glu Val Lys Ser Gly Ser Cys Gly
                355                 360                 365

Thr Val Val Arg Asn Ala Glu Leu Lys Ile Val Asp Pro Asp Thr Ser
370                 375                 380

Glu Ser Leu Gly Arg Asn Gln Pro Gly Glu Ile Cys Ile Arg Gly Glu
385                 390                 395                 400

Gln Ile Met Lys Gly Tyr Leu Asn Asp Pro Glu Ala Thr Lys Asn Thr
                405                 410                 415

Ile Asp Lys Asp Gly Trp Leu His Thr Gly Asp Ile Gly Tyr Val Asp
                420                 425                 430

Asp Asp Asp Glu Ile Phe Ile Val Asp Arg Leu Lys Glu Ile Ile Lys
                435                 440                 445

Tyr Lys Gly Phe Gln Val Pro Ala Glu Leu Glu Ala Leu Leu Ile
                450                 455                 460

Thr His Pro Glu Ile Lys Asp Ala Ala Val Val Ser Met Lys Asp Glu
465                 470                 475                 480

Leu Ala Gly Glu Val Pro Val Ala Phe Ile Ile Arg Ser Glu Gly Ser
                485                 490                 495

Glu Ile Ser Glu Asn Glu Ile Lys Gln Phe Val Ala Lys Glu Val Val
                500                 505                 510

Phe Tyr Lys Arg Ile Asn Arg Val Phe Phe Thr Asp Ser Ile Pro Lys
                515                 520                 525

Asn Pro Ser Gly Lys Ile Leu Arg Lys Asp Leu Arg Ala Arg Leu Ala
530                 535                 540
```

Ala Gly Ile Pro Ser Ser Asp Asn Thr Gln Ser Lys Ser
545                 550                 555

<210> SEQ ID NO 25
<211> LENGTH: 566
<212> TYPE: PRT
<213> ORGANISM: Sorghum bicolor

<400> SEQUENCE: 25

Met Ile Thr Val Ala Ala Pro Glu Ala Gln Pro Gln Val Ala Ala Pro
1               5                   10                  15

Ala Ala Pro Glu Glu Thr Val Phe Arg Ser Lys Leu Pro Asp Ile Asp
            20                  25                  30

Ile Ala Ser His Leu Pro Leu His Glu Tyr Cys Phe Ala Arg Ala Ala
        35                  40                  45

Glu Val Ala Asp Ala Pro Cys Leu Ile Ala Ala Thr Gly Arg Thr
    50                  55                  60

Tyr Thr Tyr Ala Glu Thr Arg Leu Leu Cys Arg Lys Ala Ala Ser
65                  70                  75                  80

Leu His Gly Leu Gly Val Gly His Gly Asp Arg Val Met Ile Leu Leu
                85                  90                  95

Gln Asn Ser Val Glu Phe Val Leu Thr Phe Leu Gly Ala Ser Phe Leu
            100                 105                 110

Gly Ala Val Thr Thr Ala Ala Asn Pro Phe Cys Thr Pro Leu Glu Ile
            115                 120                 125

His Lys Gln Phe Arg Ala Ser Gly Ala Lys Leu Ile Val Thr Gln Ser
130                 135                 140

Ala Tyr Val Asp Lys Leu Arg His Glu Ala Phe Pro Arg Ile Gly Gly
145                 150                 155                 160

Glu Asp Lys Asp Asn Ala Leu Thr Val Leu Thr Ile Asp Asp Val Ala
                165                 170                 175

Asp Thr Pro Glu Gly Cys Leu Ala Phe Trp Glu Leu Val Thr Pro Ala
            180                 185                 190

Asp Asp Ala Ala Leu Pro Glu Val Ser Ile Ser Pro Asp Asp Pro Val
        195                 200                 205

Ala Leu Pro Phe Ser Ser Gly Thr Thr Gly Leu Pro Lys Gly Val Val
210                 215                 220

Leu Thr His Gly Gly Gln Val Ser Asn Val Ala Gln Gln Val Asp Gly
225                 230                 235                 240

Ala Asn Pro Asn Leu Tyr Met Arg Glu Gly Asp Val Ala Leu Cys Val
                245                 250                 255

Leu Pro Leu Phe His Ile Phe Ser Leu Asn Ser Val Leu Leu Cys Ala
            260                 265                 270

Leu Arg Ala Gly Ala Ala Val Met Leu Met Pro Lys Phe Glu Met Gly
        275                 280                 285

Ala Met Leu Glu Gly Ile Gln Arg Trp Arg Val Thr Val Ala Ala Val
    290                 295                 300

Val Pro Pro Leu Val Leu Ala Leu Ala Lys Asn Pro Ala Leu Glu Lys
305                 310                 315                 320

Tyr Asp Leu Ser Ser Ile Arg Ile Val Leu Ser Gly Ala Ala Pro Leu
                325                 330                 335

Gly Lys Glu Leu Val Asp Ala Leu Arg Ala Arg Val Pro Gln Ala Val
            340                 345                 350

Phe Gly Gln Gly Tyr Gly Met Thr Glu Ala Gly Pro Val Leu Ser Met

```
            355                 360                 365
Cys Pro Ala Phe Ala Lys Glu Pro Thr Pro Ala Lys Pro Gly Ser Cys
            370                 375                 380

Gly Thr Val Val Arg Asn Ala Glu Leu Lys Val Val Asp Pro Asp Thr
385                 390                 395                 400

Gly Leu Ser Leu Gly Arg Asn Leu Pro Gly Glu Ile Cys Ile Arg Gly
                405                 410                 415

Pro Gln Ile Met Lys Gly Tyr Leu Asn Asp Pro Glu Ala Thr Ala Arg
            420                 425                 430

Thr Ile Asp Val Asp Gly Trp Leu His Thr Gly Asp Ile Gly Tyr Val
            435                 440                 445

Asp Asp Asp Glu Val Phe Ile Val Asp Arg Val Lys Glu Leu Ile
            450                 455                 460

Lys Phe Lys Gly Phe Gln Val Pro Pro Ala Leu Glu Ala Leu Leu
465                 470                 475                 480

Ile Ala His Pro Ser Ile Ala Asp Ala Ala Val Val Pro Gln Lys Asp
                485                 490                 495

Asp Ala Ala Gly Glu Val Pro Val Ala Phe Val Val Arg Ala Ala Asp
            500                 505                 510

Ser Asp Ile Ala Glu Asp Ala Ile Lys Glu Phe Ile Ser Lys Gln Val
            515                 520                 525

Val Phe Tyr Lys Arg Leu His Lys Val Tyr Phe Thr Pro Ser Ile Pro
            530                 535                 540

Lys Ser Ala Ser Gly Lys Ile Leu Arg Arg Glu Leu Arg Ala Lys Leu
545                 550                 555                 560

Ala Ala Ala Ala Ser Thr
                565

<210> SEQ ID NO 26
<211> LENGTH: 555
<212> TYPE: PRT
<213> ORGANISM: Zea mays

<400> SEQUENCE: 26

Met Gly Ser Val Asp Ala Ala Ile Ala Val Pro Val Pro Ala Ala Glu
1               5                   10                  15

Glu Lys Ala Val Glu Glu Lys Ala Met Val Phe Arg Ser Lys Leu Pro
            20                  25                  30

Asp Ile Glu Ile Asp Ser Ser Met Ala Leu His Thr Tyr Cys Phe Gly
            35                  40                  45

Lys Met Gly Glu Val Ala Glu Arg Ala Cys Leu Ile Asp Gly Leu Thr
50                  55                  60

Gly Ala Ser Tyr Thr Tyr Ala Glu Val Glu Ser Leu Ser Arg Arg Ala
65                  70                  75                  80

Ala Ser Gly Leu Arg Ala Met Gly Val Gly Lys Gly Asp Val Val Met
                85                  90                  95

Ser Leu Leu Arg Asn Cys Pro Glu Phe Ala Phe Thr Phe Leu Gly Ala
            100                 105                 110

Ala Arg Leu Gly Ala Ala Thr Thr Thr Ala Asn Pro Phe Tyr Thr Pro
            115                 120                 125

His Glu Val His Arg Gln Ala Glu Ala Ala Gly Ala Arg Leu Ile Val
            130                 135                 140

Thr Glu Ala Cys Ala Val Glu Lys Val Arg Glu Phe Ala Ala Glu Arg
145                 150                 155                 160
```

```
Gly Ile Pro Val Val Thr Val Asp Gly Arg Phe Asp Gly Cys Val Glu
            165                 170                 175

Phe Ala Glu Leu Ile Ala Ala Glu Glu Leu Glu Ala Asp Ala Asp Ile
        180                 185                 190

His Pro Asp Asp Val Val Ala Leu Pro Tyr Ser Ser Gly Thr Thr Gly
        195                 200                 205

Leu Pro Lys Gly Val Met Leu Thr His Arg Ser Leu Ile Thr Ser Val
    210                 215                 220

Ala Gln Gln Val Asp Gly Glu Asn Pro Asn Leu Tyr Phe Arg Lys Asp
225                 230                 235                 240

Asp Val Val Leu Cys Leu Leu Pro Leu Phe His Ile Tyr Ser Leu Asn
                245                 250                 255

Ser Val Leu Leu Ala Gly Leu Arg Ala Gly Ser Thr Ile Val Ile Met
            260                 265                 270

Arg Lys Phe Asp Leu Gly Ala Leu Val Asp Leu Val Arg Arg Tyr Val
        275                 280                 285

Ile Thr Ile Ala Pro Phe Val Pro Pro Ile Val Val Glu Ile Ala Lys
    290                 295                 300

Ser Pro Arg Val Thr Ala Gly Asp Leu Ala Ser Ile Arg Met Val Met
305                 310                 315                 320

Ser Gly Ala Ala Pro Met Gly Lys Glu Leu Gln Asp Ala Phe Met Ala
                325                 330                 335

Lys Ile Pro Asn Ala Val Leu Gly Gln Gly Tyr Gly Met Thr Glu Ala
            340                 345                 350

Gly Pro Val Leu Ala Met Cys Leu Ala Phe Ala Lys Glu Pro Tyr Pro
        355                 360                 365

Val Lys Ser Gly Ser Cys Gly Thr Val Val Arg Asn Ala Glu Leu Lys
    370                 375                 380

Ile Val Asp Pro Asp Thr Gly Ala Ala Leu Gly Arg Asn Gln Pro Gly
385                 390                 395                 400

Glu Ile Cys Ile Arg Gly Glu Gln Ile Met Lys Gly Tyr Leu Asn Asp
                405                 410                 415

Pro Glu Ser Thr Lys Asn Thr Ile Asp Gln Asp Gly Trp Leu His Thr
            420                 425                 430

Gly Asp Ile Gly Tyr Val Asp Asp Asp Glu Ile Phe Ile Val Asp
        435                 440                 445

Arg Leu Lys Glu Ile Ile Lys Tyr Lys Gly Phe Gln Val Pro Pro Ala
    450                 455                 460

Glu Leu Glu Ala Leu Leu Ile Thr His Pro Glu Ile Lys Asp Ala Ala
465                 470                 475                 480

Val Val Ser Met Asn Asp Asp Leu Ala Gly Glu Ile Pro Val Ala Phe
                485                 490                 495

Ile Val Arg Thr Glu Gly Ser Gln Val Thr Glu Asp Glu Ile Lys Gln
            500                 505                 510

Phe Val Ala Lys Glu Val Val Phe Tyr Lys Lys Ile His Lys Val Phe
        515                 520                 525

Phe Thr Glu Ser Ile Pro Lys Asn Pro Ser Gly Lys Ile Leu Arg Lys
    530                 535                 540

Asp Leu Arg Ala Arg Leu Ala Ala Gly Val His
545                 550                 555

<210> SEQ ID NO 27
<211> LENGTH: 557
<212> TYPE: PRT
```

<213> ORGANISM: Lolium perenne

<400> SEQUENCE: 27

| | | | | | | | | | | | | | | |
|---|---|---|---|---|---|---|---|---|---|---|---|---|---|---|
| Met | Gly | Ser | Val | Pro | Glu | Glu | Ser | Val | Val | Ala | Val | Ala | Pro | Ala | Glu |
| 1 | | | | 5 | | | | | 10 | | | | | 15 | |
| Thr | Val | Phe | Arg | Ser | Lys | Leu | Pro | Asp | Ile | Glu | Ile | Asn | Asn | Glu | Gln |
| | | | 20 | | | | | 25 | | | | | 30 | | |
| Thr | Leu | Gln | Ser | Tyr | Cys | Phe | Glu | Lys | Met | Ala | Glu | Val | Ala | Ser | Arg |
| | | 35 | | | | | 40 | | | | | 45 | | | |
| Pro | Cys | Ile | Ile | Asp | Gly | Gln | Thr | Gly | Ala | Ser | Tyr | Thr | Tyr | Thr | Glu |
| | 50 | | | | | 55 | | | | | 60 | | | | |
| Val | Asp | Ser | Leu | Thr | Arg | Arg | Ala | Ala | Ala | Gly | Leu | Arg | Arg | Met | Gly |
| 65 | | | | | 70 | | | | | 75 | | | | | 80 |
| Val | Gly | Lys | Gly | Asp | Val | Val | Met | Asn | Leu | Leu | Arg | Asn | Cys | Pro | Glu |
| | | | | 85 | | | | | 90 | | | | | 95 | |
| Phe | Ala | Phe | Ser | Phe | Leu | Gly | Ala | Ala | Arg | Leu | Gly | Ala | Ala | Thr | Thr |
| | | | 100 | | | | | 105 | | | | | 110 | | |
| Thr | Ala | Asn | Pro | Phe | Tyr | Thr | Pro | His | Glu | Ile | His | Arg | Gln | Ala | Glu |
| | | 115 | | | | | 120 | | | | | 125 | | | |
| Ala | Ala | Gly | Ala | Lys | Leu | Ile | Val | Thr | Glu | Ala | Cys | Ala | Val | Glu | Lys |
| | 130 | | | | | 135 | | | | | 140 | | | | |
| Val | Leu | Glu | Phe | Ala | Ala | Gly | Arg | Gly | Val | Pro | Val | Val | Thr | Val | Asp |
| 145 | | | | | 150 | | | | | 155 | | | | | 160 |
| Gly | Arg | Arg | Asp | Gly | Cys | Val | Asp | Phe | Ala | Glu | Leu | Ile | Ala | Gly | Glu |
| | | | | 165 | | | | | 170 | | | | | 175 | |
| Glu | Leu | Pro | Glu | Ala | Asp | Glu | Ala | Gly | Val | Leu | Pro | Asp | Asp | Val | Val |
| | | | 180 | | | | | 185 | | | | | 190 | | |
| Ala | Leu | Pro | Tyr | Ser | Ser | Gly | Thr | Thr | Gly | Leu | Pro | Lys | Gly | Val | Met |
| | | 195 | | | | | 200 | | | | | 205 | | | |
| Leu | Thr | His | Arg | Ser | Leu | Val | Thr | Ser | Val | Ala | Gln | Leu | Val | Asp | Gly |
| | 210 | | | | | 215 | | | | | 220 | | | | |
| Ser | Asn | Pro | Asn | Val | Cys | Phe | Asn | Lys | Asp | Asp | Ala | Leu | Leu | Cys | Leu |
| 225 | | | | | 230 | | | | | 235 | | | | | 240 |
| Leu | Pro | Leu | Phe | His | Ile | Tyr | Ser | Leu | His | Thr | Val | Leu | Leu | Ala | Gly |
| | | | | 245 | | | | | 250 | | | | | 255 | |
| Leu | Arg | Val | Gly | Ala | Ala | Ile | Val | Ile | Met | Arg | Lys | Phe | Asp | Val | Gly |
| | | | 260 | | | | | 265 | | | | | 270 | | |
| Ala | Leu | Val | Asp | Leu | Val | Arg | Ala | His | Arg | Ile | Thr | Ile | Ala | Pro | Phe |
| | | 275 | | | | | 280 | | | | | 285 | | | |
| Val | Pro | Pro | Ile | Val | Val | Glu | Ile | Ala | Lys | Ser | Asp | Arg | Val | Gly | Ala |
| | 290 | | | | | 295 | | | | | 300 | | | | |
| Asp | Asp | Leu | Ala | Ser | Ile | Arg | Met | Val | Leu | Ser | Gly | Ala | Ala | Pro | Met |
| 305 | | | | | 310 | | | | | 315 | | | | | 320 |
| Gly | Lys | Asp | Leu | Gln | Asp | Ala | Phe | Met | Ala | Lys | Ile | Pro | Asn | Ala | Val |
| | | | | 325 | | | | | 330 | | | | | 335 | |
| Leu | Gly | Gln | Gly | Tyr | Gly | Met | Thr | Glu | Ala | Gly | Pro | Val | Leu | Ala | Met |
| | | | 340 | | | | | 345 | | | | | 350 | | |
| Cys | Leu | Ala | Phe | Ala | Lys | Glu | Pro | Phe | Lys | Val | Lys | Ser | Gly | Ser | Cys |
| | | 355 | | | | | 360 | | | | | 365 | | | |
| Gly | Thr | Val | Val | Arg | Asn | Ala | Glu | Leu | Lys | Val | Val | Asp | Pro | Asp | Thr |
| | 370 | | | | | 375 | | | | | 380 | | | | |
| Gly | Ala | Ser | Leu | Gly | Arg | Asn | Gln | Pro | Gly | Glu | Ile | Cys | Val | Arg | Gly |
| 385 | | | | | 390 | | | | | 395 | | | | | 400 |

```
Lys Gln Ile Met Ile Gly Tyr Leu Asn Asp Pro Glu Ser Thr Lys Asn
                405                 410                 415

Thr Ile Asp Lys Asp Gly Trp Leu His Thr Gly Asp Ile Gly Leu Val
            420                 425                 430

Asp Asp Asp Asp Glu Ile Phe Ile Val Asp Arg Leu Lys Glu Ile Ile
        435                 440                 445

Lys Tyr Lys Gly Phe Gln Val Ala Pro Ala Glu Leu Glu Ala Leu Leu
    450                 455                 460

Leu Thr Asn Pro Glu Val Lys Asp Ala Ala Val Val Gly Val Lys Asp
465                 470                 475                 480

Asp Leu Cys Gly Glu Val Pro Val Ala Phe Ile Lys Arg Ile Glu Gly
                485                 490                 495

Ser Glu Ile Asn Glu Asn Glu Ile Lys Gln Phe Val Ser Lys Glu Val
                500                 505                 510

Val Phe Tyr Lys Arg Ile Asn Lys Val Tyr Phe Thr Asp Ser Ile Pro
            515                 520                 525

Lys Asn Pro Ser Gly Lys Ile Leu Arg Lys Asp Leu Arg Ala Arg Leu
    530                 535                 540

Ala Ala Gly Ile Pro Thr Glu Val Ala Ala Pro Arg Ser
545                 550                 555

<210> SEQ ID NO 28
<211> LENGTH: 556
<212> TYPE: PRT
<213> ORGANISM: Lolium perenne

<400> SEQUENCE: 28

Met Gly Ser Ile Ala Ala Asp Ala Pro Pro Ala Glu Leu Val Phe Arg
1               5                   10                  15

Ser Lys Leu Pro Asp Ile Glu Ile Pro Thr His Leu Thr Leu Gln Asp
                20                  25                  30

Tyr Cys Phe Gln Arg Leu Pro Glu Leu Ser Ala Arg Ala Cys Leu Ile
            35                  40                  45

Asp Gly Ala Thr Gly Ala Ala Leu Thr Tyr Gly Glu Val Asp Ala Leu
    50                  55                  60

Ser Arg Arg Cys Ala Ala Gly Leu Arg Arg Leu Gly Val Gly Lys Gly
65                  70                  75                  80

Asp Val Val Met Ala Leu Leu Arg Asn Cys Pro Glu Phe Ala Phe Val
                85                  90                  95

Phe Leu Gly Ala Ala Arg Leu Gly Ala Ala Thr Thr Thr Ala Asn Pro
            100                 105                 110

Phe Tyr Thr Pro His Glu Ile His Arg Gln Ala Thr Ala Ala Gly Ala
        115                 120                 125

Arg Val Ile Val Thr Glu Ala Cys Ala Val Glu Lys Val Arg Ala Phe
    130                 135                 140

Ala Ala Glu Arg Gly Ile Pro Val Val Ser Val Asp Glu Gly Val Asp
145                 150                 155                 160

Gly Gly Cys Leu Pro Phe Ala Glu Thr Leu Leu Gly Glu Glu Ser Gly
                165                 170                 175

Glu Arg Phe Val Asp Glu Ala Val Asp Pro Asp Asp Val Ala Leu
            180                 185                 190

Pro Tyr Ser Ser Gly Thr Thr Gly Leu Pro Lys Gly Val Met Leu Thr
        195                 200                 205

His Arg Ser Leu Val Thr Ser Val Ala Gln Gln Val Asp Gly Glu Asn
    210                 215                 220
```

Pro Asn Leu His Phe Ser Ser Asp Val Leu Cys Val Leu Pro
225                 230                 235                 240

Leu Phe His Ile Tyr Ser Leu Asn Ser Val Leu Ala Gly Leu Arg
            245                 250                 255

Ala Gly Cys Ala Ile Val Ile Met Arg Lys Phe Asp His Gly Ala Leu
            260                 265                 270

Val Asp Leu Val Arg Thr His Gly Val Thr Val Ala Pro Phe Val Pro
            275                 280                 285

Pro Ile Val Val Glu Ile Ala Lys Ser Ala Arg Val Thr Ala Ala Asp
290                 295                 300

Leu Ala Ser Ile Arg Leu Val Met Ser Gly Ala Ala Pro Met Gly Lys
305                 310                 315                 320

Glu Leu Gln Asp Ala Phe Met Ala Lys Ile Pro Asn Ala Val Leu Gly
                325                 330                 335

Gln Gly Tyr Gly Met Thr Glu Ala Gly Pro Val Leu Ala Met Cys Leu
                340                 345                 350

Ala Phe Ala Lys Glu Pro Phe Ala Val Lys Ser Gly Ser Cys Gly Thr
                355                 360                 365

Val Val Arg Asn Ala Glu Leu Lys Ile Val Asp Pro Asp Thr Gly Ala
            370                 375                 380

Ser Leu Gly Arg Asn Leu Pro Gly Glu Ile Cys Ile Arg Gly Lys Gln
385                 390                 395                 400

Ile Met Lys Gly Tyr Leu Asn Asp Pro Val Ala Thr Lys Asn Thr Ile
                405                 410                 415

Asp Lys Asp Gly Trp Leu His Thr Gly Asp Ile Gly Tyr Val Asp Asp
                420                 425                 430

Asp Asp Glu Ile Phe Ile Val Asp Arg Leu Lys Glu Ile Ile Lys Tyr
                435                 440                 445

Lys Gly Phe Gln Val Pro Pro Ala Glu Leu Glu Ala Leu Leu Ile Thr
                450                 455                 460

His Pro Glu Ile Lys Asp Ala Ala Val Val Ser Met Gln Asp Glu Leu
465                 470                 475                 480

Ala Gly Glu Val Pro Val Ala Phe Val Val Arg Thr Glu Gly Ser Glu
                485                 490                 495

Ile Ser Glu Asn Glu Ile Lys Gln Phe Val Ala Lys Glu Val Val Phe
                500                 505                 510

Tyr Lys Arg Ile Cys Lys Val Phe Phe Ala Asp Ser Ile Pro Lys Ser
                515                 520                 525

Pro Ser Gly Lys Ile Leu Arg Lys Asp Leu Arg Ala Lys Leu Ala Ala
                530                 535                 540

Gly Ile Pro Ser Ser Asn Thr Thr Gln Ser Lys Ser
545                 550                 555

<210> SEQ ID NO 29
<211> LENGTH: 570
<212> TYPE: PRT
<213> ORGANISM: Lolium perenne

<400> SEQUENCE: 29

Met Ile Thr Val Ala Ala Pro Glu Val Gln Gln Pro Gln Ile Ala Ala
1               5                   10                  15

Ala Ala Ala Val Glu Ala Ala Pro Glu Ala Thr Thr Ile Phe
                20                  25                  30

Arg Ser Arg Leu Pro Asp Ile Asp Ile Pro Thr His Met Pro Leu His

```
                35                  40                  45
Asp Tyr Cys Phe Ala Thr Ala Ser Ala Pro Asp Ala Pro Cys Leu
 50                  55                  60

Ile Thr Ala Ala Thr Gly Lys Thr Tyr Thr Phe Ala Glu Thr His Leu
 65                  70                  75                  80

Leu Cys Arg Lys Ala Ala Ala Leu His Gly Leu Gly Val Arg His
                 85                  90                  95

Gly Asp Arg Ile Met Leu Leu Gln Asn Ser Val Glu Phe Ala Leu
                100                 105                 110

Ala Phe Phe Gly Ala Ser Met Leu Gly Ala Val Ser Thr Ala Ala Asn
                115                 120                 125

Pro Phe Cys Thr Pro Gln Glu Ile His Lys Gln Leu Val Ala Ser Gly
                130                 135                 140

Ala Lys Leu Val Val Thr Gln Ser Ala Tyr Val Asp Lys Leu Arg His
145                 150                 155                 160

Glu Ala Phe Pro Arg Ile Gly Glu Ala Leu Thr Val Ile Thr Ile Asp
                165                 170                 175

Glu Asp Asp Gly Thr Pro Asp Gly Cys Gln Pro Phe Trp Ala Leu Val
                180                 185                 190

Ser Ala Ala Asp Glu Asn Ser Val Pro Glu Ser Pro Ile Ser Pro Asp
                195                 200                 205

Asp Ala Val Ala Leu Pro Tyr Ser Ser Gly Thr Thr Gly Leu Pro Lys
                210                 215                 220

Gly Val Val Leu Thr His Gly Gly Leu Val Ser Ser Val Ala Gln Gln
225                 230                 235                 240

Val Asp Gly Glu Asn Pro Asn Leu His Met Arg Ala Gly Glu Asp Val
                245                 250                 255

Val Leu Cys Val Leu Pro Leu Phe His Ile Phe Ser Leu Asn Ser Val
                260                 265                 270

Leu Leu Cys Ala Leu Arg Ala Gly Ala Ala Val Met Leu Met Pro Arg
                275                 280                 285

Phe Glu Met Gly Ala Met Leu Glu Gly Ile Glu Arg Trp Arg Val Thr
290                 295                 300

Val Ala Ala Val Val Pro Pro Leu Val Leu Ala Leu Ala Lys Asn Pro
305                 310                 315                 320

Gly Val Glu Lys His Asp Leu Ser Ser Ile Arg Ile Val Leu Ser Gly
                325                 330                 335

Ala Ala Pro Leu Gly Lys Glu Leu Glu Asp Ala Leu Arg Gly Arg Leu
                340                 345                 350

Pro Gln Ala Ile Phe Gly Gln Gly Tyr Gly Met Thr Glu Ala Gly Pro
                355                 360                 365

Val Leu Ser Met Cys Pro Ala Phe Ala Arg Glu Pro Thr Pro Ala Lys
                370                 375                 380

Ser Gly Ser Cys Gly Thr Val Val Arg Asn Ala Gln Leu Lys Val Val
385                 390                 395                 400

Asp Pro Asp Thr Gly Val Ser Leu Gly Arg Asn Leu Pro Gly Glu Ile
                405                 410                 415

Cys Ile Arg Gly Pro Gln Ile Met Lys Gly Tyr Leu Asn Asp Pro Val
                420                 425                 430

Ala Thr Ala Ala Thr Ile Asp Val Glu Gly Trp Leu His Thr Gly Asp
                435                 440                 445

Ile Gly Tyr Val Asp Asp Asp Glu Val Phe Ile Val Asp Arg Val
                450                 455                 460
```

Lys Glu Leu Ile Lys Phe Lys Gly Phe Gln Val Pro Ala Glu Leu
465                 470                 475                 480

Glu Ala Leu Leu Ile Ala His Pro Ser Ile Ala Asp Ala Ala Val Val
            485                 490                 495

Pro Gln Lys Asp Asp Ala Ala Gly Glu Val Pro Val Ala Phe Val Val
            500                 505                 510

Arg Ala Ala Asp Ser Asp Ile Ala Glu Glu Ala Ile Lys Glu Phe Val
            515                 520                 525

Ser Lys Gln Val Val Phe Tyr Lys Arg Leu His Lys Val Tyr Phe Thr
530                 535                 540

His Ala Ile Pro Lys Ser Ala Ser Gly Lys Ile Leu Arg Lys Glu Leu
545                 550                 555                 560

Arg Ala Lys Leu Ala Ala Pro Ala Thr Ala
                565                 570

<210> SEQ ID NO 30
<211> LENGTH: 554
<212> TYPE: PRT
<213> ORGANISM: Oryza sativa

<400> SEQUENCE: 30

Met Gly Ser Val Ala Ala Glu Glu Val Val Phe Arg Ser Lys Leu
1               5                   10                  15

Pro Asp Ile Glu Ile Asp Asn Ser Met Thr Leu Gln Glu Tyr Cys Phe
            20                  25                  30

Ala Arg Met Ala Glu Val Gly Ala Arg Pro Cys Leu Ile Asp Gly Gln
            35                  40                  45

Thr Gly Glu Ser Tyr Thr Tyr Ala Glu Val Glu Ser Ala Ser Arg Arg
50                  55                  60

Ala Ala Ala Gly Leu Arg Arg Met Gly Val Gly Lys Gly Asp Val Val
65              70                  75                  80

Met Ser Leu Leu Arg Asn Cys Pro Glu Phe Ala Phe Ser Phe Leu Gly
                85                  90                  95

Ala Ala Arg Leu Gly Ala Ala Thr Thr Thr Ala Asn Pro Phe Tyr Thr
            100                 105                 110

Pro His Glu Val His Arg Gln Ala Glu Ala Gly Ala Arg Val Ile
            115                 120                 125

Val Thr Glu Ala Cys Ala Val Glu Lys Val Arg Glu Phe Ala Ala Glu
130                 135                 140

Arg Gly Val Pro Val Val Thr Val Asp Gly Ala Phe Asp Gly Cys Val
145                 150                 155                 160

Glu Phe Arg Glu Val Leu Ala Ala Glu Glu Leu Asp Ala Asp Ala Asp
            165                 170                 175

Val His Pro Asp Asp Val Val Ala Leu Pro Tyr Ser Ser Gly Thr Thr
            180                 185                 190

Gly Leu Pro Lys Gly Val Met Leu Thr His Arg Ser Leu Ile Thr Ser
            195                 200                 205

Val Ala Gln Gln Val Asp Gly Glu Asn Pro Asn Leu Tyr Phe Ser Lys
210                 215                 220

Asp Asp Val Ile Leu Cys Leu Leu Pro Leu Phe His Ile Tyr Ser Leu
225                 230                 235                 240

Asn Ser Val Leu Leu Ala Gly Leu Arg Ala Gly Ser Thr Ile Val Ile
                245                 250                 255

Met Arg Lys Phe Asp Leu Gly Ala Leu Val Asp Leu Val Arg Lys His

```
            260                 265                 270
Asn Ile Thr Ile Ala Pro Phe Val Pro Ile Val Val Glu Ile Ala
        275                 280                 285
Lys Ser Pro Arg Val Thr Ala Glu Asp Leu Ala Ser Ile Arg Met Val
    290                 295                 300
Met Ser Gly Ala Ala Pro Met Gly Lys Asp Leu Gln Asp Ala Phe Met
305                 310                 315                 320
Ala Lys Ile Pro Asn Ala Val Leu Gly Gln Gly Tyr Gly Met Thr Glu
                325                 330                 335
Ala Gly Pro Val Leu Ala Met Cys Leu Ala Phe Ala Lys Glu Pro Phe
                340                 345                 350
Lys Val Lys Ser Gly Ser Cys Gly Thr Val Val Arg Asn Ala Glu Leu
            355                 360                 365
Lys Ile Val Asp Pro Asp Thr Gly Thr Ser Leu Gly Arg Asn Gln Ser
        370                 375                 380
Gly Glu Ile Cys Ile Arg Gly Glu Gln Ile Met Lys Gly Tyr Leu Asn
385                 390                 395                 400
Asp Pro Glu Ala Thr Lys Asn Thr Ile Asp Glu Asp Gly Trp Leu His
                405                 410                 415
Thr Gly Asp Ile Gly Phe Val Asp Asp Asp Glu Ile Phe Ile Val
                420                 425                 430
Asp Arg Leu Lys Glu Ile Ile Lys Tyr Lys Gly Phe Gln Val Pro Pro
            435                 440                 445
Ala Glu Leu Glu Ala Leu Leu Ile Thr His Pro Glu Ile Lys Asp Ala
        450                 455                 460
Ala Val Val Ser Met Lys Asp Asp Leu Ala Gly Glu Val Pro Val Ala
465                 470                 475                 480
Phe Ile Val Arg Thr Glu Gly Ser Glu Ile Thr Glu Asp Glu Ile Lys
                485                 490                 495
Lys Phe Val Ala Lys Glu Val Val Phe Tyr Lys Arg Ile Asn Lys Val
                500                 505                 510
Phe Phe Thr Asp Ser Ile Pro Lys Asn Pro Ser Gly Lys Ile Leu Arg
            515                 520                 525
Lys Asp Leu Arg Ala Arg Leu Ala Ala Gly Ile Pro Asp Ala Val Ala
        530                 535                 540
Ala Ala Ala Ala Asp Ala Pro Lys Ser Ser
545                 550

<210> SEQ ID NO 31
<211> LENGTH: 559
<212> TYPE: PRT
<213> ORGANISM: Oryza sativa

<400> SEQUENCE: 31

Met Gly Ser Met Ala Ala Ala Glu Ala Ala Gln Glu Glu Glu Thr
1               5                   10                  15
Val Val Phe Arg Ser Lys Leu Pro Asp Ile Glu Ile Pro Ser His Leu
                20                  25                  30
Thr Leu Gln Ala Tyr Cys Phe Glu Lys Leu Pro Glu Val Ala Ala Arg
            35                  40                  45
Pro Cys Leu Ile Asp Gly Gln Thr Gly Ala Val Tyr Ser Tyr Gly Glu
        50                  55                  60
Val Glu Glu Leu Ser Arg Arg Ala Ala Ala Gly Leu Arg Arg Leu Gly
65                  70                  75                  80
```

```
Val Gly Lys Gly Asp Val Met Ser Leu Arg Asn Cys Pro Glu
                85                  90                  95

Phe Ala Phe Thr Phe Leu Gly Ala Ala Arg Leu Gly Ala Ala Thr Thr
            100                 105                 110

Thr Ala Asn Pro Phe Tyr Thr Pro His Glu Ile His Arg Gln Ala Ser
        115                 120                 125

Ala Ala Gly Ala Arg Val Ile Val Thr Glu Ala Cys Ala Val Glu Lys
    130                 135                 140

Val Arg Gly Phe Ala Ala Asp Arg Gly Ile Pro Val Val Ala Val Asp
145                 150                 155                 160

Gly Asp Phe Asp Gly Cys Val Gly Phe Gly Glu Ala Met Leu Asp Ala
                165                 170                 175

Ser Ile Glu Pro Leu Asp Ala Asp Glu Glu Val His Pro Asp Asp Val
            180                 185                 190

Val Ala Leu Pro Tyr Ser Ser Gly Thr Thr Gly Leu Pro Lys Gly Val
        195                 200                 205

Met Leu Thr His Arg Ser Leu Val Thr Ser Val Ala Gln Gln Val Asp
    210                 215                 220

Gly Glu Asn Pro Asn Leu Tyr Phe Arg Arg Glu Asp Val Val Leu Cys
225                 230                 235                 240

Leu Leu Pro Leu Phe His Ile Tyr Ser Leu Asn Ser Val Leu Leu Ala
                245                 250                 255

Gly Leu Arg Ala Gly Ser Ala Ile Val Ile Met Arg Lys Phe Asp Leu
            260                 265                 270

Gly Ala Leu Val Asp Leu Thr Arg Arg His Gly Val Thr Val Ala Pro
        275                 280                 285

Phe Val Pro Pro Ile Val Val Glu Ile Ala Lys Ser Pro Arg Val Thr
    290                 295                 300

Ala Asp Asp Leu Ala Ser Ile Arg Met Val Met Ser Gly Ala Ala Pro
305                 310                 315                 320

Met Gly Lys Asp Leu Gln Asp Ala Phe Met Ala Lys Ile Pro Asn Ala
                325                 330                 335

Val Leu Gly Gln Gly Tyr Gly Met Thr Glu Ala Gly Pro Val Leu Ala
            340                 345                 350

Met Cys Leu Ala Phe Ala Lys Glu Pro Phe Glu Val Lys Ser Gly Ser
        355                 360                 365

Cys Gly Thr Val Val Arg Asn Ala Glu Leu Lys Ile Val Asp Pro Asp
    370                 375                 380

Thr Gly Ala Thr Leu Gly Arg Asn Gln Ser Gly Glu Ile Cys Ile Arg
385                 390                 395                 400

Gly Glu Gln Ile Met Lys Gly Tyr Leu Asn Asp Pro Glu Ser Thr Lys
                405                 410                 415

Asn Thr Ile Asp Lys Gly Gly Trp Leu His Thr Gly Asp Ile Gly Tyr
            420                 425                 430

Val Asp Asp Asp Asp Glu Ile Phe Ile Val Asp Arg Leu Lys Glu Ile
        435                 440                 445

Ile Lys Tyr Lys Gly Phe Gln Val Pro Pro Ala Glu Leu Glu Ala Leu
    450                 455                 460

Leu Ile Thr His Pro Asp Ile Lys Asp Ala Ala Val Val Pro Met Ile
465                 470                 475                 480

Asp Glu Ile Ala Gly Glu Val Pro Val Ala Phe Ile Val Arg Ile Glu
                485                 490                 495

Gly Ser Ala Ile Ser Glu Asn Glu Ile Lys Gln Phe Val Ala Lys Glu
```

-continued

```
                500                 505                 510
Val Val Phe Tyr Lys Arg Leu Asn Lys Val Phe Phe Ala Asp Ser Ile
            515                 520                 525

Pro Lys Ser Pro Ser Gly Lys Ile Leu Arg Lys Asp Leu Arg Ala Lys
        530                 535                 540

Leu Ala Ala Gly Ile Pro Thr Asn Asp Asn Thr Gln Leu Lys Ser
545                 550                 555

<210> SEQ ID NO 32
<211> LENGTH: 564
<212> TYPE: PRT
<213> ORGANISM: Oryza sativa

<400> SEQUENCE: 32

Met Gly Ser Met Glu Gln Gln Gln Pro Glu Ser Ala Ala Pro Ala Thr
1               5                   10                  15

Glu Ala Ser Pro Glu Ile Ile Phe Arg Ser Lys Leu Gln Asp Ile Ala
            20                  25                  30

Ile Thr Asn Thr Leu Pro Leu His Arg Tyr Cys Phe Glu Arg Leu Pro
        35                  40                  45

Glu Val Ala Ala Arg Pro Cys Leu Ile Asp Gly Ala Thr Gly Gly Val
    50                  55                  60

Leu Thr Tyr Ala Asp Val Asp Arg Leu Ser Arg Arg Leu Ala Ala Ala
65                  70                  75                  80

Leu Arg Arg Ala Pro Leu Gly Leu Arg Gly Gly Val Val Met Ser
                85                  90                  95

Leu Leu Arg Asn Ser Pro Glu Phe Val Leu Ser Phe Phe Ala Ala Ser
            100                 105                 110

Arg Val Gly Ala Ala Val Thr Thr Ala Asn Pro Met Ser Thr Pro His
        115                 120                 125

Glu Ile Glu Ser Gln Leu Ala Ala Ala Gly Ala Thr Val Val Ile Thr
    130                 135                 140

Glu Ser Met Ala Ala Asp Lys Leu Pro Ser His Ser His Gly Ala Leu
145                 150                 155                 160

Thr Val Val Leu Ile Asp Glu Arg Arg Asp Gly Cys Leu His Phe Trp
                165                 170                 175

Asp Asp Leu Met Ser Glu Asp Glu Ala Ser Pro Leu Ala Gly Asp Glu
            180                 185                 190

Asp Asp Glu Lys Val Phe Asp Pro Asp Asp Val Val Ala Leu Pro Tyr
        195                 200                 205

Ser Ser Gly Thr Thr Gly Leu Pro Lys Gly Val Met Leu Thr His Arg
    210                 215                 220

Ser Leu Ser Thr Ser Val Ala Gln Gln Val Asp Gly Glu Asn Pro Asn
225                 230                 235                 240

Ile Gly Leu His Ala Gly Asp Val Ile Leu Cys Ala Leu Pro Met Phe
                245                 250                 255

His Ile Tyr Ser Leu Asn Thr Ile Met Met Cys Gly Leu Arg Val Gly
            260                 265                 270

Ala Ala Ile Val Val Met Arg Arg Phe Asp Leu Ala Ala Met Met Asp
        275                 280                 285

Leu Val Glu Arg His Arg Val Thr Ile Ala Pro Leu Val Pro Pro Ile
    290                 295                 300

Val Val Ala Val Ala Lys Ser Glu Ala Ala Ala Arg Asp Leu Ser
305                 310                 315                 320
```

```
Ser Val Arg Met Val Leu Ser Gly Ala Ala Pro Met Gly Lys Asp Ile
            325                 330                 335

Glu Asp Ala Phe Met Ala Lys Leu Pro Gly Ala Val Leu Gly Gln Gly
        340                 345                 350

Tyr Gly Met Thr Glu Ala Gly Pro Val Leu Ser Met Cys Leu Ala Phe
        355                 360                 365

Ala Lys Glu Pro Phe Lys Val Lys Ser Gly Ala Cys Gly Thr Val Val
370                 375                 380

Arg Asn Ala Glu Leu Lys Ile Ile Asp Pro Asp Thr Gly Lys Ser Leu
385                 390                 395                 400

Gly Arg Asn Leu Pro Gly Glu Ile Cys Ile Arg Gly Gln Gln Ile Met
                405                 410                 415

Lys Gly Tyr Leu Asn Asn Pro Glu Ala Thr Lys Asn Thr Ile Asp Ala
            420                 425                 430

Glu Gly Trp Leu His Thr Gly Asp Ile Gly Tyr Val Asp Asp Asp
        435                 440                 445

Glu Ile Phe Ile Val Asp Arg Leu Lys Glu Ile Ile Lys Tyr Arg Gly
    450                 455                 460

Phe Gln Val Ala Pro Ala Glu Leu Glu Ala Leu Leu Ile Thr His Pro
465                 470                 475                 480

Ser Ile Ala Asp Ala Ala Val Val Gly Lys Gln Ile Glu Pro Glu Ile
                485                 490                 495

Gly Glu Ile Pro Val Ala Phe Val Ala Lys Thr Glu Gly Ser Glu Leu
            500                 505                 510

Ser Glu Asp Asp Val Lys Gln Phe Val Ala Lys Glu Val Ile Tyr Tyr
        515                 520                 525

Lys Lys Ile Arg Glu Val Phe Phe Val Asp Lys Ile Pro Lys Ala Pro
530                 535                 540

Ser Gly Lys Ile Leu Arg Lys Glu Leu Arg Lys Gln Leu Gln His Leu
545                 550                 555                 560

Gln Gln Glu Ala

<210> SEQ ID NO 33
<211> LENGTH: 569
<212> TYPE: PRT
<213> ORGANISM: Oryza sativa

<400> SEQUENCE: 33

Met Ile Thr Val Ala Ala Pro Glu Ala Gln Pro Gln Val Ala Ala Ala
1               5                   10                  15

Val Asp Glu Ala Pro Pro Glu Ala Val Thr Val Phe Arg Ser Lys Leu
            20                  25                  30

Pro Asp Ile Asp Ile Pro Ser His Leu Pro Leu His Glu Tyr Cys Phe
        35                  40                  45

Ala Arg Ala Ala Glu Leu Pro Asp Ala Pro Cys Leu Ile Ala Ala Ala
    50                  55                  60

Thr Gly Arg Thr Tyr Thr Phe Ala Glu Thr Arg Leu Leu Cys Arg Arg
65                  70                  75                  80

Ala Ala Ala Ala Leu His Arg Leu Gly Val Gly His Gly Asp Arg Val
                85                  90                  95

Met Val Leu Leu Gln Asn Cys Val Glu Phe Ala Val Ala Phe Phe Ala
            100                 105                 110

Ala Ser Phe Leu Gly Ala Val Thr Thr Ala Ala Asn Pro Phe Cys Thr
        115                 120                 125
```

```
Pro Gln Glu Ile His Lys Gln Phe Lys Ala Ser Gly Val Lys Leu Ile
130                 135                 140

Leu Thr Gln Ser Val Tyr Val Asp Lys Leu Arg Gln His Glu Ala Phe
145                 150                 155                 160

Pro Arg Ile Asp Ala Cys Thr Val Gly Asp Asp Thr Leu Thr Val Ile
            165                 170                 175

Thr Ile Asp Asp Asp Glu Ala Thr Pro Glu Gly Cys Leu Pro Phe Trp
            180                 185                 190

Asp Leu Ile Ala Asp Ala Asp Glu Gly Ser Val Pro Glu Val Ala Ile
            195                 200                 205

Ser Pro Asp Asp Pro Val Ala Leu Pro Phe Ser Ser Gly Thr Thr Gly
210                 215                 220

Leu Pro Lys Gly Val Val Leu Thr His Arg Ser Val Val Ser Gly Val
225                 230                 235                 240

Ala Gln Gln Val Asp Gly Glu Asn Pro Asn Leu His Met Gly Ala Gly
                245                 250                 255

Asp Val Ala Leu Cys Val Leu Pro Leu Phe His Ile Phe Ser Leu Asn
                260                 265                 270

Ser Val Leu Leu Cys Ala Val Arg Ala Gly Ala Ala Val Ala Leu Met
    275                 280                 285

Pro Arg Phe Glu Met Gly Ala Met Leu Gly Ala Ile Glu Arg Trp Arg
290                 295                 300

Val Thr Val Ala Ala Val Pro Pro Leu Val Leu Ala Leu Ala Lys
305                 310                 315                 320

Asn Pro Phe Val Glu Arg His Asp Leu Ser Ser Ile Arg Ile Val Leu
                325                 330                 335

Ser Gly Ala Ala Pro Leu Gly Lys Glu Leu Glu Asp Ala Leu Arg Ala
                340                 345                 350

Arg Leu Pro Gln Ala Ile Phe Gly Gln Gly Tyr Gly Met Thr Glu Ala
            355                 360                 365

Gly Pro Val Leu Ser Met Cys Pro Ala Phe Ala Lys Glu Pro Thr Pro
    370                 375                 380

Ala Lys Ser Gly Ser Cys Gly Thr Val Val Arg Asn Ala Glu Leu Lys
385                 390                 395                 400

Val Val Asp Pro Asp Thr Gly Phe Ser Leu Gly Arg Asn Leu Pro Gly
            405                 410                 415

Glu Ile Cys Ile Arg Gly Pro Gln Ile Met Lys Gly Tyr Leu Asn Asp
            420                 425                 430

Pro Glu Ala Thr Ala Ala Thr Ile Asp Val Glu Gly Trp Leu His Thr
            435                 440                 445

Gly Asp Ile Gly Tyr Val Asp Asp Asp Glu Val Phe Ile Val Asp
450                 455                 460

Arg Val Lys Glu Leu Ile Lys Phe Lys Gly Phe Gln Val Pro Pro Ala
465                 470                 475                 480

Glu Leu Glu Ser Leu Leu Ile Ala His Pro Ser Ile Ala Asp Ala Ala
                485                 490                 495

Val Val Pro Gln Lys Asp Asp Val Ala Gly Glu Val Pro Val Ala Phe
                500                 505                 510

Val Val Arg Ala Ala Asp Ser Asp Ile Thr Glu Glu Ser Ile Lys Glu
            515                 520                 525

Phe Ile Ser Lys Gln Val Phe Tyr Lys Arg Leu His Lys Val His
530                 535                 540

Phe Ile His Ala Ile Pro Lys Ser Ala Ser Gly Lys Ile Leu Arg Arg
```

Glu Leu Arg Ala Lys Leu Ala Ala Cys
545                 550                 555                 560
            565

<210> SEQ ID NO 34
<211> LENGTH: 11
<212> TYPE: PRT
<213> ORGANISM: Arabidopsis thaliana

<400> SEQUENCE: 34

Ser Ser Gly Thr Thr Gly Leu Pro Lys Gly Val
1               5                   10

<210> SEQ ID NO 35
<211> LENGTH: 11
<212> TYPE: PRT
<213> ORGANISM: Arabidopsis thaliana

<400> SEQUENCE: 35

Ser Ser Gly Thr Thr Gly Leu Pro Lys Gly Val
1               5                   10

<210> SEQ ID NO 36
<211> LENGTH: 11
<212> TYPE: PRT
<213> ORGANISM: Arabidopsis thaliana

<400> SEQUENCE: 36

Ser Ser Gly Thr Thr Gly Leu Pro Lys Gly Val
1               5                   10

<210> SEQ ID NO 37
<211> LENGTH: 11
<212> TYPE: PRT
<213> ORGANISM: Arabidopsis thaliana

<400> SEQUENCE: 37

Ser Ser Gly Thr Thr Gly Leu Pro Lys Gly Val
1               5                   10

<210> SEQ ID NO 38
<211> LENGTH: 11
<212> TYPE: PRT
<213> ORGANISM: Poplar

<400> SEQUENCE: 38

Ser Ser Gly Thr Thr Gly Leu Pro Lys Gly Val
1               5                   10

<210> SEQ ID NO 39
<211> LENGTH: 11
<212> TYPE: PRT
<213> ORGANISM: Poplar

<400> SEQUENCE: 39

Ser Ser Gly Thr Thr Gly Leu Pro Lys Gly Val
1               5                   10

<210> SEQ ID NO 40
<211> LENGTH: 11
<212> TYPE: PRT
<213> ORGANISM: Poplar

<400> SEQUENCE: 40

```
Ser Ser Gly Thr Thr Gly Leu Pro Lys Gly Val
1               5                   10
```

```
<210> SEQ ID NO 41
<211> LENGTH: 11
<212> TYPE: PRT
<213> ORGANISM: Poplar

<400> SEQUENCE: 41
```

```
Ser Ser Gly Thr Thr Gly Leu Pro Lys Gly Val
1               5                   10
```

```
<210> SEQ ID NO 42
<211> LENGTH: 11
<212> TYPE: PRT
<213> ORGANISM: Saccharum

<400> SEQUENCE: 42
```

```
Ser Ser Gly Thr Thr Gly Leu Pro Lys Gly Val
1               5                   10
```

```
<210> SEQ ID NO 43
<211> LENGTH: 11
<212> TYPE: PRT
<213> ORGANISM: Saccharum

<400> SEQUENCE: 43
```

```
Ser Ser Gly Thr Thr Gly Leu Pro Lys Gly Val
1               5                   10
```

```
<210> SEQ ID NO 44
<211> LENGTH: 7
<212> TYPE: PRT
<213> ORGANISM: Arabidopsis thaliana

<400> SEQUENCE: 44
```

```
Gly Glu Ile Cys Ile Arg Gly
1               5
```

```
<210> SEQ ID NO 45
<211> LENGTH: 7
<212> TYPE: PRT
<213> ORGANISM: Arabidopsis thaliana

<400> SEQUENCE: 45
```

```
Gly Glu Ile Cys Ile Arg Gly
1               5
```

```
<210> SEQ ID NO 46
<211> LENGTH: 7
<212> TYPE: PRT
<213> ORGANISM: Arabidopsis thaliana

<400> SEQUENCE: 46
```

```
Gly Glu Ile Cys Ile Arg Gly
1               5
```

```
<210> SEQ ID NO 47
<211> LENGTH: 7
<212> TYPE: PRT
<213> ORGANISM: Arabidopsis thaliana

<400> SEQUENCE: 47
```

```
Gly Glu Ile Cys Val Arg Gly
1               5
```

```
<210> SEQ ID NO 48
<211> LENGTH: 7
<212> TYPE: PRT
<213> ORGANISM: Poplar

<400> SEQUENCE: 48

Gly Glu Ile Cys Ile Arg Gly
1               5

<210> SEQ ID NO 49
<211> LENGTH: 7
<212> TYPE: PRT
<213> ORGANISM: Poplar

<400> SEQUENCE: 49

Gly Glu Ile Cys Ile Arg Gly
1               5

<210> SEQ ID NO 50
<211> LENGTH: 7
<212> TYPE: PRT
<213> ORGANISM: Poplar

<400> SEQUENCE: 50

Gly Glu Ile Cys Ile Arg Gly
1               5

<210> SEQ ID NO 51
<211> LENGTH: 7
<212> TYPE: PRT
<213> ORGANISM: Poplar

<400> SEQUENCE: 51

Gly Glu Ile Cys Ile Arg Gly
1               5

<210> SEQ ID NO 52
<211> LENGTH: 7
<212> TYPE: PRT
<213> ORGANISM: Saccharum

<400> SEQUENCE: 52

Gly Glu Ile Cys Ile Arg Gly
1               5

<210> SEQ ID NO 53
<211> LENGTH: 7
<212> TYPE: PRT
<213> ORGANISM: Saccharum

<400> SEQUENCE: 53

Gly Glu Ile Cys Ile Arg Gly
1               5

<210> SEQ ID NO 54
<211> LENGTH: 7
<212> TYPE: PRT
<213> ORGANISM: Saccharum

<400> SEQUENCE: 54

Gly Glu Ile Cys Ile Arg Gly
1               5
```